(12) United States Patent
Hyde et al.

(10) Patent No.: US 9,295,393 B2
(45) Date of Patent: Mar. 29, 2016

(54) EMBOLISM DEFLECTOR

(71) Applicant: Elwha LLC, Bellevue, WA (US)

(72) Inventors: Roderick A. Hyde, Redmond, WA (US); Muriel Y. Ishikawa, Livermore, CA (US); Eric C. Leuthardt, St. Louis, MO (US); Nathan P. Myhrvold, Medina, WA (US); Clarence T. Tegreene, Mercer Island, WA (US); Charles Whitmer, North Bend, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 336 days.

(21) Appl. No.: 13/673,016

(22) Filed: Nov. 9, 2012

(65) Prior Publication Data

US 2014/0135815 A1 May 15, 2014

(51) Int. Cl.
*A61M 29/00* (2006.01)
*A61B 5/02* (2006.01)
(Continued)

(52) U.S. Cl.
CPC ............ *A61B 5/02007* (2013.01); *A61B 5/06* (2013.01); *A61B 17/1204* (2013.01); *A61B 17/12036* (2013.01); *A61B 17/12109* (2013.01); *A61F 2/01* (2013.01); *A61F 2/2418* (2013.01); *A61F 2/90* (2013.01); *A61B 5/0084* (2013.01); *A61B 8/085* (2013.01); *A61B 8/0891* (2013.01); *A61B 8/12* (2013.01); *A61B 17/12118* (2013.01); *A61B 17/22* (2013.01); *A61B 2017/0061* (2013.01);
(Continued)

(58) Field of Classification Search
CPC .. A61F 2/95; A61B 17/1204; A61B 5/02007; A61B 17/12109; A61B 17/12036
USPC .......................................... 606/200; 600/469
See application file for complete search history.

(56) References Cited

U.S. PATENT DOCUMENTS

| 4,375,415 A | 3/1983 | Lavender |
| 4,376,325 A | 3/1983 | Boas et al. |

(Continued)

FOREIGN PATENT DOCUMENTS

| EP | 0 348 271 A1 | 6/1989 |
| EP | 0 714 667 A2 | 6/1996 |

(Continued)

OTHER PUBLICATIONS

Blum et al.; "Neurology® Memory after Silent Stroke: Hippocampus and Infarcts both Matter"; American Academy of Neurology; bearing a date of Dec. 29, 2011; pp. 38-46, plus cover and end sheet; vol. 78, No. 38; AAN Enterprises, Inc.

(Continued)

*Primary Examiner* — Richard Louis
(74) *Attorney, Agent, or Firm* — Faisal K. Abou-Nasr; Advent, LLP

(57) ABSTRACT

Devices, methods, and systems provide an embolism deflecting device, methods for deflecting or diverting emboli away from critical locations in the body, and systems therefor. Embodiments of the embolism deflecting device comprise an embolism detector, a diverter controller operable for determining the presence of emboli from a target input from the embolism detector, and an embolism diverter operable by the diverter controller to deflect, divert, redirect, etc., emboli away from the critical body location on the detection thereof.

17 Claims, 22 Drawing Sheets

(51) Int. Cl.
  *A61F 2/01* (2006.01)
  *A61F 2/24* (2006.01)
  *A61B 5/06* (2006.01)
  *A61F 2/90* (2013.01)
  *A61B 17/12* (2006.01)
  *A61B 5/00* (2006.01)
  *A61B 8/08* (2006.01)
  *A61B 8/12* (2006.01)
  *A61N 7/00* (2006.01)
  *A61B 17/22* (2006.01)
  *A61B 17/00* (2006.01)

(52) U.S. Cl.
  CPC ............... *A61B 2017/00345* (2013.01); *A61B 2017/00725* (2013.01); *A61F 2002/016* (2013.01); *A61F 2002/018* (2013.01); *A61F 2220/0091* (2013.01); *A61F 2230/0008* (2013.01); *A61F 2230/0026* (2013.01); *A61F 2230/0054* (2013.01); *A61F 2230/0095* (2013.01); *A61N 2007/0043* (2013.01)

(56) References Cited

U.S. PATENT DOCUMENTS

| | | |
|---|---|---|
| 4,425,908 A | 1/1984 | Simon |
| 4,494,531 A | 1/1985 | Gianturco |
| 4,723,549 A | 2/1988 | Wholey et al. |
| 4,817,600 A | 4/1989 | Herms et al. |
| 4,997,577 A | 3/1991 | Stewart |
| 5,059,205 A | 10/1991 | El-Nounou et al. |
| 5,108,419 A | 4/1992 | Reger et al. |
| 5,160,342 A | 11/1992 | Reger et al. |
| 5,242,462 A | 9/1993 | El-Nounou et al. |
| 5,305,745 A | 4/1994 | Zacouto |
| 5,353,798 A | 10/1994 | Sieben |
| 5,375,612 A | 12/1994 | Cottenceau et al. |
| 5,383,887 A | 1/1995 | Nadal |
| 5,407,426 A | 4/1995 | Spears |
| 5,513,532 A | 5/1996 | Beffy et al. |
| 5,527,472 A | 6/1996 | Bellotti et al. |
| 5,556,414 A | 9/1996 | Turi |
| 5,567,440 A | 10/1996 | Hubbell et al. |
| 5,601,595 A | 2/1997 | Smith |
| 5,626,605 A | 5/1997 | Irie et al. |
| 5,628,781 A | 5/1997 | Williams et al. |
| 5,718,711 A | 2/1998 | Berenstein et al. |
| RE35,804 E | 5/1998 | Stewart |
| 5,746,767 A | 5/1998 | Smith |
| 5,769,816 A | 6/1998 | Barbut et al. |
| 5,800,525 A | 9/1998 | Bachinski et al. |
| 5,820,593 A | 10/1998 | Safar et al. |
| 5,826,587 A | 10/1998 | Berenstein et al. |
| 5,836,934 A | 11/1998 | Beshel |
| 5,843,156 A | 12/1998 | Slepian et al. |
| 5,846,260 A | 12/1998 | Maahs |
| 5,855,599 A | 1/1999 | Wan |
| 5,893,869 A | 4/1999 | Barnhart et al. |
| 5,944,684 A | 8/1999 | Roberts et al. |
| 5,980,555 A | 11/1999 | Barbut et al. |
| 5,984,947 A | 11/1999 | Smith |
| 5,984,956 A | 11/1999 | Tweden et al. |
| 5,989,281 A | 11/1999 | Barbut et al. |
| 5,995,868 A | 11/1999 | Dorfmeister et al. |
| 6,007,557 A | 12/1999 | Ambrisco et al. |
| 6,030,397 A | 2/2000 | Monetti et al. |
| 6,045,788 A | 4/2000 | Smith |
| 6,051,015 A | 4/2000 | Maahs |
| 6,053,885 A | 4/2000 | Beshel |
| 6,053,942 A | 4/2000 | Eno et al. |
| 6,059,745 A | 5/2000 | Gelbfish |
| 6,066,149 A | 5/2000 | Samson et al. |
| 6,068,645 A | 5/2000 | Tu |
| 6,086,605 A | 7/2000 | Barbut et al. |
| 6,099,561 A | 8/2000 | Alt |
| 6,102,941 A | 8/2000 | Tweden et al. |
| 6,106,497 A | 8/2000 | Wang |
| 6,117,154 A | 9/2000 | Barbut et al. |
| 6,132,841 A | 10/2000 | Guthrie et al. |
| 6,136,016 A | 10/2000 | Barbut et al. |
| 6,139,520 A | 10/2000 | McCrory et al. |
| 6,152,947 A | 11/2000 | Ambrisco et al. |
| 6,159,142 A | 12/2000 | Alt |
| 6,161,038 A | 12/2000 | Schookin et al. |
| 6,171,251 B1 | 1/2001 | Mueller et al. |
| 6,179,789 B1 | 1/2001 | Tu et al. |
| 6,193,726 B1 | 2/2001 | Vanney |
| 6,197,050 B1 | 3/2001 | Eno et al. |
| 6,197,345 B1 | 3/2001 | Porter |
| 6,214,025 B1 | 4/2001 | Thistle et al. |
| 6,214,041 B1 | 4/2001 | Tweden et al. |
| 6,224,620 B1 | 5/2001 | Maahs |
| 6,231,544 B1 | 5/2001 | Tsugita et al. |
| 6,235,045 B1 | 5/2001 | Barbut et al. |
| 6,245,782 B1 | 6/2001 | Serebruany et al. |
| 6,251,418 B1 | 6/2001 | Ahern et al. |
| 6,258,120 B1 | 7/2001 | McKenzie et al. |
| 6,267,776 B1 | 7/2001 | O'Connell |
| 6,273,900 B1 | 8/2001 | Nott et al. |
| 6,273,901 B1 | 8/2001 | Whitcher et al. |
| 6,290,718 B1 | 9/2001 | Grooms et al. |
| 6,299,590 B1 | 10/2001 | Lüscher et al. |
| 6,306,164 B1 | 10/2001 | Kujawski et al. |
| 6,309,399 B1 | 10/2001 | Barbut et al. |
| 6,312,407 B1 | 11/2001 | Zadno-Azizi et al. |
| 6,319,268 B1 | 11/2001 | Ambrisco et al. |
| 6,340,364 B2 | 1/2002 | Kanesaka |
| 6,348,063 B1 | 2/2002 | Yassour et al. |
| 6,358,420 B2 | 3/2002 | Blickhan et al. |
| 6,361,545 B1 | 3/2002 | Macoviak et al. |
| 6,363,938 B2 | 4/2002 | Saadat et al. |
| 6,371,935 B1 | 4/2002 | Macoviak et al. |
| 6,383,205 B1 | 5/2002 | Samson et al. |
| 6,395,014 B1 | 5/2002 | Macoviak et al. |
| 6,398,756 B2 | 6/2002 | Peterson et al. |
| 6,406,471 B1 | 6/2002 | Jang et al. |
| 6,406,491 B1 | 6/2002 | Vanney |
| 6,409,697 B2 | 6/2002 | Eno et al. |
| 6,423,032 B2 | 7/2002 | Parodi |
| 6,425,914 B1 | 7/2002 | Wallace et al. |
| 6,451,257 B1 | 9/2002 | Flamer |
| 6,454,760 B2 | 9/2002 | Vanney |
| 6,458,069 B1 | 10/2002 | Tam et al. |
| 6,471,689 B1 | 10/2002 | Joseph et al. |
| 6,478,776 B1 | 11/2002 | Rosenman et al. |
| 6,485,502 B2 | 11/2002 | Don Michael et al. |
| 6,494,882 B1 | 12/2002 | Lebouitz et al. |
| 6,497,709 B1 | 12/2002 | Heath |
| 6,499,487 B1 | 12/2002 | McKenzie et al. |
| 6,505,133 B1 | 1/2003 | Hanna et al. |
| 6,508,824 B1 | 1/2003 | Flaherty et al. |
| 6,508,826 B2 | 1/2003 | Murphy et al. |
| 6,509,313 B1 | 1/2003 | Smith |
| 6,511,496 B1 | 1/2003 | Huter et al. |
| 6,517,559 B1 | 2/2003 | O'Connell |
| 6,530,939 B1 | 3/2003 | Hopkins et al. |
| 6,540,722 B1 | 4/2003 | Boyle et al. |
| 6,551,268 B1 | 4/2003 | Kaganov et al. |
| 6,551,303 B1 | 4/2003 | Van Tassel et al. |
| 6,552,014 B2 | 4/2003 | Serebruany et al. |
| 6,558,356 B2 | 5/2003 | Barbut |
| 6,558,405 B1 | 5/2003 | McInnes |
| 6,582,396 B1 | 6/2003 | Parodi |
| 6,589,264 B1 | 7/2003 | Barbut et al. |
| 6,589,266 B2 | 7/2003 | Whitcher et al. |
| 6,592,546 B1 | 7/2003 | Barbut et al. |
| 6,601,710 B2 | 8/2003 | Calhoun et al. |
| 6,605,053 B1 | 8/2003 | Kamm et al. |
| 6,607,501 B2 | 8/2003 | Gorsuch |
| 6,623,506 B2 | 9/2003 | McGuckin, Jr. et al. |
| 6,623,507 B2 | 9/2003 | Saleh |
| 6,635,070 B2 | 10/2003 | Leeflang et al. |
| 6,641,610 B2 | 11/2003 | Wolf et al. |

(56) References Cited

U.S. PATENT DOCUMENTS

| | | |
|---|---|---|
| 6,645,220 B1 | 11/2003 | Huter et al. |
| 6,645,221 B1 | 11/2003 | Richter |
| 6,645,222 B1 | 11/2003 | Parodi et al. |
| 6,656,204 B2 | 12/2003 | Ambrisco et al. |
| 6,659,973 B2 | 12/2003 | Gorsuch et al. |
| 6,663,607 B2 | 12/2003 | Slaikeu et al. |
| 6,663,765 B2 | 12/2003 | Cherkes |
| 6,673,089 B1 | 1/2004 | Yassour et al. |
| 6,685,664 B2 | 2/2004 | Levin et al. |
| 6,689,084 B2 | 2/2004 | Kaganov et al. |
| 6,695,811 B2 | 2/2004 | Samson et al. |
| 6,695,813 B1 | 2/2004 | Boyle et al. |
| 6,712,834 B2 | 3/2004 | Yassour et al. |
| 6,712,835 B2 | 3/2004 | Mazzocchi et al. |
| 6,716,208 B2 | 4/2004 | Humes |
| 6,719,717 B1 | 4/2004 | Johnson et al. |
| 6,723,085 B2 | 4/2004 | Jang et al. |
| 6,740,112 B2 | 5/2004 | Yodfat et al. |
| 6,743,246 B1 | 6/2004 | Maahs |
| 6,767,360 B1 | 7/2004 | Alt et al. |
| 6,776,770 B1 | 8/2004 | Trerotola |
| 6,793,665 B2 | 9/2004 | McGuckin, Jr. et al. |
| 6,849,183 B2 | 2/2005 | Gorsuch et al. |
| 6,866,680 B2 | 3/2005 | Yassour et al. |
| 6,878,164 B2 | 4/2005 | Kujawski et al. |
| 6,905,490 B2 | 6/2005 | Parodi |
| 6,908,474 B2 | 6/2005 | Hogendijk et al. |
| 6,909,920 B2 | 6/2005 | Lokhoff et al. |
| 6,916,304 B2 | 7/2005 | Eno et al. |
| 6,941,169 B2 | 9/2005 | Pappu |
| 6,949,080 B2 | 9/2005 | Wolf et al. |
| 6,949,113 B2 | 9/2005 | Van Tassel et al. |
| 6,949,118 B2 | 9/2005 | Kohler et al. |
| 6,951,570 B2 | 10/2005 | Linder et al. |
| 6,962,598 B2 | 11/2005 | Linder et al. |
| 6,994,689 B1 | 2/2006 | Zadno-Azizi et al. |
| 6,997,939 B2 | 2/2006 | Linder et al. |
| 7,008,397 B2 | 3/2006 | Tweden et al. |
| 7,011,095 B2 | 3/2006 | Wolf et al. |
| 7,011,672 B2 | 3/2006 | Barbut et al. |
| 7,022,135 B2 | 4/2006 | Zilla et al. |
| 7,033,375 B2 | 4/2006 | Mazzocchi et al. |
| 2001/0001111 A1 | 5/2001 | Spears et al. |
| 2001/0007947 A1 | 7/2001 | Kanesaka |
| 2001/0011181 A1 | 8/2001 | DiMatteo |
| 2001/0012948 A1 | 8/2001 | Vanney |
| 2001/0016700 A1 | 8/2001 | Eno et al. |
| 2001/0023358 A1 | 9/2001 | Tsukernik |
| 2001/0027332 A1 | 10/2001 | Grunwald et al. |
| 2001/0031982 A1 | 10/2001 | Peterson et al. |
| 2001/0033867 A1 | 10/2001 | Ahern et al. |
| 2001/0037978 A1 | 11/2001 | Calhoun et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0044598 A1 | 11/2001 | Parodi |
| 2001/0044634 A1 | 11/2001 | Don Michael et al. |
| 2001/0049486 A1 | 12/2001 | Evans et al. |
| 2001/0052497 A1 | 12/2001 | Blickhan et al. |
| 2002/0002384 A1 | 1/2002 | Gilson et al. |
| 2002/0013343 A1 | 1/2002 | Serebruany et al. |
| 2002/0013620 A1 | 1/2002 | Kujawski |
| 2002/0016624 A1 | 2/2002 | Patterson et al. |
| 2002/0023843 A1 | 2/2002 | Cherkes |
| 2002/0026211 A1 | 2/2002 | Khosravi et al. |
| 2002/0026213 A1 | 2/2002 | Gilson et al. |
| 2002/0026217 A1 | 2/2002 | Baker et al. |
| 2002/0032476 A1 | 3/2002 | Gambale et al. |
| 2002/0036058 A1 | 3/2002 | Sunseri |
| 2002/0042564 A1 | 4/2002 | Cooper et al. |
| 2002/0042565 A1 | 4/2002 | Cooper et al. |
| 2002/0045915 A1 | 4/2002 | Balceta et al. |
| 2002/0045917 A1 | 4/2002 | Ambrisco et al. |
| 2002/0045918 A1 | 4/2002 | Suon et al. |
| 2002/0049370 A1 | 4/2002 | Laufer et al. |
| 2002/0049491 A1* | 4/2002 | Yassour et al. ............... 623/1.15 |
| 2002/0062092 A1 | 5/2002 | Muni et al. |
| 2002/0062134 A1 | 5/2002 | Barbut et al. |
| 2002/0062135 A1 | 5/2002 | Mazzocchi et al. |
| 2002/0063090 A1 | 5/2002 | Calhoun et al. |
| 2002/0065478 A1 | 5/2002 | Knudson et al. |
| 2002/0068955 A1 | 6/2002 | Khosravi |
| 2002/0072699 A1 | 6/2002 | Knudson et al. |
| 2002/0072712 A1 | 6/2002 | Nool et al. |
| 2002/0077581 A1 | 6/2002 | Davidner et al. |
| 2002/0082558 A1 | 6/2002 | Samson et al. |
| 2002/0082685 A1 | 6/2002 | Sirhan et al. |
| 2002/0087109 A1 | 7/2002 | Gorsuch et al. |
| 2002/0087119 A1 | 7/2002 | Parodi |
| 2002/0090389 A1 | 7/2002 | Humes et al. |
| 2002/0091409 A1 | 7/2002 | Sutton et al. |
| 2002/0095110 A1 | 7/2002 | Vanney et al. |
| 2002/0095172 A1 | 7/2002 | Mazzocchi et al. |
| 2002/0103512 A1 | 8/2002 | Echauz et al. |
| 2002/0123715 A1 | 9/2002 | Sorenson et al. |
| 2002/0123755 A1 | 9/2002 | Lowe et al. |
| 2002/0123766 A1 | 9/2002 | Seguin et al. |
| 2002/0133217 A1 | 9/2002 | Sirhan et al. |
| 2002/0138094 A1 | 9/2002 | Borillo et al. |
| 2002/0138097 A1 | 9/2002 | Ostrovsky et al. |
| 2002/0143285 A1 | 10/2002 | Eno et al. |
| 2002/0143298 A1 | 10/2002 | Marsden |
| 2002/0147480 A1 | 10/2002 | Mamayek |
| 2002/0151917 A1 | 10/2002 | Barry |
| 2002/0156455 A1 | 10/2002 | Barbut |
| 2002/0161391 A1 | 10/2002 | Murphy et al. |
| 2002/0161393 A1 | 10/2002 | Demond et al. |
| 2002/0161396 A1 | 10/2002 | Jang et al. |
| 2002/0161423 A1 | 10/2002 | Lokhoff et al. |
| 2002/0165575 A1* | 11/2002 | Saleh .......................... 606/200 |
| 2002/0169437 A1 | 11/2002 | Macoviak et al. |
| 2002/0173815 A1 | 11/2002 | Hogendijk et al. |
| 2002/0173819 A1 | 11/2002 | Leeflang et al. |
| 2002/0176893 A1 | 11/2002 | Wironen et al. |
| 2002/0183823 A1 | 12/2002 | Pappu |
| 2002/0187069 A1 | 12/2002 | Levin et al. |
| 2002/0188240 A1 | 12/2002 | Gorsuch |
| 2002/0193826 A1 | 12/2002 | McGuckin, Jr. et al. |
| 2003/0000886 A1 | 1/2003 | Breillatt et al. |
| 2003/0004540 A1 | 1/2003 | Linder et al. |
| 2003/0009189 A1 | 1/2003 | Gilson et al. |
| 2003/0010702 A1 | 1/2003 | Stillig et al. |
| 2003/0014003 A1 | 1/2003 | Gertner |
| 2003/0023263 A1 | 1/2003 | Krolik et al. |
| 2003/0036728 A1 | 2/2003 | Samson et al. |
| 2003/0045927 A1 | 3/2003 | Zilla et al. |
| 2003/0049841 A1 | 3/2003 | Short et al. |
| 2003/0050662 A1 | 3/2003 | Don Michael |
| 2003/0055360 A1 | 3/2003 | Zeleznik et al. |
| 2003/0060844 A1 | 3/2003 | Borillo et al. |
| 2003/0069532 A1 | 4/2003 | Mowry et al. |
| 2003/0069597 A1 | 4/2003 | Petersen |
| 2003/0071285 A1 | 4/2003 | Tsukernik |
| 2003/0073946 A1 | 4/2003 | Gorsuch et al. |
| 2003/0078614 A1 | 4/2003 | Salahieh et al. |
| 2003/0100845 A1 | 5/2003 | Eide |
| 2003/0105485 A1 | 6/2003 | Balceta et al. |
| 2003/0105486 A1 | 6/2003 | Murphy et al. |
| 2003/0105508 A1 | 6/2003 | Johnson et al. |
| 2003/0109824 A1 | 6/2003 | Anderson et al. |
| 2003/0109897 A1 | 6/2003 | Walak et al. |
| 2003/0114879 A1 | 6/2003 | Euteneuer et al. |
| 2003/0120304 A1 | 6/2003 | Kaganov et al. |
| 2003/0125790 A1 | 7/2003 | Fastovsky et al. |
| 2003/0130681 A1 | 7/2003 | Ungs |
| 2003/0130682 A1 | 7/2003 | Broome et al. |
| 2003/0135260 A1 | 7/2003 | Kohler et al. |
| 2003/0139764 A1 | 7/2003 | Levinson et al. |
| 2003/0144686 A1 | 7/2003 | Martinez et al. |
| 2003/0153943 A1 | 8/2003 | Michael et al. |
| 2003/0158509 A1 | 8/2003 | Tweden et al. |
| 2003/0158571 A1 | 8/2003 | Esch et al. |
| 2003/0158574 A1 | 8/2003 | Esch et al. |
| 2003/0158587 A1 | 8/2003 | Esteller et al. |

(56) References Cited

U.S. PATENT DOCUMENTS

| | | |
|---|---|---|
| 2003/0163017 A1 | 8/2003 | Tam et al. |
| 2003/0171771 A1 | 9/2003 | Anderson et al. |
| 2003/0171803 A1 | 9/2003 | Shimon |
| 2003/0176888 A1 | 9/2003 | O'Connell |
| 2003/0181942 A1 | 9/2003 | Sutton et al. |
| 2003/0191493 A1 | 10/2003 | Epstein et al. |
| 2003/0204248 A1 | 10/2003 | Murphy |
| 2003/0208228 A1 | 11/2003 | Gilson et al. |
| 2003/0208253 A1 | 11/2003 | Beyer et al. |
| 2003/0212361 A1 | 11/2003 | Boyle et al. |
| 2003/0212428 A1 | 11/2003 | Richter |
| 2003/0216774 A1 | 11/2003 | Larson |
| 2003/0220556 A1 | 11/2003 | Porat et al. |
| 2003/0220661 A1 | 11/2003 | Mowry et al. |
| 2003/0233115 A1 | 12/2003 | Eversull et al. |
| 2003/0233126 A1 | 12/2003 | Kaplan et al. |
| 2003/0233143 A1 | 12/2003 | Gharib et al. |
| 2003/0236482 A1 | 12/2003 | Gorsuch et al. |
| 2003/0236496 A1 | 12/2003 | Samson et al. |
| 2004/0006369 A1 | 1/2004 | DiMatteo |
| 2004/0009205 A1 | 1/2004 | Sawhney |
| 2004/0010307 A1 | 1/2004 | Grad et al. |
| 2004/0010308 A1 | 1/2004 | Zafrir-Pachter et al. |
| 2004/0015070 A1 | 1/2004 | Liang et al. |
| 2004/0019312 A1 | 1/2004 | Childers et al. |
| 2004/0024416 A1 | 2/2004 | Yodfat et al. |
| 2004/0030217 A1 | 2/2004 | Yeung et al. |
| 2004/0034317 A1 | 2/2004 | Gorsuch et al. |
| 2004/0034385 A1 | 2/2004 | Gilson et al. |
| 2004/0039371 A1 | 2/2004 | Tockman et al. |
| 2004/0039411 A1 | 2/2004 | Gilson et al. |
| 2004/0039438 A1 | 2/2004 | Alt |
| 2004/0044301 A1 | 3/2004 | Levin et al. |
| 2004/0049171 A1 | 3/2004 | Mowry et al. |
| 2004/0049207 A1 | 3/2004 | Goldfarb et al. |
| 2004/0054401 A1 | 3/2004 | Kujawski et al. |
| 2004/0057945 A1 | 3/2004 | Maier et al. |
| 2004/0059280 A1 | 3/2004 | Makower et al. |
| 2004/0059373 A1 | 3/2004 | Shapiro et al. |
| 2004/0064092 A1 | 4/2004 | Tsugita et al. |
| 2004/0073198 A1 | 4/2004 | Gilson et al. |
| 2004/0077990 A1 | 4/2004 | Knudson et al. |
| 2004/0092890 A1 | 5/2004 | Ash |
| 2004/0098022 A1 | 5/2004 | Barone |
| 2004/0098033 A1 | 5/2004 | Leeflang et al. |
| 2004/0116959 A1 | 6/2004 | McGuckin, Jr. et al. |
| 2004/0116960 A1 | 6/2004 | Demond et al. |
| 2004/0121343 A1 | 6/2004 | Buechler et al. |
| 2004/0122011 A1 | 6/2004 | Masferrer et al. |
| 2004/0122347 A1 | 6/2004 | Knudson et al. |
| 2004/0122468 A1 | 6/2004 | Yodfat et al. |
| 2004/0127840 A1 | 7/2004 | Gara et al. |
| 2004/0127843 A1 | 7/2004 | Tu et al. |
| 2004/0127979 A1 | 7/2004 | Wilson et al. |
| 2004/0132003 A1 | 7/2004 | Dolecek et al. |
| 2004/0143226 A1 | 7/2004 | Marsden |
| 2004/0147837 A1 | 7/2004 | Macaulay et al. |
| 2004/0147868 A1 | 7/2004 | Bardsley et al. |
| 2004/0153117 A1 | 8/2004 | Clubb et al. |
| 2004/0153118 A1 | 8/2004 | Clubb et al. |
| 2004/0153119 A1 | 8/2004 | Kusleika et al. |
| 2004/0158274 A1 | 8/2004 | WasDyke |
| 2004/0158276 A1 | 8/2004 | Barbut et al. |
| 2004/0158277 A1 | 8/2004 | Lowe et al. |
| 2004/0158279 A1 | 8/2004 | Petersen |
| 2004/0162613 A1 | 8/2004 | Roballey |
| 2004/0167597 A1 | 8/2004 | Costantino et al. |
| 2004/0167613 A1 | 8/2004 | Yodfat et al. |
| 2004/0172042 A1 | 9/2004 | Suon et al. |
| 2004/0176794 A1 | 9/2004 | Khosravi |
| 2004/0185426 A1 | 9/2004 | Mallett et al. |
| 2004/0186407 A1 | 9/2004 | Walker et al. |
| 2004/0193178 A1 | 9/2004 | Nikolchev |
| 2004/0193179 A1 | 9/2004 | Nikolchev |
| 2004/0199243 A1 | 10/2004 | Yodfat |
| 2004/0204745 A1 | 10/2004 | Altshuler et al. |
| 2004/0204754 A1 | 10/2004 | Kaplan et al. |
| 2004/0210154 A1 | 10/2004 | Kline |
| 2004/0211260 A1 | 10/2004 | Girmonsky et al. |
| 2004/0215168 A1 | 10/2004 | Verrier et al. |
| 2004/0219214 A1 | 11/2004 | Gravett et al. |
| 2004/0220585 A1 | 11/2004 | Nikolchev |
| 2004/0225249 A1 | 11/2004 | Leonard et al. |
| 2004/0225286 A1 | 11/2004 | Elliott |
| 2004/0230117 A1 | 11/2004 | Tosaya et al. |
| 2004/0249416 A1 | 12/2004 | Yun et al. |
| 2004/0254603 A1 | 12/2004 | Maahs |
| 2004/0254632 A1 | 12/2004 | Alt et al. |
| 2005/0004641 A1 | 1/2005 | Pappu |
| 2005/0004652 A1 | 1/2005 | Van der Burg et al. |
| 2005/0008708 A1 | 1/2005 | Dai et al. |
| 2005/0021092 A1 | 1/2005 | Yun et al. |
| 2005/0021152 A1 | 1/2005 | Ogle et al. |
| 2005/0025752 A1 | 2/2005 | Kutryk et al. |
| 2005/0027247 A1 | 2/2005 | Carrison et al. |
| 2005/0027265 A1 | 2/2005 | Maki et al. |
| 2005/0027314 A1 | 2/2005 | WasDyke |
| 2005/0027345 A1 | 2/2005 | Horan et al. |
| 2005/0032218 A1 | 2/2005 | Gerlach |
| 2005/0033347 A1 | 2/2005 | Rauker et al. |
| 2005/0038468 A1 | 2/2005 | Panetta et al. |
| 2005/0049539 A1 | 3/2005 | O'Hara, Jr. et al. |
| 2005/0055082 A1 | 3/2005 | Ben Muvhar et al. |
| 2005/0070989 A1 | 3/2005 | Lye et al. |
| 2005/0070993 A1 | 3/2005 | Boekstegers et al. |
| 2005/0075662 A1 | 4/2005 | Pedersen et al. |
| 2005/0082210 A1 | 4/2005 | Favre |
| 2005/0085842 A1 | 4/2005 | Eversull et al. |
| 2005/0090846 A1 | 4/2005 | Pedersen et al. |
| 2005/0101904 A1 | 5/2005 | Wilk |
| 2005/0101920 A1 | 5/2005 | Keane et al. |
| 2005/0101982 A1 | 5/2005 | Ravenscroft et al. |
| 2005/0119597 A1 | 6/2005 | O'Mahony et al. |
| 2005/0119688 A1* | 6/2005 | Bergheim ............... 606/200 |
| 2005/0119689 A1 | 6/2005 | Mazzocchi et al. |
| 2005/0119690 A1 | 6/2005 | Mazzocchi et al. |
| 2005/0131340 A1 | 6/2005 | Sorenson et al. |
| 2005/0131451 A1 | 6/2005 | Kleshinski et al. |
| 2005/0131452 A1 | 6/2005 | Walak et al. |
| 2005/0131453 A1 | 6/2005 | Parodi |
| 2005/0142315 A1 | 6/2005 | DeSimone et al. |
| 2005/0143378 A1 | 6/2005 | Yun et al. |
| 2005/0149186 A1 | 7/2005 | Roballey et al. |
| 2005/0154299 A1 | 7/2005 | Hoctor et al. |
| 2005/0154454 A1 | 7/2005 | Hunter et al. |
| 2005/0155932 A1 | 7/2005 | Gorsuch et al. |
| 2005/0159771 A1 | 7/2005 | Petersen |
| 2005/0171561 A1 | 8/2005 | Songer et al. |
| 2005/0177249 A1 | 8/2005 | Kladakis et al. |
| 2005/0187508 A1 | 8/2005 | Gorsuch et al. |
| 2005/0209081 A1 | 9/2005 | Baugh et al. |
| 2005/0209556 A1 | 9/2005 | Tresco et al. |
| 2005/0209616 A1 | 9/2005 | Dongelmans |
| 2005/0214342 A1 | 9/2005 | Tweden et al. |
| 2005/0214344 A1 | 9/2005 | Barrows et al. |
| 2005/0215936 A1 | 9/2005 | Gorsuch et al. |
| 2005/0228432 A1 | 10/2005 | Hogendijk et al. |
| 2005/0236325 A1 | 10/2005 | Dolecek et al. |
| 2005/0236329 A1 | 10/2005 | Brotherton et al. |
| 2005/0240147 A1 | 10/2005 | Makower et al. |
| 2005/0240241 A1 | 10/2005 | Yun et al. |
| 2005/0251197 A1 | 11/2005 | Hensley et al. |
| 2005/0256028 A1 | 11/2005 | Yun et al. |
| 2005/0256540 A1 | 11/2005 | Silver et al. |
| 2005/0267516 A1 | 12/2005 | Soleimani et al. |
| 2005/0273123 A1 | 12/2005 | Dongelmans |
| 2006/0015137 A1 | 1/2006 | WasDyke et al. |
| 2006/0018799 A1 | 1/2006 | Wong et al. |
| 2006/0036279 A1 | 2/2006 | Eidenschink et al. |
| 2006/0036314 A1 | 2/2006 | Perez et al. |
| 2006/0041271 A1 | 2/2006 | Bosma et al. |
| 2006/0047301 A1 | 3/2006 | Ogle |
| 2006/0047333 A1 | 3/2006 | Tockman et al. |
| 2006/0076295 A1 | 4/2006 | Leonard et al. |

(56) References Cited

U.S. PATENT DOCUMENTS

| | | | |
|---|---|---|---|
| 2006/0079782 A1 | 4/2006 | Beach et al. | |
| 2006/0095068 A1 | 5/2006 | WasDyke et al. | |
| 2006/0293706 A1 | 12/2006 | Shimon | |
| 2007/0156211 A1* | 7/2007 | Ferren et al. | 607/101 |
| 2007/0260144 A1 | 11/2007 | Sela et al. | |
| 2008/0064957 A1* | 3/2008 | Spence | 600/439 |
| 2008/0065145 A1 | 3/2008 | Carpenter | |
| 2008/0140110 A1 | 6/2008 | Spence | |
| 2008/0255603 A1 | 10/2008 | Naor et al. | |
| 2008/0269871 A1 | 10/2008 | Eli | |
| 2009/0254172 A1 | 10/2009 | Grewe | |
| 2009/0281396 A1* | 11/2009 | Liao et al. | 600/301 |
| 2009/0287076 A1 | 11/2009 | Boyden et al. | |
| 2010/0106180 A1* | 4/2010 | Strother et al. | 606/200 |
| 2010/0168848 A1* | 7/2010 | Horvath et al. | 623/3.13 |
| 2010/0179585 A1 | 7/2010 | Carpenter et al. | |
| 2012/0259351 A1* | 10/2012 | Chak et al. | 606/159 |

FOREIGN PATENT DOCUMENTS

| | | |
|---|---|---|
| EP | 1 078 597 A2 | 2/2001 |
| EP | 1 357 481 A2 | 10/2003 |
| EP | 1 645 282 A1 | 4/2006 |
| EP | 0 293 605 A1 | 4/2008 |
| WO | WO 80/00779 | 5/1980 |
| WO | WO 91/08820 | 6/1991 |
| WO | WO 92/20428 | 11/1992 |
| WO | WO 93/12723 | 7/1993 |
| WO | WO 94/28996 | 12/1994 |
| WO | WO 96/18099 | 6/1996 |
| WO | WO 96/18745 | 6/1996 |
| WO | WO 96/39940 | 12/1996 |
| WO | WO 96/40857 | 12/1996 |
| WO | WO 97/27808 | 8/1997 |
| WO | WO 97/37591 | 10/1997 |
| WO | WO 97/42967 | 11/1997 |
| WO | WO 98/31732 | 7/1998 |
| WO | WO 98/57692 | 12/1998 |
| WO | WO 99/08596 | 2/1999 |
| WO | WO 99/08597 | 2/1999 |
| WO | WO 99/08598 | 2/1999 |
| WO | WO 99/11184 | 3/1999 |
| WO | WO 99/16362 | 4/1999 |
| WO | WO 99/27944 | 6/1999 |
| WO | WO 99/55360 | 11/1999 |
| WO | WO 99/60169 | 11/1999 |
| WO | WO 99/62614 | 12/1999 |
| WO | WO 00/44313 | 8/2000 |
| WO | WO 00/62891 | 10/2000 |
| WO | WO 00/66031 | 11/2000 |
| WO | WO 00/69429 | 11/2000 |
| WO | WO 01/10346 A1 | 2/2001 |
| WO | WO 01/49341 A2 | 7/2001 |
| WO | WO 01/67989 A2 | 9/2001 |
| WO | WO 01/92622 A1 | 12/2001 |
| WO | WO 02/41536 A1 | 5/2002 |
| WO | WO 02/43859 A2 | 6/2002 |
| WO | WO 02/056796 A1 | 7/2002 |
| WO | WO 02/077638 A2 | 10/2002 |
| WO | WO 02/080766 A2 | 10/2002 |
| WO | WO 02/089898 A1 | 11/2002 |
| WO | WO 02/098282 A2 | 12/2002 |
| WO | WO 03/047648 A2 | 6/2003 |
| WO | WO 03/096872 A2 | 11/2003 |
| WO | WO 2004/009158 A2 | 1/2004 |
| WO | WO 2004/012840 A2 | 2/2004 |
| WO | WO 2004/059293 A2 | 7/2004 |
| WO | WO 2004/082796 A2 | 9/2004 |
| WO | WO 2004/093965 A1 | 11/2004 |
| WO | WO 2004/096007 A2 | 11/2004 |
| WO | WO 2004/103162 A2 | 12/2004 |
| WO | WO 2004/110551 A2 | 12/2004 |
| WO | WO 2005/009508 A2 | 2/2005 |
| WO | WO 2005/011787 A2 | 2/2005 |
| WO | WO 2005/046528 A1 | 5/2005 |
| WO | WO 2005/046783 A1 | 5/2005 |
| WO | WO 2005/072648 A1 | 8/2005 |
| WO | WO 2005/094283 A2 | 10/2005 |
| WO | WO 2005/110494 A2 | 11/2005 |
| WO | WO 2005/122919 A2 | 12/2005 |
| WO | WO 2006/002283 A1 | 1/2006 |
| WO | WO 2006/011127 A2 | 2/2006 |
| WO | WO 2006/014699 A1 | 2/2006 |
| WO | WO 2006/020585 A1 | 2/2006 |
| WO | WO 2006/041855 A2 | 4/2006 |

OTHER PUBLICATIONS

Chen et al.; "3: Bifurcation Stenting"; Chapter 3: Bifurcation Stenting; pp. 27-49; printed on Mar. 7, 2012; located at: http://www.sis.org/docs/2006Yearbook_Ch3.pdf.

Hanna et al.; "Using a System-on-a-Chip Implantable Device to Filter Circulating Infected Cells in Blood or Lymph"; IEEE Transactions on Nanobioscience; Mar. 2003 and bearing a date of Jan. 25, 2003; pp. 6-13; vol. 2, No. 1; IEEE.

Purandare et al.; "Research: Cerebral Emboli as a Potential Cause of Alzheimer's Disease and Vascular Dementia: Case-Control Study"; BMJ Online First; bearing a date of Apr. 28, 2006; pp. 1-6; BMJ Publishing Group Ltd.

* cited by examiner

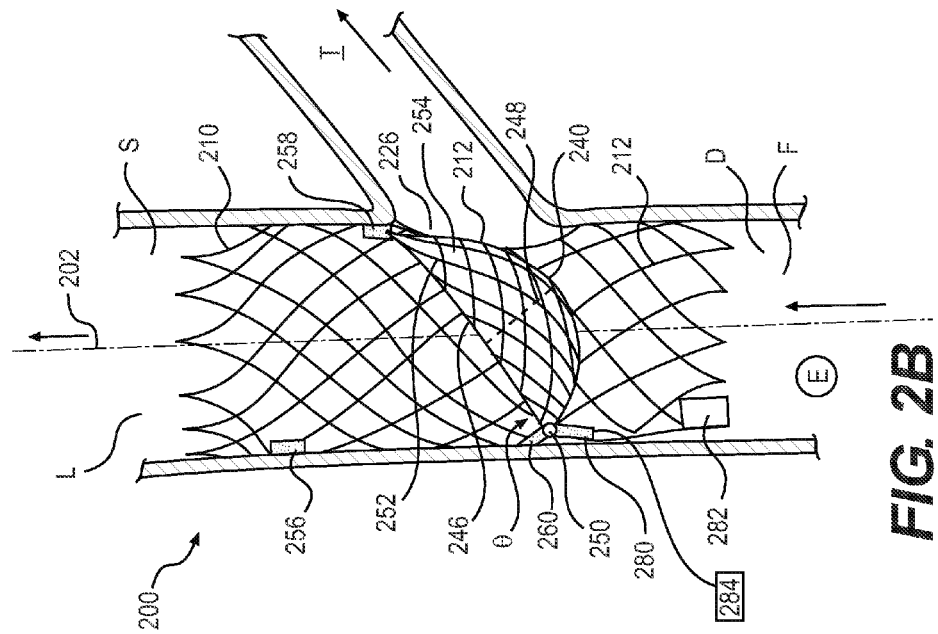

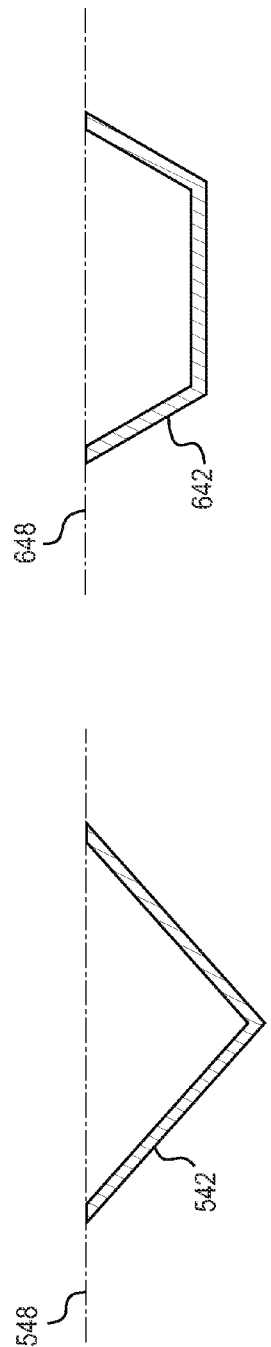
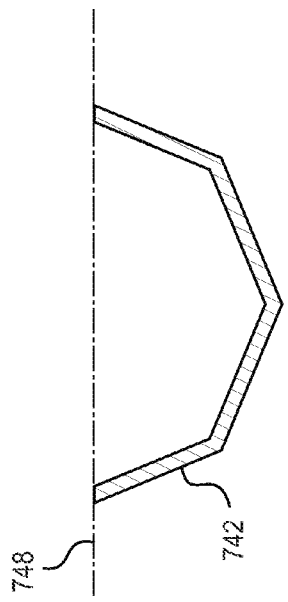

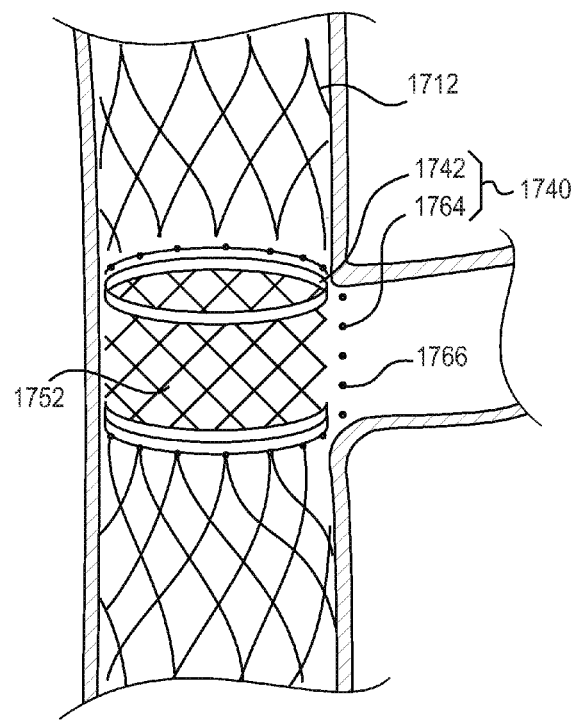
FIG. 17A
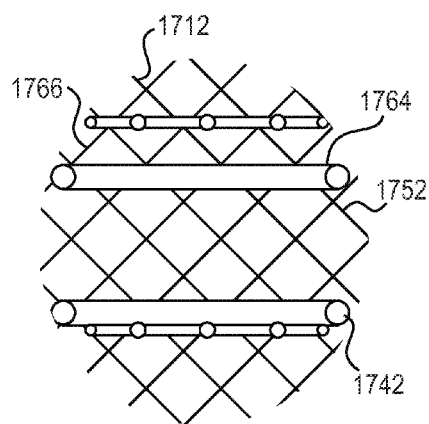 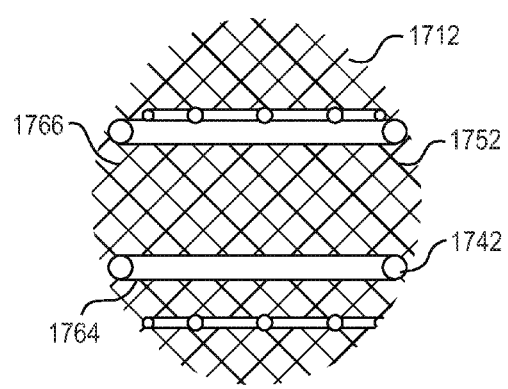
FIG. 17B　　　FIG. 17C

EMBOLISM DEFLECTOR

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None

RELATED APPLICATIONS

None

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, the present disclosure is directed to, among other things, systems, devices, and methods including an embolism deflecting device. In an aspect, the present disclosure is directed to, among other things, systems, devices, and methods for deflecting or diverting emboli away from critical locations in the body. In an embodiment, the embolism deflecting device comprises an embolism detector, a diverter controller operable for determining the presence of emboli from a target input from the embolism detector, and an embolism diverter operable by the diverter controller to deflect, divert, redirect, etc., emboli away from the critical body location on the detection thereof.

In an aspect, the present disclosure is directed to, among other things, systems, devices, and methods including an embolism deflecting device, comprising a support stent, an embolism detector, an embolism diverter, and at least one diverter controller. In an embodiment, the support stent includes a substantially tubular frame at least partially defining a lumen. In an embodiment, the substantially tubular frame has a first end in fluid communication with a second end through the lumen. The first end has an inlet to receive blood from a blood vessel. The second end has an outlet through which the blood exits the support stent. In an embodiment, the substantially tubular frame of the support stent has an anchor for removably securing at least a portion of the support stent in the blood vessel. The embolism detector includes an embolism sensor configured to detect an embolism in a detection field in the blood upstream of the blood vessel. The embolism detector includes a transmitter operable for transmitting information associated with a presence of detected emboli in the detection field. The embolism diverter includes one or more movable members movably secured to the substantially tubular support stent. In an embodiment, the one or more movable members are operable to direct a substantial portion of detected emboli of at least a target size in one of at least two directions. In an embodiment, the at least one diverter controller is operatively coupled to the embolism detector and to the embolism diverter. In an embodiment, the at least one diverter controller is operable for receiving information from the embolism detector and responsively moving at least one of the one or more movable members to a divert state, which is configured to divert a substantial fraction of detected emboli of at least a target size in one or more of the at least two directions.

In an embodiment, the second end of the support stent is bifurcated, the outlet of the second end including a first outlet through which blood exits the support stent into a second blood vessel, the second end further including a second outlet through which blood exits the support stent into a third blood vessel. In an embodiment, at least one of the one or more movable members of the embolism diverter at least partially overlaps an entrance of a second blood vessel in a non-divert state.

An embodiment further includes an implantable container coupled to the support stent, the implantable container in fluid communication with the blood vessel at least part of the time, the embolism diverter deflecting the substantial fraction of emboli into the implantable container when one or more movable members is in the divert state. In an embodiment, at least a portion of the implantable container is implantable outside of the blood vessel. In an embodiment, the implantable container is implantable substantially within the lumen of the blood vessel. In an embodiment, the implantable container is retrievable from the patient. In an embodiment, the implantable container further comprises a fill-level detector.

In an embodiment, each of the one or more movable members includes at least one of a valve, mesh, a screen, an obstructing member, a plurality of non-intersecting bars, or a spiral element. In an embodiment, the one or more movable members includes a flow diverter that in the divert state diverts blood flow away from a location. In an embodiment, the embolism diverter includes an elastically deformable flexible member, wherein a force applied to the flexible member causes the flexible member to undergo elastic deformation into the divert state, thereby diverting the substantial fraction of emboli in one or more of the at least two directions.

In an embodiment, the embolism diverter further comprises at least one fixed member, the at least one fixed member including at least one of a mesh, a screen, an obstructing member, a plurality of non-intersecting bars, or a spiral element, and in the divert state, at least a portion of the movable member overlaps at least a portion of the fixed member, the at least one of the mesh, screen, obstructing member, plurality of non-intersecting bars, or spiral element of the fixed member and the at least one of the mesh, screen, obstructing member, plurality of non-intersecting bars, or spiral element of the movable member together controlling a size of at least one opening dimensioned to divert a substantial fraction of emboli away from the more critical location. In an embodiment, in a non-divert state, the at least one of the mesh, screen, obstructing member, plurality of non-intersecting bars, or spiral element of the at least one fixed member and the at least one of the mesh, screen, obstructing member, plurality of non-intersecting bars, or spiral element of the one or more movable members separately do not define at least one opening dimensioned to divert a substantial fraction of emboli away from the more critical location. In an embodiment, the at least one fixed member extends across the lumen of the support stent. In an embodiment, the one or more movable members of the embolism diverter is at least one of rotated, translated, or pivoted relative to the at least one fixed member in a non-divert state compared with the divert state.

In an embodiment, the embolism diverter includes a plurality of movable members, each movable member including at least one of a mesh, a screen, an obstructing member, a plurality of non-intersecting bars, or a spiral element, and in the divert state, at least portions of the plurality of movable members overlap each other, the at least one of the mesh, screen, obstructing member, plurality of non-intersecting bars, or spiral element of the plurality of movable members together controlling a size of at least one opening dimensioned to direct a substantial fraction of emboli away from the more critical location. In an embodiment, in a non-divert state, the at least one of the mesh, screen, obstructing member, plurality of non-intersecting bars, or spiral element of the movable members separately do not define at least one opening dimensioned to divert a substantial fraction of emboli away from the more critical location. In an embodiment, the at least one movable member of the embolism diverter is at least one of rotated, translated, or pivoted relative to the at least one fixed member in the divert state compared with a non-divert state.

In an embodiment, the movable member of the embolism diverter includes at least one of a deflector surface, a ramp, a fin, or a rotatable snout having a first cross section in the non-divert state and a second cross section in the divert state. In an embodiment, movable member of the embolism diverter includes at least one of a rotating blade or a flow jet, the at least one of the rotating blade or the flow jet is activated at a first level in the non-divert state and activated at a second level in the divert state.

In an embodiment, the at least one movable member of the embolism diverter is substantially neutrally buoyant with respect to blood.

In an embodiment, the embolism diverter includes at least one latch. In an embodiment, the at least one latch includes at least one of a mechanical, spring, magnetic, solenoid actuated, piezoelectrically actuated, microelectromechanical system (MEMS) actuated, ferrofluid actuated, magnetorheological fluid actuated, electrorheological fluid actuated, or electromechanical latch.

In an embodiment, the embolism diverter is biased towards a flow direction. In an embodiment, the embolism diverter is biased by at least one of an elastic member, superelastic member, a spring, a live hinge, or a gas spring.

In an embodiment, the embolism diverter is operable by the diverter controller to move the at least one of the one or more movable members to a non-divert state. In an embodiment, an applied potential switches the embolism diverter between a non-divert state and divert state.

In an embodiment, the embolism diverter includes at least one actuator disposed between one or more movable members and the support stent, the actuator operatively coupled to the diverter controller and activatable thereby to urge the one or more movable members from a non-divert state to the divert state. In an embodiment, the at least one actuator is at least one of a MEMS actuator, an electromechanical actuator, a ferrofluid actuator, magnetorheological fluid actuator, electrorheological fluid actuator, a hydraulic actuator, a shape memory material actuator, piezoelectric actuator, or an electric motor.

In an embodiment, the diverter controller is operable to activate one or more actuators on receiving at least one parameter associated with the number of emboli, the embolism size, the embolism type, the embolism location, the embolism path, or the embolism arrival time, the one or more actuators disposed between the support stent and the one or more movable members, thereby converting the embolism diverter from a non-divert state to the divert state. In an embodiment, the diverter controller includes an external input for receiving external commands setting the state of the embolism diverter. In an embodiment, the diverter controller includes an external output for transmitting at least one of status, activity, embolism detector output, success of diversion, power status, or device history. In an embodiment, the diverter controller includes at least one of a processor, a microprocessor, a field programmable gate array, or an application-specific integrated circuit; a memory device; and a bus therebetween.

In an embodiment, the embolism detector is operable to determine at least one parameter associated with an emboli count, an embolism size, an embolism type, an embolism location, an embolism path, or an embolism arrival time. In an embodiment, the embolism detector is a first embolism detector, and the embolism deflecting device further comprises a second embolism detector operatively coupled to the diverter controller, the second embolism detector implantable with a detection field downstream of the embolism deflecting device. In an embodiment, the embolism detector includes at least one of an optical sensor or an ultrasonic sensor. In an embodiment, a detection field of the embolism detector is at least one of upstream of the embolism diverter or downstream of the embolism diverter.

In an embodiment, at least a portion of the support stent is implantable in at least one lumen of a first blood vessel, a second blood vessel, or a third blood vessel. In an embodiment, the support stent is at least one of self-expanding or balloon expandable. In an embodiment, the support stent includes at least one of an antithrombotic agent or an antiproliferative agent. In an embodiment, compared with the divert state, in a non-divert state, the embolism diverting device exhibits at least one of reduced damage to blood cells, reduced platelet activation, reduced turbulence, reduced drag, or reduced thrombogenesis. In an embodiment, at least a portion of the support stent is at least one of a shape memory material, a super elastic material, or nitinol.

In an embodiment, in the divert state, the embolism deflecting device consumes more power than in a non-divert state. In an embodiment, switching from a non-divert state to the divert state consumes energy.

In an embodiment, the embolism deflecting device is powered by at least one of blood flow, an energy storage device, a battery, a super capacitor, or an external power source. In an embodiment, the embolism deflecting device is powered by a power source including at least one of a thermoelectric generator, a piezoelectric generator, a microelectromechanical systems generator, or a biomechanical-energy harvesting generator. In an embodiment, the device is powered by a transcutaneous energy transfer system, the transcutaneous energy transfer system electromagnetically, magnetically, ultrasonically, optically, inductively, electrically, or capacitively-coupled to at least one of the embolism diverter or the diverter controller. In an embodiment, the at least one of an energy storage device, a battery, or a super capacitor is at least one of externally rechargeable or rechargeable by body movement.

In an embodiment, the embolism deflecting device includes at least one of stainless steel, nitinol, shape memory material, biocompatible polymer, polyester, polyamide, polytetrafluoroethylene, or copolymers or composites thereof.

In an embodiment, a kit includes an embolism deflecting device, and a percutaneous delivery system dimensioned to deliver the embolism diverting device to a desired location in a patient's vasculature. In an embodiment, the percutaneous delivery system includes an elongate guide catheter comprising a lumen, the guide catheter dimensioned for advancement through the patient's vasculature to the desired location, and an elongate device delivery catheter advanceable through the lumen of the guide catheter, the embolism deflecting device releasably mountable on a distal end of the device delivery catheter. In an embodiment, the device delivery catheter is a balloon catheter.

In an embodiment, an embolism deflecting device includes an embolism detector, a diverter controller, a support stent, and an embolism diverter. In an embodiment, the diverter controller is operable to determine a presence of at least one embolism in a detection field of the embolism detector based on a target input therefrom. In an embodiment, the support stent is dimensioned for deployment in a lumen of a blood vessel. In an embodiment, the embolism diverter is coupled to the support stent. In an embodiment, the embolism diverter includes at least one movable member. In an embodiment, the movable member is operable by the diverter controller to modulate the movable member between a non-divert position and a divert position based on a determination of the presence of at least one embolism by the diverter controller.

In an embodiment, an embolism deflecting device includes a diverter controller including an external input interface; a support stent dimensioned for deployment in a lumen of blood vessel; and an embolism diverter coupled to the support stent. In an embodiment, the embolism diverter includes at least one movable member. In an embodiment, the movable member is operable by the diverter controller to modulate the movable member between a non-divert position and a divert position in response to a signal received through the external input interface.

In an embodiment, a system for deflecting emboli includes an implantable embolism deflecting device and machine readable instructions readable by the processor of the diverter controller, that when executed by the processor, convert the movable member of the embolism diverter from the non-divert state to the divert state based on a target input. In an embodiment, the implantable embolism deflecting device includes an embolism detector, a diverter controller, a support stent, and an embolism diverter. In an embodiment, the embolism detector has an embolism detection field thereof upstream of the embolism diverter. In an embodiment, the embolism detector is operable for transmitting information associated with a presence or absence of an embolism in the detection field. In an embodiment, the diverter controller is operatively coupled to the embolism detector. In an embodiment, the diverter controller is operable for receiving the information associated with the presence of absence of an embolism in the detection field from the embolism detector. In an embodiment, the diverter controller includes a processor. In an embodiment, the support stent includes a substantially tubular frame substantially defining a lumen. In an embodiment, the substantially tubular frame has a first end in fluid communication with a second end through the lumen. In an embodiment, the first end has an inlet through which blood enters the support stent. In an embodiment, the second end has an outlet through which blood exits the support stent. In an embodiment, the substantially tubular frame of the support stent has an anchor for removably securing at least a portion of the support stent in the blood vessel. In an embodiment, the embolism diverter includes one or more movable members movably secured to the substantially tubular support stent. In an embodiment, the embolism diverter is coupled to the support stent. In an embodiment, the embolism diverter has at least one movable member movable from a non-divert state to a divert state. In an embodiment, the at least one movable member is operable to divert a substantial fraction of emboli of at least a target size in one of at least two directions. In an embodiment, the embolism diverter is operatively coupled to and controllable by the diverter controller to convert the movable member from the non-divert state to the divert state in response to a detection of an embolism in the detection field of the embolism detector.

In an embodiment, the diverter controller includes a memory device and a bus between the processor and the memory device, and the processor is at least one of a microprocessor, a field programmable gate array, or an application-specific integrated circuit.

In an embodiment, the target input is an external command. In an embodiment, the target input is an output from the embolism detector.

In an embodiment, the machine-readable instructions includes at least one of cryptographic protocol information, regulatory compliance protocol information, regulatory use protocol information, authentication protocol information, authorization protocol information, activation protocol information, encryption protocol information, and decryption protocol information.

In an embodiment, the diverter controller is operable to set the state of the embolism diverter according to at least one of type, location, size, presence, absence, time of passage, or route of an embolism, which is determined from the output of the embolism detector.

In an embodiment, the machine-readable instructions include characteristic spectral signature data that when compared with the output of the embolism detector, indicates the presence or absence of an embolism. In an embodiment, characteristic spectral signature data is refinable using the output of the embolism detector, thereby improving the accuracy of embolism detection.

An embodiment further includes machine readable instructions that when executed on the processor of the diverter controller, activate at least one of a Spectral Clustering protocol or a Spectral Learning protocol operable to compare one or more parameters associated with the output of the embolism detector with one or more information subsets associated with reference spectral signature data.

In an embodiment, the diverter controller includes one or more control embolism diverter parameters that are updatable based on data provided from a second embolism detector with a detection field downstream of the embolism diverter.

In an embodiment, the embolism deflecting device further includes a power source, and the target signal includes an energy level of the power source.

In an embodiment, the diverter controller is programmable.

In an embodiment, a method for deflecting an embolism in a patient includes repositioning at least one or more movable members of an embolism diverter, thereby converting the embolism diverter of an embolism deflecting device implanted in a lumen of a blood vessel from a non-divert state to a divert state in response a target input associated with detecting an embolism upstream of the embolism deflecting device. In the divert state, the embolism deflecting device diverts a substantial fraction of emboli of at least a target size in one of at least two directions.

An embodiment further includes deploying the embolism deflecting device in the lumen of the blood vessel. In an embodiment, the embolism deflecting device includes a support stent, an embolism detector, an embolism diverter, and at least one diverter controller. In an embodiment, the support stent includes a substantially tubular frame substantially defining a lumen. In an embodiment, the substantially tubular frame has a first end in fluid communication with a second end through the lumen. In an embodiment, the first end has an inlet through which blood enters the support stent. In an embodiment, the second end has an outlet through which blood exits the support stent. In an embodiment, the substantially tubular frame of the support stent has an anchor for removably securing at least a portion of the support stent in the blood vessel. In an embodiment, the embolism detector includes an embolism sensor configured to detect an embolism in a detection field in a blood stream. In an embodiment, the embolism detector includes a transmitter operable for transmitting information associated with a presence of emboli in the detection field. In an embodiment, the embolism diverter includes the one or more movable members movably secured to the substantially tubular support stent. In an embodiment, the at least one diverter controller is operatively coupled to the embolism detector and to the embolism diverter. In an embodiment, the at least one diverter controller is operable for receiving information from the embolism detector and responsively moving at least one of the one or more movable members to divert a substantial fraction of detected emboli of at least a target size in one or more of the at least two directions.

An embodiment further includes radially compressing the support stent of the embolism diverting device; securing the embolism diverting device to a percutaneous delivery system; positioning the embolism diverting device at a desired location in the lumen of the blood vessel; unsecuring the embolism diverting device from the percutaneous delivery system; and expanding the support stent of the embolism diverting device.

In an embodiment, deploying the embolism deflecting device in a lumen of a blood vessel includes deploying the embolism deflecting device at a bifurcation of a first blood vessel into a second blood vessel and a third blood vessel, the second blood vessel upstream of a more critical location and the third blood vessel upstream of a less critical location. In an embodiment, deploying the embolism deflecting device at a bifurcation of the first blood vessel into a second blood vessel and a third blood vessel includes deploying the embolism deflecting device at a bifurcation of at least one of a first vein into a second vein and a third vein; a first artery into a second artery and a third artery; a carotid artery into an internal carotid artery and an external carotid artery; an ascending aorta into a brachiocephalic artery and an arch of the aorta; or an arch of the aorta into a left common carotid artery and a descending aorta.

In an embodiment, deploying the embolism deflecting device includes deploying the embolism deflecting device including an implantable container, wherein the implantable container is the less critical location. An embodiment further includes monitoring a fill level of the implantable container; and replacing the implantable container.

In an embodiment, deploying the embolism deflecting device includes deploying the embolism deflecting device, wherein the diverter controller includes at least one of a processor, a microprocessor, a field programmable gate array, or an application-specific integrated circuit; a memory device; and a bus therebetween.

In an embodiment, repositioning at least one movable member of an embolism diverter includes at least one of translating, rotating, or pivoting the at least one movable member. In an embodiment, at least one of translating, rotating, or pivoting the at least one movable member includes at least one of translating, rotating, or pivoting the at least one movable member relative to a fixed member of the embolism diverter. In an embodiment, at least one of translating, rotating, or pivoting the at least one movable member includes at least one of translating, rotating, or pivoting the at least a first movable member relative to a second movable member.

In an embodiment, converting the embolism diverter from a non-divert state to a divert state includes converting the embolism diverter from a non-divert state to a divert state in response a target input including an external command. In an embodiment, converting the embolism diverter includes executing machine-readable instructions on the diverter controller, the machine readable instructions including at least one of cryptographic protocol information, regulatory compliance protocol information, regulatory use protocol information, authentication protocol information, authorization protocol information, activation protocol information, encryption protocol information, or decryption protocol information. In an embodiment, converting the embolism diverter includes the diverter controller setting the state of the embolism diverter according to at least one of type, location, size, presence, absence, time of passage, or route of an embolism, which is determined from the output of the embolism detector.

In an embodiment, detecting an embolism upstream of the embolism deflecting device includes comparing characteristic spectral signature data with the output of the embolism detector. In an embodiment, comparing characteristic spectral signature data with the output of the embolism detector further includes activating at least one of a Spectral Clustering protocol or a Spectral Learning protocol to compare one or more parameters associated with the output of the embolism detector with one or more information subsets associated with reference spectral signature data. An embodiment further includes refining characteristic spectral signature data using the output of the embolism detector, thereby improving the accuracy of embolism detection.

In an embodiment, converting a movable member of an embolism diverter of an embolism deflecting device implanted in a lumen of a first blood vessel upstream of a more critical location of a patient includes converting the movable member of the embolism diverter of the embolism deflecting device implanted upstream of a brain, a lung, or a heart of the patient.

In an embodiment, detecting an embolism upstream of the embolism diverting device includes detecting the embolism optically or ultrasonically.

An embodiment further includes monitoring downstream of the embolism deflecting device to determine the success of the embolism deflection.

An embodiment further includes converting the movable member from the divert state to the non-divert state.

In an embodiment, an article of manufacture includes a non-transitory signal-bearing medium bearing instructions that, when run on a processor, cause an embolism detector to determine one or more spectral parameters associated with an embolism present in a blood vessel; instructions that, when run on a processor, compare the one or more spectral parameters associated with an embolism present in a blood vessel to one or more information subsets associated with reference spectral signature data; and instructions that, when run on a processor, and in response to the comparison of spectral parameters, cause a diverter controller to modulate one or more movable members of an embolism diverter between a non-divert state and a divert state.

In an embodiment, a method of manufacturing an embolism diverting device includes coupling an embolism diverter including a movable member to a support stent dimensioned for implantation in a blood vessel; operatively coupling a diverter controller to the embolism diverter; and operatively coupling an implantable embolism detector to the diverter controller. In an embodiment, the movable member is movable from a non-divert state to a divert state. In an embodiment, the embolism diverter in the divert state dimensioned to divert a significant fraction of emboli of at least a target size in one of at least two directions. In an embodiment, the diverter controller converts the embolism diverter from the non-divert state to the divert state in response to a target input from the embolism detector indicating a presence of an embolism.

In an embodiment, the method includes manufacturing the support stent by laser cutting a hypotube. In an embodiment, the method includes manufacturing the diverter controller from at least one of a processor, a microprocessor, a field programmable gate array, or an application-specific integrated circuits; a memory device; and a bus therebetween. In an embodiment, the method includes writing characteristic spectral signature data on the memory device. In an embodiment, writing characteristic spectral signature data on the memory device further comprises writing at least one of a Spectral Clustering protocol or a Spectral Learning protocol on the memory device.

In an embodiment, an embolism deflecting device includes means for anchoring the embolism deflecting device in a lumen of a first blood vessel upstream of a more critical location in a patient; means for diverting an embolism coupled to the means for anchoring the embolism deflecting device; means for detecting an embolism upstream of the embolism deflecting device; and means for converting a state of the means for diverting the embolism from a non-divert state to the divert state in response to detection of an embolism by the means for detecting an embolism. In an embodiment, the means for diverting the embolism has a divert state deflecting a substantial fraction of emboli of at least a target size in one or at least two directions.

In an embodiment, the means for anchoring the embolism deflecting device includes a support stent. In an embodiment, the support stent includes at least one of a tubular frame having a first end first end having an inlet through which blood enters the support stent and a second end having an outlet through which blood exits the support stent; or a tubular frame having a first end having an inlet and a bifurcated second end having a first outlet and a second outlet. In an embodiment, the means for anchoring the embolism deflecting device includes at least one of a balloon expandable support stent or a self-expanding support stent. In an embodiment, the means for diverting an embolism includes an embolism diverter including at least one of at least one movable member, a repositioning of which converts the embolism diverter from the non-divert state into the divert state; at least one movable member, a repositioning of which relative to at least one fixed member converts the embolism diverter from the non-divert state into the divert state; or a first movable member, a repositioning of which relative to a second movable member converts the embolism diverter from the non-divert state into the divert state.

In an embodiment, the means for diverting an embolism includes an embolism diverter including at least one movable member, wherein the at least one movable member is at least one of translatable, rotatable, or pivotable. In an embodiment, the means for diverting an embolism includes an embolism diverter including at least one movable member, wherein the at least one movable member includes at least one of a mesh, a screen, an obstructing member, a plurality of non-intersecting bars, or a spiral element.

In an embodiment, the means for detecting an embolism includes at least one of an optical detector or an ultrasonic detector.

In an embodiment, the means for converting a state of the means for diverting the embolism from the non-divert state to the divert state includes a diverter controller having at least one of a processor, a microprocessor, a field programmable gate array, or an application-specific integrated circuit; a memory device; and a bus therebetween.

In an embodiment, a method includes modulating an embolism deflecting device having an embolism diverter between a non-divert state where the embolism diverter does not redirect a substantial fraction of emboli from away from a second blood vessel and into a third blood vessel, and a divert state where the embolism diverter redirects a substantial fraction of emboli away from the second blood vessel and into the third blood vessel.

In an embodiment, modulating the embolism deflecting device between the non-divert state and the divert state includes actuating a flexible member of an embolism deflecting device between a non-divert state where the flexible member does not redirect a substantial fraction of emboli from away from a second blood vessel and into a third blood vessel, and a divert state where an applied force to the flexible member causes the flexible member to undergo elastic deformation and to redirect a substantial fraction of emboli away from the second blood vessel and into the third blood vessel.

In an embodiment, an embolism deflecting device includes an embolism detector, a diverter controller, and an ultrasound emitter. In an embodiment, the embolism deflecting device is securable to a patient. In an embodiment, the embolism detector is securable to the patient with a detection field including a detection area in a blood vessel. In an embodiment, the embolism detector is operable for transmitting information indicating the presence of an embolism in the detection area. In an embodiment, the diverter controller is operatively coupled to the embolism detector. In an embodiment, the diverter controller is operable for receiving data from the embolism detector indicating the presence of the embolism in the detection area. In an embodiment, the ultrasound emitter is securable to the patient. In an embodiment, the ultrasound emitter is coupled to the diverter controller and operable thereby to activate the ultrasound emitter to direct ultrasound toward a target area in response to the presence of the embolism in the detection field. In an embodiment, the ultrasound is sufficient to steer a substantial fraction of emboli in one of at least two directions.

In an embodiment, the ultrasound emitter and the embolism detector are configurable to at least partially overlap the target area with the detection area. In an embodiment, ultrasound emitter and the embolism detector are configurable with the detection area upstream of the target area.

In an embodiment, the embolism detector, the diverter controller, and the ultrasound emitter are packaged together as a single unit.

In an embodiment, the embolism deflecting device includes at least one of stainless steel, nitinol, shape memory material, biocompatible polymer, polyester, polyamide, polytetrafluoroethylene, or copolymers or composites thereof.

In an embodiment, the embolism deflecting device further includes a container implantable in the patient to be in fluid communication with the blood vessel at least part of the time, and the ultrasound source is operable by the deflector controller to steer the substantial fraction of emboli into the implantable container. In an embodiment, at least a portion of the container is implantable outside of the blood vessel. In an embodiment, the container is implantable substantially within the lumen of the blood vessel. In an embodiment, the container is retrievable from the patient.

An embodiment further includes a substantially tubular stent implantable in the blood vessel. In an embodiment, the stent includes an inlet, an outlet, and a lumen fluidly connecting the inlet and the outlet. In an embodiment, the stent is collapsible to a first size suitable for percutaneous delivery to the first blood vessel and expandable to a second size suitable for anchoring the stent in the blood vessel. In an embodiment, the container is coupled to the tubular stent.

In an embodiment, the container further includes a fill-level detector. In an embodiment, the container includes at least one of a mesh and a screen.

In an embodiment, the ultrasound emitter is implantable proximate to the blood vessel. In an embodiment, the ultrasound emitter is implantable subcutaneously.

In an embodiment, the ultrasound emitter is releasably securable to a skin surface of the patient. In an embodiment, the ultrasound emitter is semi-permanently securable to the skin surface of the patient.

In an embodiment, the ultrasound emitter is a phase array ultrasound emitter. In an embodiment, the ultrasound is aimable by phase conjugation.

In an embodiment, the diverter controller is operable to activate the ultrasound emitter based on the at least one parameter associated with the number of emboli, the embolism size, the embolism type, the embolism location, the embolism path, or the embolism arrival time. In an embodiment, the diverter controller is operable to alter at least one control parameter of the ultrasound emitter based on the at least one parameter associated with the number of emboli, the embolism size, the embolism type, the embolism location, the embolism path, or the embolism arrival time.

In an embodiment, the embolism detector is a first embolism detector, and the diverter controller includes one or more control embolism diverter parameters that are updatable based on data provided from a second embolism detector coupled thereto, the second embolism detector securable to the patient with a detection field downstream of the embolism diverter.

In an embodiment, the diverter controller includes an external input for receiving external commands activating the ultrasound emitter. In an embodiment, the diverter controller includes an external output for transmitting at least one of status, activity, embolism detector output, success of steering the substantial fraction of emboli, power status, or device history.

In an embodiment, the diverter controller includes at least one of a processor, a microprocessor, a field programmable gate array, or an application-specific integrated circuit; a memory device; and a bus therebetween.

In an embodiment, the embolism detector and the ultrasound emitter are integrated.

In an embodiment, the embolism detector is operable to determine at least one parameter associated with a number of emboli, an embolism size, an embolism type, an embolism location, an embolism path, or an embolism arrival time.

In an embodiment, the embolism detector is a first embolism detector, and the embolism deflecting device further comprises a second embolism detector operatively coupled to the diverter controller. In an embodiment, the second embolism detector is implantable with a detection field downstream of the first embolism detector.

In an embodiment, the embolism detector includes at least one of an optical sensor or an ultrasonic sensor.

In an embodiment, the embolism detector is a phased array.

In an embodiment, in a divert state, the embolism deflecting device consumes more power when the ultrasound emitter is activated.

In an embodiment, an embolism deflecting device for deflecting an embolism away from a more critical location to a less critical location in a patient includes an embolism detector; a diverter controller operatively coupled to the embolism detector; and an ultrasound emitter operatively coupled to the diverter controller. In an embodiment, the embolism deflecting device is disposable relative to a patient with a detection area of the embolism detector in a portion of a vasculature upstream of a more critical location and a less critical location in a patient. In an embodiment, the diverter controller is operable for receiving data from the embolism detector and operable for determining the presence of the at least one embolism in the detection area therefrom. In an embodiment, the ultrasound emitter is activatable by the diverter controller to direct ultrasound towards a target location in the vasculature. In an embodiment, the ultrasound is sufficient to divert a substantial fraction of emboli away from the more critical location and towards the less critical location.

In an embodiment, a system for deflecting emboli includes an embolism deflecting device and machine readable instructions that when executed on the diverter controller, activate the ultrasound emitter based on a target input. In an embodiment, the embolism deflecting device includes an embolism detector, a diverter controller, and an ultrasound emitter. In an embodiment, the embolism detector is securable to a patient with a detection field including a detection area in a blood vessel. In an embodiment, the embolism detector is operable for transmitting data indicating the presence of an embolism in the detection area. In an embodiment, the diverter controller is operatively coupled to the embolism detector. In an embodiment, the diverter controller is operable for receiving data from the embolism detector indicating the presence of the embolism in the detection area. In an embodiment, the ultrasound emitter is securable to the patient. In an embodiment, the ultrasound emitter is coupled to the diverter controller and operable thereby to activate the ultrasound emitter to direct ultrasound toward a target area in response to the presence of the embolism in the detection field. In an embodiment, the ultrasound is sufficient to steer a substantial fraction of emboli in one of at least two directions.

In an embodiment, the diverter controller includes at least one of a processor, a microprocessor, a field programmable gate array, or an application-specific integrated circuit; a memory device; and a bus therebetween.

In an embodiment, the target input is an external command. In an embodiment, the target input is an output from an embolism detector.

In an embodiment, the machine-readable instructions includes at least one of cryptographic protocol information, regulatory compliance protocol information, regulatory use protocol information, authentication protocol information, authorization protocol information, activation protocol information, encryption protocol information, and decryption protocol information.

In an embodiment, the diverter controller is operable to activate or to deactivate the ultrasound emitter according to at least one of type, location, size, presence, absence, time of passage, or route of an embolism, which is determined from the output of the embolism detector. In an embodiment, the diverter controller is operable to control the ultrasound emitter according to at least one of type, location, size, presence, absence, time of passage, or route of an embolism, which is determined from the output of the embolism detector.

In an embodiment, the machine-readable instructions include characteristic spectral signature data that when compared with the output of the embolism detector, indicates the presence or absence of an embolism. In an embodiment, characteristic spectral signature data is refinable using the output of the embolism detector, thereby improving the accuracy of embolism detection.

An embodiment further includes machine readable instructions that when executed on the diverter controller, activate at least one of a Spectral Clustering protocol or a Spectral Learning protocol operable to compare one or more parameters associated with the output of the embolism detector with one or more information subsets associated with reference spectral signature data.

An embodiment further includes a power source, and the target signal includes an energy level of the power source.

In an embodiment, the embolism detector is a first embolism detector, and the system further includes a second embolism detector operatively coupled to the diverter controller. A detection field of the second embolism detector is downfield of the target area. In an embodiment, the target signal includes an output of the second embolism detector.

In an embodiment, a method for deflecting an embolism from a more critical location towards a less critical location in a patient includes activating an ultrasound emitter of an embolism deflecting device to direct ultrasound towards a target area of a blood vessel upstream of a more critical location and a less critical location in a patient. In an embodiment, the ultrasound is sufficient to steer a significant fraction of emboli away from the more critical location towards the less critical location in response to a target input indicating the presence of an embolism in or approaching the target area.

In an embodiment, the method includes securing the embolism deflecting device to the patient. In an embodiment, the embolism deflecting device further includes an embolism detector and a diverter controller. In an embodiment, the embolism detector has a detection field including or upstream of the target area. In an embodiment, the embolism detector is operable for transmitting data indicating the presence of the embolism in or approaching the target area. In an embodiment, the diverter controller is operatively coupled to the embolism detector. In an embodiment, the diverter controller is operable for receiving data from the embolism detector indicating the presence of the embolism in or approaching the target area and operable to activate the ultrasound emitter.

In an embodiment, the method includes securing the embolism detector and the ultrasonic emitter to the patient. In an embodiment, securing the embolism detector and the ultrasonic emitter to the patient includes at least one of implanting the embolism detector within the blood vessel, implanting the embolism detector proximate to the blood vessel, implanting the embolism detector subcutaneously, or securing the embolism detector to a skin surface of the patient. In an embodiment, securing the embolism detector and the ultrasonic emitter to the patient includes at least one of implanting the ultrasonic emitter proximate to the blood vessel, implanting the ultrasonic emitter subcutaneously, or securing the ultrasonic emitter to a skin surface of the patient. In an embodiment, securing the embolism detector and the ultrasonic emitter to the patient includes securing a single package including the embolism detector and the ultrasonic emitter to the patient.

In an embodiment, activating an ultrasound emitter of an embolism deflecting device to direct ultrasound towards the target area includes activating an ultrasound emitter of an embolism deflecting device to direct ultrasound towards a portion of a blood vessel. In an embodiment, the blood vessel is a first blood vessel bifurcating into a second blood vessel upstream of the more critical body part and a third blood vessel upstream of the less critical body part. In an embodiment, the ultrasound steers a significant fraction of emboli in the first blood vessel away from the second vessel and into the third blood vessel.

In an embodiment, steering a significant fraction of emboli in the target area away from the second vessel and into the third blood vessel includes steering a significant fraction of emboli in a first vein away from a second vein into a third vein; steering a significant fraction of emboli in a first artery away from a second artery into a third artery; steering a significant fraction of emboli in a carotid artery away from an internal carotid artery into an external carotid artery; steering a significant fraction of emboli in an ascending aorta away from a brachiocephalic artery into an arch of the aorta; or steering a significant fraction of emboli in an arch of the aorta away from a left common carotid artery into a descending aorta.

In an embodiment, activating an ultrasound emitter of an embolism deflecting device to direct ultrasound towards a target area includes activating an ultrasound emitter of an embolism deflecting device to direct ultrasound towards a portion of a blood vessel. In an embodiment, the embolism deflecting device further includes a container in fluid communication with the blood vessel. In an embodiment, the container is the less critical location. An embodiment further includes implanting the container in fluid communication with the blood vessel. An embodiment further includes monitoring a fill level of the container; and replacing the container.

In an embodiment, activating the ultrasound emitter includes activating a phase array ultrasound emitter. In an embodiment, activating the ultrasound emitter includes aiming the ultrasound by phase conjugation.

In an embodiment, activating the ultrasound emitter includes executing machine-readable instructions on the diverter controller, the machine readable instructions including at least one of cryptographic protocol information, regulatory compliance protocol information, regulatory use protocol information, authentication protocol information, authorization protocol information, activation protocol information, encryption protocol information, or decryption protocol information. In an embodiment, activating the ultrasound emitter includes the diverter controller activating the ultrasonic emitter according to at least one of type, location, size, presence, absence, time of passage, or route of an embolism, which is determined from the output of the embolism detector. In an embodiment, activating the ultrasound emitter includes causing the diverter controller to alter one or more operation parameters of the ultrasonic emitter according to at least one of type, location, size, presence, absence, time of passage, or route of an embolism, which is determined from the output of the embolism detector.

In an embodiment, detecting an embolism includes comparing characteristic spectral signature data with the output of the embolism detector. In an embodiment, comparing characteristic spectral signature data with the output of the embolism detector further includes activating at least one of a Spectral Clustering protocol or a Spectral Learning protocol to compare one or more parameters associated with the output of the embolism detector with one or more information subsets associated with reference spectral signature data. An embodiment further includes refining characteristic spectral signature data using the output of the embolism detector, thereby improving the accuracy of embolism detection.

In an embodiment, detecting the embolism includes detecting the embolism optically or ultrasonically. In an embodiment, detecting the embolism includes monitoring downstream of the target area to determine the success of the embolism deflection. An embodiment further includes at least one of imaging the blood vessel or activating the ultrasound emitter in the absence of an embolism to test the embolism deflecting device. An embodiment further includes monitoring the detection area during deflection. An embodiment further includes predicting a likelihood of emboli going towards less critical location or more critical location. An embodiment further includes generating a control signal to control the ultrasound emitter to affect the trajectory of the emboli towards less critical location. An embodiment further includes generating a control signal to control the ultrasound emitter to affect the trajectory of the emboli towards more critical location.

In an embodiment, a method for manufacturing an embolism diverting device includes operatively coupling an ultrasonic emitter to a diverter controller; and operatively coupling an embolism detector to the diverter controller. In an embodiment, the ultrasonic emitter and the embolism detector are securable to a patient. In an embodiment, the ultrasonic emitter is operable by the diverter controller to direct ultrasound towards a target area of a blood vessel in response to the presence of an embolism in a detection field of the embolism detector to steer a significant fraction of emboli away from a more critical location in a patient towards a less critical location.

In an embodiment, the method includes manufacturing the diverter controller from at least one of a processor, a microprocessor, a field programmable gate array, or an application-specific integrated circuits; a memory device; and a bus therebetween. In an embodiment, the method includes writing characteristic spectral signature data on the memory device. In an embodiment, writing characteristic spectral signature data on the memory device further comprises writing at least one of a Spectral Clustering protocol or a Spectral Learning protocol on the memory device.

In an embodiment, an embolism deflecting device includes means for detecting an embolism in a detection area of a blood vessel of a patient; means for steering a substantial fraction of emboli from the more critical location to the less critical location; and means activating the means for steering the substantial fraction of emboli in response to the detection of an embolism in the detection area. In an embodiment, the detection area is located upstream of a more critical location and a less critical location in the patient.

In an embodiment, the means for detecting an embolism includes at least one of an optical detector and an ultrasonic detector. In an embodiment, the means for steering a substantial fraction of emboli includes at least one of an ultrasound emitter, a phase array ultrasound emitter, or a phase conjugation ultrasound emitter. In an embodiment, the means activating the means for steering the substantial fraction of emboli includes a diverter controller having at least one of a processor, a microprocessor, a field programmable gate array, or an application-specific integrated circuit; a memory device; and a bus therebetween.

BRIEF DESCRIPTION OF THE FIGURES

FIGS. 2A and 2B are side cross-sectional views of an embodiment of an embolism deflecting device in a non-divert state and a divert state, respectively.

FIG. 5 is a top cross-sectional view of an embodiment of a movable member.

FIG. 6 is a top cross-sectional view of an embodiment of a movable member.

FIG. 7 is a top cross-sectional view of an embodiment of a movable member.

FIG. 17A is a side cross-sectional view of an embodiment of a frame, movable member, and fixed member in a non-divert state.

FIGS. 17B and 17C are detail views of the movable member, and fixed member in a non-divert state and a divert state, respectively.

DETAILED DESCRIPTION

Figure 1A:
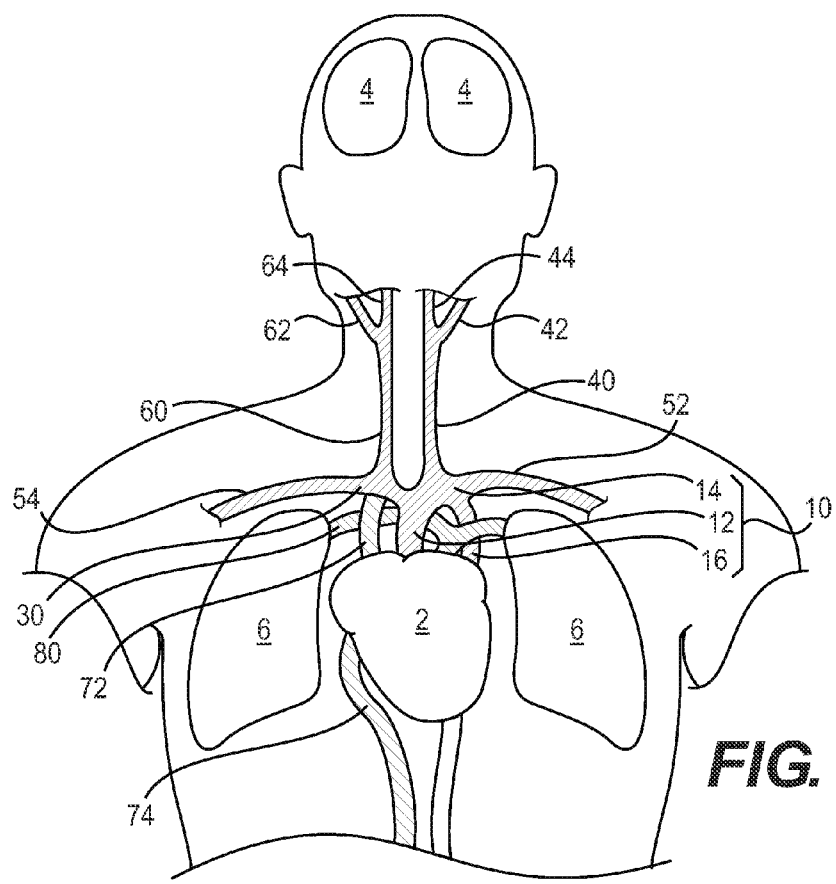
FIG. 1A is front cross-sectional diagram of a head and thorax of a patient showing a portion of the vasculature and major organs.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Cardiovascular disorders are a leading cause of death and disability in the United States. See, e.g., Heron et al., *Deaths: Preliminary Data for* 2006, *National Vital Statistics Report,* 56(16) Table B (2008). A number of those cardiovascular disorders are associated with the formation of intravascular obstructions including, for example, embolism, thrombosis, infarction, and ischemia. An embolism generally involves an obstruction or an occlusion of a vessel (e.g., a body fluid vessel, a blood vessel) by an object (i.e., an embolus). The object (e.g., a mass, a gas bubble, a detached blood clot, a blood component aggregate, a clump of bacteria, a foreign body, plaque, or the like, or other material or substance) migrates from one part of the body through, for example, circulation and causes a blockage (e.g., occlusion) of a blood vessel in another part of the body. Thrombosis generally involves an obstruction or an occlusion of a vessel by the formation of a thrombus or blood clot at the blockage point within a blood vessel, which can shed emboli as portions break off. Embolism can contribute to the morbidity of many health problems, including stroke, heart attack, pulmonary embolism, and complications of cancer.

While an occlusion of any blood vessel can cause a loss of certain function in a person, blocking a portion of or substantially all of the blood flow to certain, more critical body locations are associated with more severe consequences. For example, an embolism in a blood vessel supplying the brain can cause a stroke, an embolism in a coronary artery can cause a heart attack, and an embolism in an artery in a lung can cause a pulmonary embolism. Each of these events can lead to permanent, severe disability or even death. See, e.g., S. Blum, et al., *Neurology,* 78, 38 (2012) (stroke causing memory loss); N. Purandare, et al., BMJ, doi:10.1136/bmj.38814.696493.AE (published 28 Apr. 2006) (cerebral emboli potentially causing Alzheimer's and dementia). Moreover, certain parts of the body are vascularized by a plurality of sources. Consequently, blocking one source might result in little or no loss in function.

As a non-limiting example, certain systems, devices, and methods, described herein provide an embolism deflecting device configured for, for example, actively sensing, treating, or preventing an occlusion (e.g., an embolus, or the like), a hematological abnormality, a body fluid flow abnormality, or the like. As a non-limiting example, certain systems, devices, and methods, described herein provide technologies or methodologies for actively sensing, treating, or preventing an intravascular obstruction.

Figure 1B:
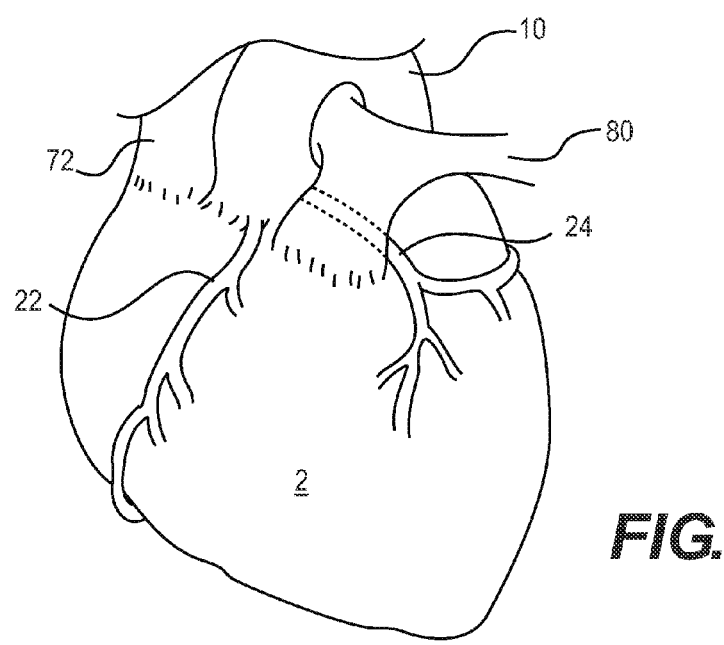
FIG. 1B is a front view diagram of a heart.

FIG. 1A schematically illustrates a portion of the cardiovascular system, including a heart 2. Oxygenated blood is pumped out the heart 2 into a person's body through an aorta 10, which comprises an ascending aorta 12, an aortic arch 14, and a descending aorta 16. As shown in FIG. 1B, a right coronary artery 22 and a left coronary artery 24 branch from the ascending aorta 12, and supply oxygenated blood to the heart 2. Returning to FIG. 1A, originating from the aortic arch 14 are a brachiocephalic artery 30, a left common carotid artery 40, and a left subclavian artery 52. The brachiocephalic artery 30 bifurcates into a right subclavian artery 54 and a right common carotid artery 60. The left and right subclavian arteries principally supply blood to a person's left and right arms, respectively.

The left common carotid artery 40 and the right common carotid artery 60 each bifurcate into an external carotid artery 42 and 62, and an internal carotid artery 44 and 64. The external carotid arteries 42 and 62 supply blood to a person's neck and face. The internal carotid arteries 44 and 64 supply blood to the brain 4.

Deoxygenated blood returns to the heart 2 from an upper part of the body through a superior vena cava 72, and from a lower part of the body through an inferior vena cava 74. The deoxygenated blood is pumped into the lungs 6 through pulmonary arteries 80.

Emboli entering a blood vessel upstream of a critical body location or system, for example, the heart 2, the brain 4, or the lungs 6, can block blood flow to the critical body location, thereby causing a potentially devastating blood vessel occlusion. Examples of potentially grave blood vessel occlusions include a stroke or myocardial infarction. Consequently, deflecting emboli away from blood vessels supplying one or more critical body locations or systems can reduce the likelihood of occlusions therein. For example, deflecting emboli away from the coronary arteries 22 and 24. Deflecting emboli away from the brachiocephalic artery 30, the left 40 and right 60 common carotid arteries, or the internal carotid arteries 44 and 64 can reduce the likelihood of stroke in the brain 4. Deflecting emboli away from the superior 72 or inferior 74 vena cava can reduce the likelihood of pulmonary embolism by preventing the heart from pumping any emboli entering through either vena cava into the pulmonary arteries. Some patients are disposed to developing deep venous thrombosis (DVTs) in their lower extremities, which are susceptible to shedding emboli into the inferior vena cava 74 resulting in pulmonary embolism. In these patients, deflecting emboli from the inferior vena cava 74 can be life-saving. In an embodiment, emboli are deflected away from other blood vessels or body locations, systems, or organs.

In some cases, however, emboli deflected away from a first critical location can endanger a second critical location. For example, in an embodiment, emboli deflected away from the coronary arteries, thereby protecting the heart 2, travel into the aortic arch 14 where they can enter the brachiocephalic artery 30 or right common carotid artery 60, thereby endangering the brain 4. Consequently, in an embodiment, emboli deflected away from a critical location are directed to a less critical location. For example, in an embodiment, emboli are deflected away from an internal carotid artery 44 or 64, which supplies blood to the brain 4, to the corresponding external carotid artery 42 or 62, which supplies blood to the neck and face. While a blood vessel occlusion in the neck or face is a negative outcome, it is preferable to a stroke in the brain 4.

In an embodiment, an embolism deflecting device is capable of deflecting a least a significant fraction of emboli from a more critical location in a patient to a less critical location in a patient, thereby reducing the likelihood of a blood vessel occlusion in the more critical location. In an embodiment, the deflected emboli have target sizes or diameters larger than about 10 mm, larger than about 8 mm, larger than about 6 mm, larger than about 5 mm, larger than about 4 mm, larger than about 2 mm, or larger than about 1 mm.

FIG. 2A is a cross-sectional front view of an embodiment of an embolism deflecting device 200 in a non-divert state, while FIG. 2B illustrates the embolism deflecting device in a divert state. In an embodiment, the embolism deflecting device 200 comprises a longitudinal axis 202, a support stent 210, an embolism diverter 240, a diverter controller 280, and an embolism detector 282.

In the illustrated embodiment, at least a portion of the embolism deflecting device 200 is implantable in the lumen L of a blood vessel upstream of the more critical location in the patient. In an embodiment, the embolism deflecting device 200 is implantable at a bifurcation or branch B of a first blood vessel F into a second blood vessel S and a third blood vessel T, where the second blood vessel S is upstream of the more critical body part and the third blood vessel T is upstream of the less critical body part, as discussed above. The direction of blood flow from the first blood vessel F into the second blood vessel S and the third blood vessel T is indicated by arrows in FIG. 2A. In an embodiment, the first blood vessel F is one of a first vein, a first artery, a carotid artery, an ascending aorta, or an arch of the aorta; the second blood vessel S is one of a second vein, a second artery, an internal carotid artery, a brachiocephalic artery, or a left common carotid artery, respectively; and the third blood vessel T is one of a third vein, a third artery, an external carotid artery, the arch of the aorta, or a descending aorta, respectively.

The illustrated embodiment of the embolism deflecting device 200 is generally suitable for situations in which the first blood vessel F and second blood vessel S are generally collinear, coaxial, or continuous and the third blood vessel T branches off, for example, where a carotid artery is the first blood vessel, the internal carotid artery is the second blood vessel, and the external carotid artery is the third blood vessel. It is contemplated that the device 200 and other embodiments described herein are adaptable to a range of vascular arrangements, for example, where the first F and third T blood vessels are generally continuous and the second blood vessel S is a branch.

In an embodiment, the support stent 210 includes a tubular, mesh-like frame 212 defining a lumen 214. In an embodiment, the tubular frame 212 has a first or inlet end 216 configured to be in fluid communication with a second or outlet end 218 through the lumen 214. In an embodiment, the first end 216 has an inlet 220 through which blood enters the support stent 210, and the second end 218 has an outlet 222 through which blood exits the support stent 210. In an embodiment, the frame 212 of the support stent has a delivery configuration with a first diameter dimensioned for minimally invasive delivery of the embolism deflecting device 200 into the vasculature of a patient, and an expanded configuration with a second diameter greater than the first diameter, where the frame 212 of the support stent in the expanded configuration is dimensioned to anchor at least a portion of the support stent 210 in the blood vessel upstream of a more critical location in a patient. In an embodiment, at least a portion of the device 200 is deliverable percutaneously, for example, through a femoral artery, a brachial artery, or a femoral vein. In an embodiment at least a portion of the device 200 is deliverable transapically through a patient's heart, for example, into the aorta, pulmonary artery, inferior vena cava, or superior vena cava. In an embodiment, at least a portion of the device 200 is implanted surgically.

In an embodiment, the embolism diverter 240 is coupled to the support stent 210 in the illustrated embodiment. In an embodiment, the embolism diverter 240 has at least one movable member 242, which is repositionable to convert the embolism diverter 240 from a non-divert state to a divert state. In the illustrated embodiment, the at least one movable member 242 includes at least one surface 244 dimensioned to direct a substantial fraction of emboli E larger than a target size in one of at least two directions. As discussed above, a first direction leads to the more critical location and a second direction leads to the less critical location. As discussed above, an embodiment includes additional directions, for example, towards a second more critical location. As shown in FIG. 2B, the at least one movable member 242 directs emboli E away from the more critical location and to the less critical location through the third blood vessel T in the divert state. In an embodiment, the embolism diverter 240 is operatively coupled to and controllable by the diverter controller 280 to convert the embolism diverter from the non-divert state (FIG. 2A) to the divert state (FIG. 2B) in response to a detection of an embolism E in a detection field D of the embolism detector 282, discussed in greater detail below.

In an embodiment, the diverter controller 280 is operatively coupled to the embolism detector 282, and is operable for receiving data or information from the embolism detector 282 indicating the presence of an embolism E in the detection field. In the illustrated embodiment, the support stent 210 supports the diverter controller 280.

In an embodiment, the embolism detector 282 is disposable relative to the patient with a detection field D of the embolism detector 282 upstream of the embolism diverter 240. In an embodiment, the embolism detector 282 is operable for transmitting data indicating or information related to a presence of an embolism E in the detection field D.

In an embodiment, the embolism deflecting device 200 comprises any suitable material, for example, metal, polymer, ceramic, and combinations thereof. Portions of the device 200 exposed to a patient's body comprise one or more biocompatible materials, for example, stainless steel, titanium, nitinol, gold, biocompatible polymers, biocompatible ceramics, stainless steel, nitinol, shape memory material, biocompatible polymer, polyester, polyamide, polytetrafluoroethylene, polyalkenes, polyethylene, ultra-high molecular weight polyethylene, copolymers or composites thereof, and the like.

In an embodiment, the embolism deflecting device 200 comprises one or more expandable components. For example, in an embodiment, the tubular frame 212 of the support stent is self-expanding, balloon expandable, or both. In an embodiment, the self-expanding components, for example, the frame 212, comprises one or more shape memory materials, for example, nitinol, iron-based shape memory alloys, other shape memory alloys, shape memory ceramics, shape memory polymers, or super elastic materials.

In an embodiment, at least a portion of the embolism deflecting device 200 includes a desired amount of an antithrombotic agent or an antiproliferative agent, which prevents clot formation and endothelial cell growth on the treated portion, for example, a moving part or a part that releasably engages another part. In an embodiment, at least a portion of the embolism deflecting device 200 is coated with the antithrombotic agent or an antiproliferative agent, for example, in a polymer matrix. Examples of suitable antithrombotic and antiproliferative agents include: placlitaxel, sirolimus rapamycin, zotarolimus, everolimus, umirolimus, hirudin, prostacyclin, iloprost, tamibarotene, retinobenzoic acid, glycoprotein (GP) IIb/IIIa inhibitors, urokinase, angiopeptin, somatostatin. In an embodiment, the antithrombotic agent or an antiproliferative agent is elutable from the polymer matrix. In an embodiment, the polymer matrix is erodible, for example, polylactic acid, polyglycolic acid, lactic acid-glycolic acid copolymers, polycaprolactone, poly(hydroxybutyrate), phosphorylcholine, polyethylene glycol, gelatin, and derivatives, blends, mixtures, and copolymers thereof. An embodiment of the embolism deflecting device 200 includes a reservoir in which the antithrombotic agent or an antiproliferative agent is disposed. For example, in an embodiment, the antithrombotic agent or an antiproliferative agent is disposed in pits, depressions, or hollow portions of the embolism deflecting device, disposed, for example, in the support stent 210 or movable member 242.

In the illustrated embodiment, the second end 218 of the support stent can be extended into a significant portion in the second blood vessel S. In an embodiment, the second end 218 of the support stent 210 can be bifurcated, such that the outlet 222 of the second end includes a first outlet through which blood exits the support stent 210 into the second blood vessel S, and a second outlet through which blood exits the support stent into the third blood vessel T. Consequently, portions of the support stent 210 can be implanted in the lumens of the first blood vessel F, the second blood vessel S, and the third blood vessel T. In an embodiment, portions of the support stent 210 are implantable in other combinations of the first blood vessel F, the second blood vessel S, and the third blood vessel T, for example, in any two of the three, or in only one of the three blood vessels. The particular configuration can be selected, for example, according to factors including the anatomy of the branch or bifurcation B, whether the second blood vessel S or the third blood vessel T is generally collinear or continuous with the first blood vessel F, the accessibility of the implant location, the method for implantation, the anticipated hydrodynamic forces to which the device 200 will be subjected, other forces on the device 200, the particular design of the device 200, and the like. Furthermore, the tubular frame 212 in the illustrated embodiment is generally straight. In an embodiment, the tubular frame 212 is sufficiently flexible to accommodate curves in the vasculature. In an embodiment, at least a portion of the frame is curved or bent in an unconstrained expanded state to conform to a particular anatomy.

In an embodiment, the frame 212 comprises frame members 224 in the form of a mesh, web, interlocking links, rings, bars, or combinations thereof. In the illustrated embodiment, the frame members 224 define a mesh. In the illustrated embodiment, an open area 226 of the frame at the bifurcation B with the third blood vessel T is sufficiently open to permit emboli E to enter the third blood vessel T. In an embodiment, the open area 224 is an opening through the frame 212 unobstructed by any frame members 224. In an embodiment, the open area 226 encompasses one or more frame members 224, for example, which help maintain the structural integrity of the frame 212. In an embodiment, the open area 226 can be larger than a typical inlet for the third blood vessel T, thereby permitting the device 200 to accommodate a range of patients. In an embodiment, the open area can be extended around the frame 212, to allow some angular leeway in placing the device 200. In an embodiment of the frame 212, the open area 226 encompasses substantially the entire frame 212, that is, the entire frame 212 has a generally open structure with the frame members 224 defining large openings therebetween.

In an embodiment, the support stent 21 or embolism diverter 240 comprises alignment or positioning elements. For example, in an embodiment, the support stent 21 or embolism diverter 240 comprises one or more radiopaque markers or ultrasound reflectors that assist in longitudinally or rotationally aligning the movable member 242 or open area 226 with the opening of the third blood vessel T.

In an embodiment, the support stent 210 can be manufactured by any suitable method, for example, molding, machining, water jet machining, laser machining, laser cutting, welding, laser welding, swaging, sewing, suturing, mechanical fastening, 3-D printing, gluing, and combinations thereof. In an embodiment, the support stent 210, and optionally, other portions of the embolism deflecting device 200 exposed to the patient's blood stream, exhibit at least one of reduced damage to blood cells, reduced platelet activation, reduced turbulence, reduced drag, or reduced thrombogenesis.

In the illustrated embodiment, the movable member 242 of the embolism diverter 240 is generally oval with a longer axis 246 generally parallel to the longitudinal axis 202 of the embolism deflecting device in the non-divert state illustrated in FIG. 2A, and a shorter axis 248 generally transverse to the longer axis 246. As shown in FIG. 2B, the movable member 242 in the divert state is dimensioned to be positioned substantially across the lumen 214 of the support stent, thereby directing emboli E larger than a target size into the third blood vessel T. As such, a ratio between the lengths of the longer axis 246 and shorter axis 248 depends on an angle θ between the oval movable member 242 and the frame 212 of the support stent, with smaller angles correlated with larger ratios as would be apparent to those skilled in the art. In an embodiment, the angle θ is from about 20° to about 70°, or from about 30° to about 60°, or from about 40° to about 50°. In the illustrated embodiment, the movable member 242 is slightly undersized compared to the cross-sectional area of the lumen, thereby permitting the movable member 242 to freely move between the divert and non-divert states over a range of stent 210 diameters, for example, resulting from the support stent 210 expanding to fit a range of diameters of blood-vessel lumens L. In an embodiment, any gaps between the movable member 242 and tubular frame 212 are sufficiently small to prevent a significant number of emboli larger than a target size from entering the second blood vessel S in the divert state.

As shown in FIG. 2A, the movable member 242 in the illustrated embodiment is curved along the direction of the minor access 248 to generally match a curvature in the frame 212 of the support stent. Consequently, in the non-divert state, the movable member 242 nests against the frame 212 of the support stent. In an embodiment, the support stent 210 can be generally cylindrical and the movable member 242 can be generally shaped like a section of a cylinder. In an embodiment in which the support stent 210 has a different shape, the movable member 242 is shaped to generally nest within the support stent 210. In an embodiment, the movable member 242 is not nested against the frame 212 of the support stent. In an embodiment in which the movable member 242 does not nest against the frame 212, at least a portion of the movable member 242 extends at least partially across the lumen of the second blood vessel S in the non-divert state.

As shown in FIG. 2A, the embolism diverter 240 can include a coupling member 250 flexibly coupling the movable member 242 to the support stent 210. In the illustrated embodiment of FIG. 2B, the coupling member 250 comprises a hinge coupling an inlet end of the movable member 242 to an inner wall of the stent 210 at a position proximate the first end 216 of the support stent, such that in the divert state, a portion of an outlet end of the movable member 242 extends into third blood vessel T, thereby defining a pathway for emboli E into the third blood vessel T. The hinge can be of any suitable type. In an embodiment, the hinge includes at least two relatively movable pieces, for example, a barrel hinge, or a butt hinge. In an embodiment, the hinge is elastically deformable, for example, a live hinge. In an embodiment, the coupling member 250 biases the movable member 242 towards one of the non-divert state or the divert state. In an embodiment, the coupling member 250 comprises least one of an elastic member, a superelastic member, a spring, a live hinge, or a gas spring that bias the movable member 242.

Live hinges are examples of an embodiment in which the coupling member 250 is a flexible member. An elastic deformation of the live hinge transforms the embolism diverter 240 between the divert state and non-divert state.

In the illustrated embodiment of FIG. 2A, the movable member 242 of the embolism diverter permits blood flow therethrough in the divert state, while blocking emboli E larger than a target size and diverting the emboli E into the third blood vessel T. In an embodiment, the movable member 242 includes at least one blocking member 252 that defines the surface 244, and defines at least one aperture 254 dimensioned to block emboli larger than the target size from passing therethrough. In an embodiment, the at least one blocking member 252 includes at least one of a mesh, a screen, an obstructing member, a plurality of non-intersecting bars, or a spiral element. In the illustrated embodiment, the at least one blocking member 252 is in the form of a mesh or net.

In an embodiment, at least some or a portion of the blocking members 252 are elastomeric or elastically deformable, endowing the surface 244 with a "trampoline" or "catapult" effect that projects emboli E into the third blood vessel when the embolism diverter 240 is in the divert state. In an embodiment, the elastomeric or elastically deformable blocking members 252 are deformable by the force of emboli B contact therewith. In an embodiment, the elastomeric or elastically deformable blocking members 252 are deformable by pulsatile blood flow. In an embodiment, the elastomeric or elastically deformable blocking members 252 deform during systole and return to their relaxed states during diastole, thereby actively "projecting" any emboli E incident thereto into the third blood vessel T. In an embodiment, the surface 244 is a driven oscillator, which actively "shakes" emboli E into the third blood vessel, driven, for example, by cycling an actuator 260 coupled to the movable member 242.

In an embodiment, the movable member 242 can be made to be substantially neutrally buoyant with respect to blood. In an embodiment, the movable member 242 has a low drag coefficient $c_d$.

The embodiment illustrated in FIGS. 2A and 2B also includes a first latch 256, that engages and secures the movable member 242, releasably coupling the movable member 242 to the frame 212 in the non-divert state. A second latch 258 engages and secures the movable member 242, releasably coupling the movable member to the frame 212 in the divert state. In the illustrated embodiment, the first latch 256 and second latch 258 can be, for example, magnetic latches. In an embodiment, the latches 256 and 258 are operatively coupled to the controller 280, which is discussed in greater detail below. In an embodiment, the first latch 256 and the second latch 258 are of any suitable type, for example, selected from mechanical, spring, magnetic, solenoid actuated, piezoeletrically actuated, MEMS actuated, ferrofluid actuated, magnetorheological fluid actuated, electrorheological fluid actuated, or electromechanical latches. In an embodiment, at least one of the first latch 256 or the second latch 258 accommodates misalignment between the frame 212 and the movable member 242. In an embodiment, comprise only one of the first latch 256 or the second latch 258 is provided. In an embodiment, a latch is not provided.

In the embodiment shown in FIGS. 2A and 2B, the embolism diverter 240 includes at least one actuator 260, which moves the movable member 242 from the non-divert state to the divert state, and optionally, from the divert state to the non-divert state. In an embodiment, the actuator 260 is coupled to the movable member 242 and tubular frame 212 or support stent 210. In an embodiment, the actuator 260 is disposed proximate to the coupling member 250, thereby converting a small movement of the actuator 260 into a large movement of the movable member 242. The actuator 260 is any suitable type, for example, a MEMS actuator, an electromechanical actuator, a ferrofluid actuator, magnetorheological fluid actuator, electrorheological fluid actuator, a hydraulic actuator, a shape memory material actuator, piezoelectric actuator, or an electric motor. In an embodiment, the actuator 260 includes a first sub-actuator that converts the embolism diverter 240 into the divert state and a second sub-actuator that converts the embolism diverter 240 into the non-divert state.

In an embodiment, the embolism diverter 240 does not employ an actuator when changing into at least one of the divert state or non-divert state. For example, as discussed above, in an embodiment, the movable member 242 is biased towards one of the divert state or non-divert state, and consequently, in an embodiment does not use an actuator for conversion to the biased-towards state. In an embodiment, for example, ordinary antegrade blood flow or increased blood flow during systole, moves the movable member 242 into the divert state or non-divert state. For example, in the illustrated embodiment, blood flow pushes the movable member 242 towards the non-divert state. In an embodiment, the first latch 256 or second latch 258 maintains the embolism diverter 240 in the divert state or non-divert state.

In the embodiment illustrated in FIGS. 2A and 2B, the actuator 260 is coupled to the coupling member 250, which can be a live hinge including a shape memory material, for example, nitinol, with an austenite finish temperature $A_f$ slightly higher than physiological temperature. At physiological temperature, the coupling member 250/actuator 260 has a low-temperature memory shape for the non-divert state, and a high temperature memory shape for the divert state. In an embodiment, the transition takes place when the shape memory material is heated above $A_f$, for example, resistively heated by passing a current therethrough. In an embodiment, a separate heater, for example, a resistive heating element disposed proximate to the shape-memory-material live hinge is included. In the illustrated embodiment, the second latch 258 holds the movable member 242 in the divert state. In an embodiment, the shape memory material may not need to be heated to maintain the movable member 242 in the divert state.

In an embodiment, the movable member 242 can be expandable, for example, self-expandable or mechanically expandable, for example, using a balloon or other device. In an embodiment, mechanically expandable movable members 242 are secured to the tubular frame 212 during deployment and expanded together, after which, the securements between the movable member 242 and frame 212 are released.

In an embodiment, the diverter controller 280 converts the embolism diverter 240 from the non-divert state to the divert state, and optionally, from the divert state back to the non-divert state. In an embodiment, the diverter controller 280 comprises at least one of a processor, a microprocessor, a field programmable gate array, or an application-specific integrated circuit; a memory device; and a bus therebetween. In an embodiment, the diverter controller 280 is operatively coupled to the at least one actuator 260, controlling the state thereof, and consequently, the state of the embolism diverter 240. In an embodiment, the diverter controller 280 is also operatively coupled to the first latch 256 and second latch 258.

In an embodiment, the diverter controller 280 converts the embolism diverter from the non-divert state to the divert state based on the at least one parameter associated with the number of emboli including, for example, the embolism size, the embolism type, the embolism location, the embolism path, or the embolism arrival time. In an embodiment, at least a portion of the diverter controller 280 is disposed on the support stent 210. In an embodiment, at least some of the wires are run through the frame 212, for example, in channels formed in at least some frame members 224. In an embodiment, at least a portion of the diverter controller 280 is not disposed on the support stent 210, for example, at a remote position in the patient's vasculature, implanted in the patient outside of the vasculature, or worn by the patient.

In an embodiment, the diverter controller 280 is operatively coupled to other components, for example, at least one of the actuator 250, first latch 256, second latch 258, or embolism detector 282, through wired connections. In an embodiment, the diverter controller 280 is operatively coupled to other components wirelessly. For example, in an embodiment, the first latch 256 and second latch 258 are operable by modulating a magnetic field thereon, for example, those comprising ferrofluid or magnetorheological fluid actuators. In an embodiment, the first latch 256 and second latch 258 comprising electrorheological fluid are operable by modulating an electric field thereon. In an embodiment, first latch 256, and second latch 258 that operate electrically, that is, change state on application of an electric potential or voltage are also operable wirelessly, for example, using a wirelessly coupled sub-controller disposed on the support stent 210 or embolism diverter 240. In an embodiment, a potential generated remotely in the support stent 210 or embolism diverter 240 inductively, for example, using one or more coils disposed on the support stent 210 or embolism diverter 240. In an embodiment, at least a portion of the diverter controller 280 is implanted outside of a patient's vasculature, adjacent to the support stent 210 or embolism diverter 240 implanted within the patient's vasculature.

In an embodiment, the diverter controller 280 includes an external input or external output operatively coupled to the data processing unit 272 for receiving or transmitting data, information, or commands from a remote location. For example, in an embodiment, the state of the embolism diverter 240 is settable by external commands received through the external input. For example, a physician may set the embolism diverter 240 in the divert state such that during a procedure that is likely to generate emboli, for example, balloon angioplasty or percutaneous aortic valve implantation. In an embodiment, the diverter controller 280 is capable of transmitting data or information externally, for example, at least one of status, activity, embolism detector output, success of diversion, power status, or device history. In an embodiment, the diverter controller 280 is reprogrammable, for example, through the external input or output. The external input or output is of any suitable type, for example a radio or RF transceiver, an inductive coupler, an electrical connector, or the like. In an embodiment the radio transceiver is a low-power radio transceiver, for example, using IEEE 802.15.1 (Bluetooth), ECMA-340 and ISO/IEC 18092 (near field communication, NFC), or the like. In some embodiment, at least a portion of the frame 212 is an antenna for the radio. In an embodiment in which the embolism detector 282 is an ultrasonic detector, discussed below, data, information, or commands are encoded in ultrasound.

As discussed in greater detail below, in an embodiment, the embolism deflecting device 200 comprises an embolism detector capable of determining the success of an embolism diversion event, for example, with a detection field downfield of the embolism deflecting device 200. In an embodiment, the diverter controller 280 also includes one or more control embolism diverter parameters that are updated based on data or information provided from the embolism detector with the downstream detection field.

A illustrated in FIG. 2B, the embolism detector 282 is disposable or implantable relative to a patient to provide a detection field D including the vasculature of the patient upstream of the embolism diverter 240 and support stent 210 in the illustrated embodiment. In an embodiment, the embolism detector 282 is capable of detecting at least emboli based on a targeted size in the detection field D traveling towards the embolism diverter 240 and support stent 210 sufficiently early to permit the embolism controller 280 to convert the embolism diverter 240 into the divert state. As such, the embolism detector 282 is coupled to the diverter controller 280. In an embodiment, the embolism detector 282 is operable to detect emboli in real time.

Suitable embolism detectors, systems, and methods of operation are disclosed, for example, in U.S. Patent Application Publication No. 2009/0281412 A1, the disclosure which is herein incorporated by reference in its entirety. Briefly, the embolism detector comprises at least one energy emitter and at least one energy sensor suitable for detecting reflected energy from the at least one energy emitter. In an embodiment, an output of the at least one energy emitter is controlled by the diverter controller 280 and output from the at least one energy sensor is received by the diverter controller 280. In an embodiment, the diverter controller 280 transforms that data or information received from the at least one energy sensor into a spectral signature and compares the spectral signature with characteristic emboli spectral signature data representative of or information related to the presence of at least one embolism to determine the presence or absence of one or more emboli, and optionally, characteristics of the emboli, for example, at least one of number of emboli, the embolism size, the embolism type, the embolism location, the embolism path, or the embolism arrival time. In an embodiment, the diverter controller 280 is operable to determine the likelihood or probability of emboli entering at least one of the more critical location or the less critical location.

In an embodiment, characteristic spectral signature data or information is refined using the output of the embolism detector, thereby improving the accuracy of embolism detection. In an embodiment, learning protocols improve the accuracy of the detection over time, for example, at least one of a spectral clustering protocol or a spectral learning protocol. In an embodiment, the embolism detector 282 is "smart," that is, performs at least a portion of the data or information processing. In an embodiment, the embolism detector is "dumb" and all of the data or information processing is performed by elsewhere, for example by the diverter controller 280. In an embodiment, the embolism detector 282 and diverter controller 280 are integrated.

In an embodiment, the embolism detector 282 includes at least one of an optical detector or an ultrasonic detector, classified according to the type of energy emitted and detected. In an embodiment, the embolism deflecting device 200 comprises a plurality of energy types, for example, optical and ultrasonic, which improves detection in an embodiment. In an embodiment, the optical embolism detectors 282 are disposed within the vasculature, for example, within the lumen of the first blood vessel F. In an embodiment, an ultrasonic embolism detector is disposable within the vasculature, as well as outside the vasculature in a position suitable for monitoring a blood vessel upstream of the embolism diverter 240 for emboli. For example, in an embodiment, an ultrasonic embolism detector is implantable adjacent to a target blood vessel, implantable subcutaneously, applied on a surface of a patient's skin, or worn. In an embodiment, the ultrasonic embolism detector includes a phased array ultrasonic detector.

In an embodiment in which the embolism detector 282 is disposed within the vasculature, the embolism diverter 282 is disposed on the support stent 210 with the detection field D upstream of the embolism diverter 240. In an embodiment, the embolism detector 282 is disposed on the support stent 210 at or near the inlet end 216. In an embodiment, the embolism detector 282 is disposed in the vasculature remote from the embolism diverter 240 and support stent 210, for example, on a separate stent, which is implantable upstream of the embolism diverter 240 and support stent 210.

In an embodiment of the embolism deflecting device 200 also have at least one detection field downstream of the embolism diverter 240, which is useful in determining if an embolism deflection event was successful. In an embodiment, the at least one downstream detection field is downstream of the second blood vessel or downstream of the third blood vessel. In an embodiment, the embolism deflecting device comprises at least a second embolism detector coupled to the diverter controller 280 situated for monitoring the at least one downstream detection field.

In an embodiment comprising at least one remote embolism detector 282, the at least one remote embolism detector 282 communicates with the diverter controller 280 wirelessly, for example, by radio or ultrasound, as discussed above in reference to wireless external communications.

The illustrated embodiment of the embolism deflecting device 200 further comprise a power source 284 coupled to the diverter controller 280. Examples of suitable power sources 284 include batteries or super capacitors. In an embodiment the power source 284 includes a thermoelectric generator. In an embodiment, the power source 284 is disposed on the support stent 210. In an embodiment, the power source 284 is implanted in another location in the body, is subcutaneous, or is worn.

As discussed above, in the illustrated embodiment, switching the embolism diverter 240 from the non-divert state to the divert state consumes energy. In an embodiment, the embolism deflecting device 200 consumes more power in the divert state than the non-divert state, for example, embodiments that do not comprise a latch that maintains the movable member 242 in the divert state.

In an embodiment, the device 200 is powered by at least one of blood flow, an energy storage device, a battery, a super capacitor, or an external power source. In an embodiment, the embolism deflecting device 200 harvests energy from a patient's movements, for example, walking, arm swinging, and the like. In an embodiment, energy from body movement is harvested using at least one of a piezoelectric generator, a microelectromechanical systems generator, or a biomechanical-energy harvesting generator. In an embodiment, power from the energy harvester recharges the power source 284.

In an embodiment, the embolism deflecting device 200 comprises a transcutaneous energy transfer system, for example, to directly power the device 200 or to recharge an internal or implanted power source, for example, a battery or super capacitor. In an embodiment, the transcutaneous energy transfer system is electromagnetically, magnetically, ultrasonically, optically, inductively, electrically, or capacitively-coupled to at least one of the embolism diverter 240, the diverter controller 280, or power source 284. In an embodiment, the transcutaneous energy transfer systems comprise at least one subcutaneously implantable energy receiver and at least one energy transmitter wearable by the patient in proximity with the at least one energy receiver.

As discussed above, in an embodiment, at least one of the diverter controller 280, embolism detector 282, or the power source 284 is not disposed on the support stent 210 or embolism diverter 240, for example, outside of the patient's vasculature. In an embodiment, the device 200 in which at least one of the diverter controller 280, embolism detector 282, or the power source 284 is disposed outside of the patient's vasculature exhibit one or more advantages, including, for example, any combination of improved blood flow through the vasculature, reduced thrombogenesis, easier maintenance or servicing, improved embolism detection, or simplified communication.

In an embodiment, at least portions of two of the diverter controller 280, embolism detector 282, and the power source 284 are integrated, thereby providing advantages including any combination of simplified delivery, simplified packaging, reduced trauma on implantation, improved communication between components, ease of maintenance, ease of replacement, improved reliability, and the like. In an embodiment, the diverter controller 280, embolism detector 282, and the power source 284 are integrated in a single package that is implantable or wearable on a patient's skin.

Figure 4:
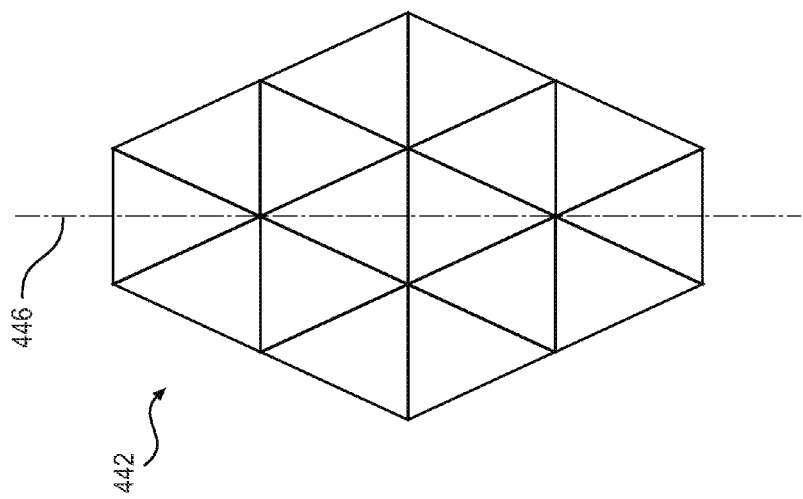
FIG. 4 is a front view of an embodiment of a movable member.
Figure 3:
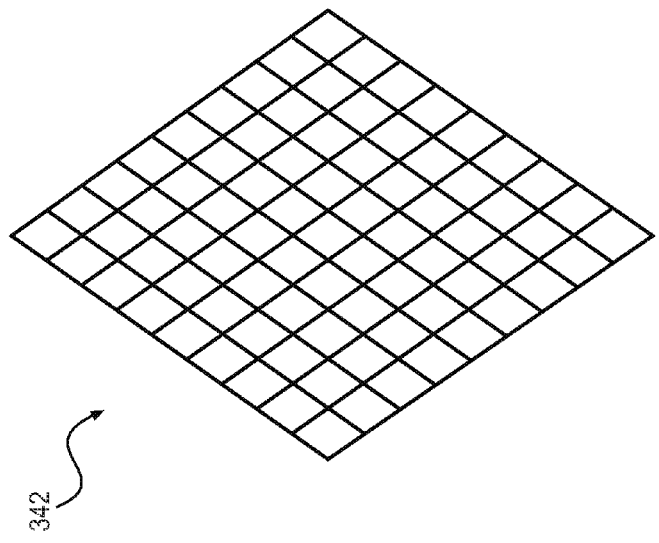
FIG. 3 is a front view of an embodiment of a movable member.

FIGS. 3 and 4 are front views of embodiments of movable members, 342 and 442, respectively, suitable as replacements for the movable member 242 in the device 200 illustrated in FIGS. 2A and 2B. In FIGS. 3 and 4, the movable members 342 and 442 have been flattened for clarity. The movable member 342 may be diamond or rhombus shaped, which can simplify fabrication. The movable member 442 is similar to the movable member 342, except truncated at the extremities of the longer axis 446 thereof, which facilitates attachment of the movable member 342 or reduces damage to a potentially delicate feature.

FIGS. 5, 6, and 7 are end cross-sectional views of embodiments of movable members 542, 642, and 742, respectively, in which the movable member comprises a plurality of flat sections such that a cross section across the minor axes 548, 648, and 748 is a polygon instead of a curve as in the movable member 242. Movable member 542 comprises two flat sections, movable member 642 comprises three flat sections, and movable member 742 comprises four flat sections. Other embodiments comprise more than four flat sections. In an embodiment, a movable member comprises at least one curved section and one flat section.

Figure 8:
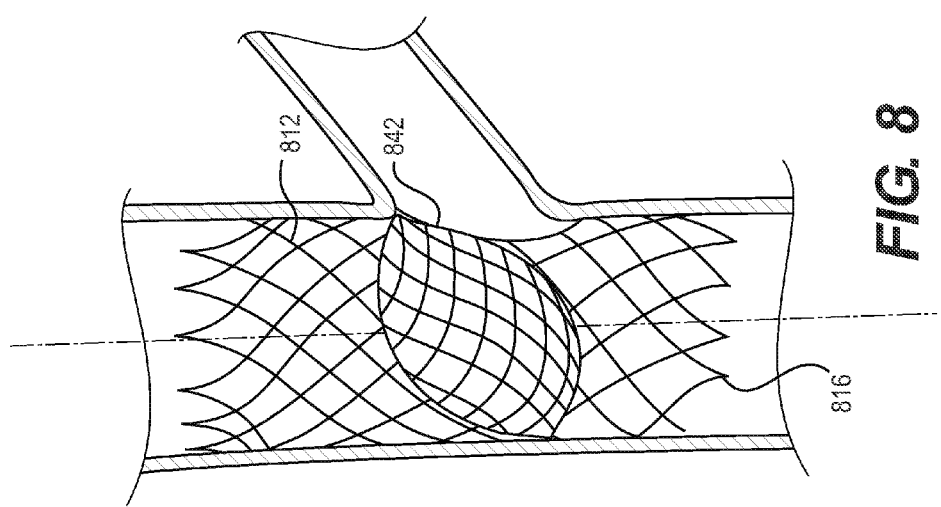
FIG. 8 is a side, cross-sectional view of an embodiment of a frame and movable member in a divert state.

FIG. 8 is a cross-sectional view of a tubular frame 812 of a support stent and a movable member 842 of an embodiment of an embolism deflecting device in a divert state. In the illustrated embodiment, the movable member 842 has a bowl shape that is concave towards an inlet end 816 of the frame, which facilitates emboli deflection.

Figure 9:
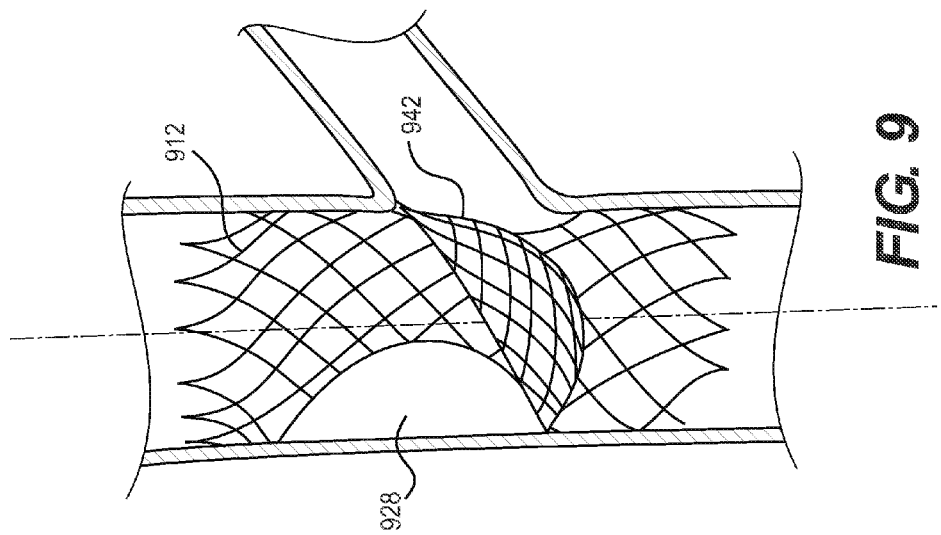
FIG. 9 is a side, cross-sectional view of an embodiment of a frame and movable member in a divert state.

FIG. 9 is a cross-sectional view of a tubular frame 912 of a support stent and a movable member 942 of another embodiment of an embolism deflecting device in the divert state. In the illustrated embodiment, a portion of the tubular frame 912 corresponding to the movable member 942 in the non-divert position has comparatively lower density of frame members 924 than the remainder of the frame 912 or has no frame members, thereby defining a recess 928 into which the movable member 942 rests in the non-divert state. In an embodiment, the tubular frame 912 and movable member 942 can facilitate delivery, for example, as compressible to a smaller diameter or more flexible in the compressed state. In an embodiment, the tubular frame 912 and movable member 942 in the non-divert state also exhibit at least one of reduce turbulence or reduced thrombogenicity.

Figure 10:
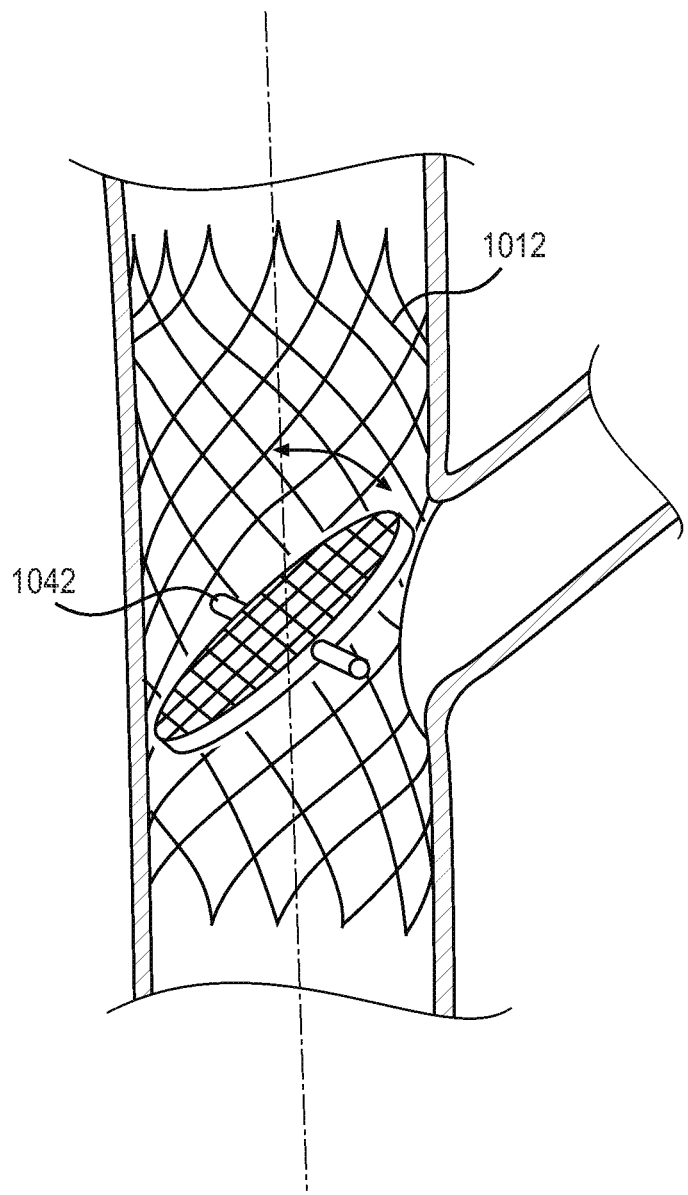
FIG. 10 is a side, cross-sectional view of an embodiment of a frame and movable member in a divert state.

Referring to FIGS. 2-9, in an embodiment, the movable member rotates or pivots around an axis that is generally parallel to a line tangent to a transverse cross section of the tubular frame. Referring to FIG. 10, in an embodiment, a movable member 1042 and frame 1012 of an embodiment of an embolism deflecting device similar to the device 200 in which the movable member 1042 rotates or pivots around an axis that is a chord of a transverse cross section of the frame 1012. In the illustrated embodiment, the chord is a diameter of the frame 1012.

Figure 11A:
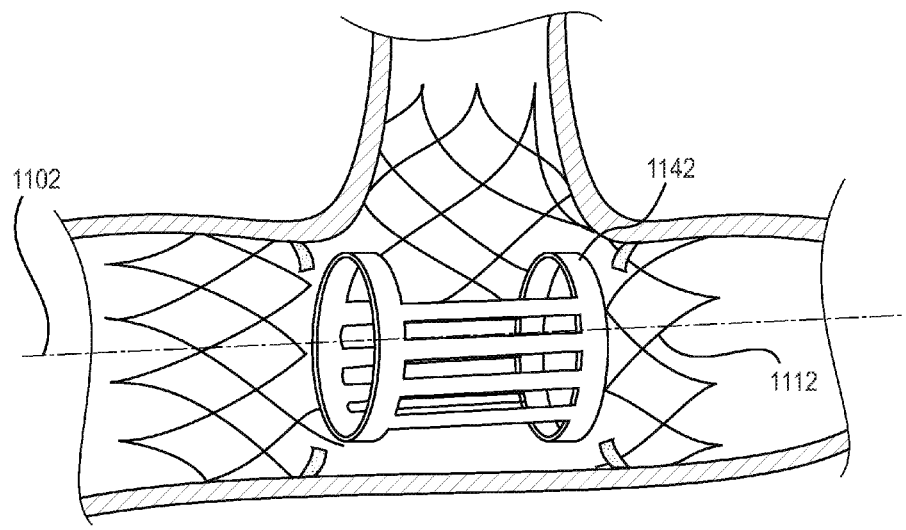
FIGS. 11A and 11B are side cross-sectional views of an embodiment of a frame and movable member in a non-divert state and a divert state, respectively.
Figure 11B:
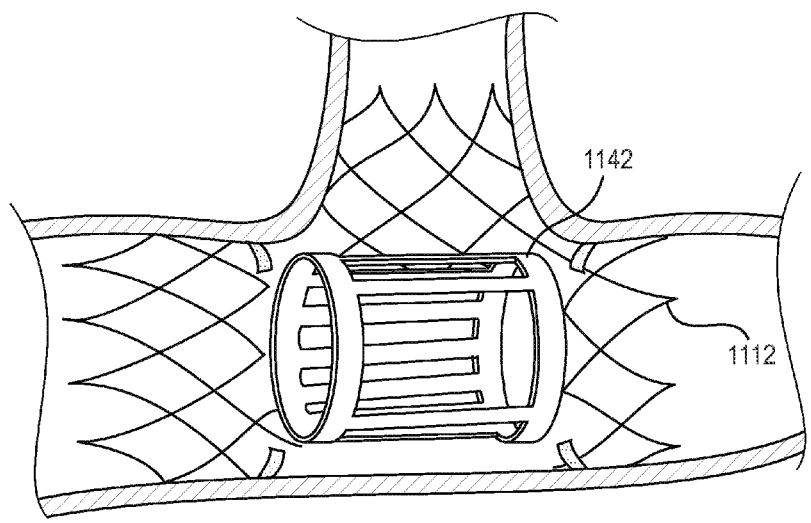

Referring to FIGS. 11A and 11B, in an embodiment, a movable member 1142 and frame 1112 of an embolism deflecting device similar to the device 200 in which the movable member 1142 rotates or pivots around a longitudinal axis 1102 of the frame 1112. In FIG. 11A, the movable member 1142 is in the non-divert state and in FIG. 11B, the movable member 1142 is in the divert state. The illustrated embodiment is suitable for situations in which the second blood vessel is a branch and the third blood vessel is generally coaxial with the first blood vessel, for example, where the first blood vessel is the aorta, the second blood vessel is the aorta, and the third blood vessel is the left common carotid artery 40. In an embodiment, the movable member 1142 is operable to block emboli from entering a plurality of second blood vessels, for example, the brachiocephalic artery and the left common carotid artery, thereby protecting both arteries from emboli. In an embodiment, protecting a plurality of second blood vessels can comprise a plurality of movable members.

In an embodiment, the movable member 1142 rotates between the non-divert state and the divert state. In an embodiment, the movable member 1142 rotates a different angle in converting between states, depending on the anatomy of the vessel branching. In an embodiment, the movable member 1142 controllably rotates between the non-divert and divert states, reversing direction in converting between states. In an embodiment, the movable member 1142 rotates in a single direction, clockwise or counterclockwise, in converting between the non-divert and divert states. In an embodiment, the movable member 1142 can include a single latch that locks the movable member in both the non-divert and divert states. In an embodiment, the movable member 1142 includes a plurality of latches. In an embodiment, the movable member 1142 is latch free.

In an embodiment, the movable member 1142 and frame 1112 includes magnets, for example, at least one permanent magnet on the movable member 1142 and at least one electromagnet on the frame 1112. In an embodiment, the polarity of the at least one electromagnet can be changed by applying a suitable electric current thereto, thereby controlling relative movement between the movable member 1142 and the frame 1112. In an embodiment, the movable member 1142 is substantially neutrally buoyant.

In the illustrated embodiment, the frame 1112 has a general T-shape, with arms of the "T" implantable in the first, second, and third blood vessels, which facilitate alignment of the movable member 1142 with the second blood vessel.

Figure 12A:
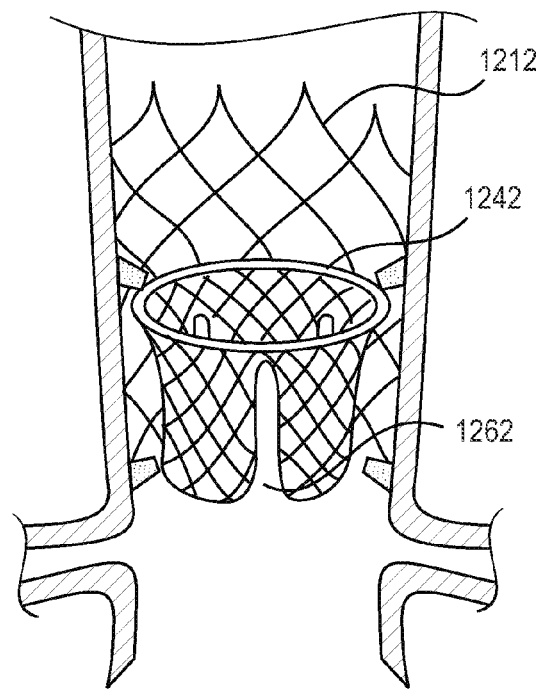
FIGS. 12A and 12B are side cross-sectional views of an embodiment of a frame and movable member in a non-divert state and a divert state, respectively.
Figure 12B:
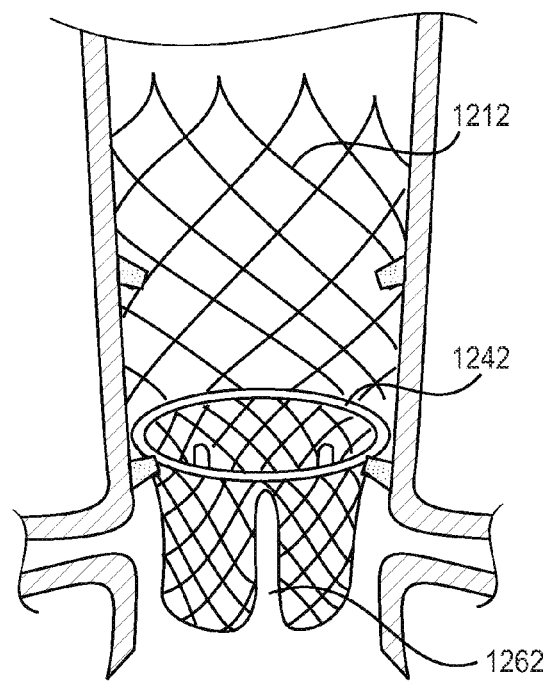

FIGS. 12A and 12B are perspective views of a movable member 1242 and a portion of a tubular frame 1212 of an embodiment of an embolism deflecting device in which the movable member translates longitudinally between the non-divert and divert states. In the illustrated embodiment, the frame 1212 is implanted in one of the first or third blood vessels and the movable member 1242 extends to the branch point of the second blood vessel, for example, where the frame 1212 is implanted in the ascending aorta, the third blood vessel, and the second blood vessel is the coronary arteries. In the illustrated embodiment, the movable member 1242 comprises a notch 1262 that accommodates an aortic valve commissure therein. Another embodiment does not comprise a notch, for example, when the movable member is used to block emboli from a blood vessel other than the coronary arteries. In an embodiment, the longitudinal movement of the movable member 1242 is activated as described above, for example, using an actuator mechanically or magnetically coupling the movable member 1242 to the frame 1212, or by blood flow.

An embodiment of the embolism diverter includes at least one movable member and at least one fixed member, where the fixed member is fixed relative to a frame of a support stent. In an embodiment, neither the at least one movable member or the at least one fixed member by themselves are capable of blocking or diverting emboli of the target size, but together in the divert state, are capable of blocking or diverting emboli of the target size. In an embodiment, at least portions of the at least one movable member and the at least one fixed member are aligned or eclipse each other in the non-divert state, and are overlapping or staggered in the divert state. In an embodiment, the movement of the at least one movable member between the non-divert state and the divert state is relatively small compared with similar embodiments of embolism diverters that do not comprise at least one fixed member. In an embodiment, in converting between the non-divert state and the divert state, the at least one movable member rotates or pivots relative to the at least one fixed member, for example, around an axis generally tangent to a tubular frame, around an axis that is a chord of a tubular frame, around an axis that is a diameter of a tubular frame, or around a longitudinal axis of a tubular frame. In an embodiment, in converting between the non-divert state and the divert state, the at least one movable member translates relative to the at least one fixed member.

Figure 13A:
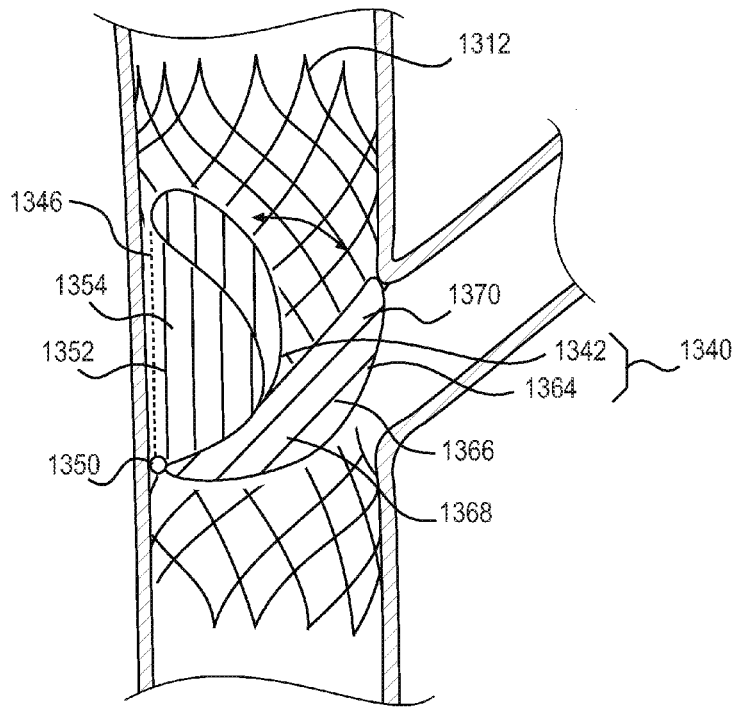
FIG. 13A is a side cross-sectional views of an embodiment of a frame, movable member, and fixed member in a non-divert state.

FIG. 13A is a cross-sectional view of a tubular frame 1312 and portions of an embolism diverter 1340 of another embodiment of an embolism deflecting device in the non-divert state, which is similar to the device 200. In the illustrated embodiment, the embolism diverter comprises a movable member 1342 and a fixed member 1364, which are generally similar in shape and size. In the illustrated embodiment, the fixed member 1364 can be configured to extend across a lumen 1314 of the frame at an angle suitable for directing emboli into a third blood vessel. In an embodiment, the fixed member 1364 is secured to the frame 1312. A coupling member 1350 pivotably couples an inlet end of the movable member 1342 proximal to an inlet end of the fixed member 1364, such that the movable member 1342 is pivotable to juxtapose the movable member 1342 with the fixed member 1364. At least a portion of the fixed member 1364 is shaped and dimensioned to nest with at least a portion of the movable member 1342, one within the other in the divert state.

In an embodiment, the fixed member 1364 comprises at least one blocking member 1366 defining at least one aperture 1368. In an embodiment, the at least one aperture 1368 is larger than a target size of emboli-to-be-diverted. In an embodiment, the movable member 1342 also comprises at least one blocking member 1352 defining at least one aperture 1354, which is larger than a target size of emboli-to-be-diverted.

In an embodiment, the at least one blocking members 1352 and 1366 of the movable member and fixed member, respectively, includes at least one of a mesh, a screen, an obstructing member, a plurality of non-intersecting bars, or a spiral element. In the illustrated embodiment, the at least one blocking members 1352 and 1366 of the movable member and fixed member each include a plurality of non-intersecting bars that can be configured generally parallel to major axes 1346 and 1370 of the movable member and fixed member, respectively, which define a plurality of slot-shaped apertures 1354 and 1368 of the movable member and fixed member, respectively.

Figure 13B:
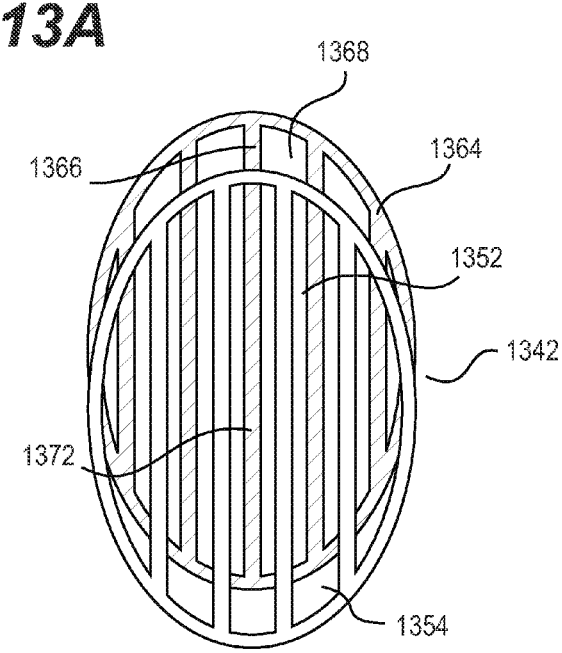
FIG. 13B is a top view of the movable member, and fixed member in a divert state.

FIG. 13B is a top view of the movable member 1342 and fixed member 1364 in the divert state. In the illustrated embodiment, the movable member 1342 and fixed member 1364, which are similar in shape and size, substantially overlap, with the blocking members 1352 and 1366 of each disposed in the apertures 1368 and 1354 of the other, together defining openings 1372 smaller than the target size of the emboli, thereby diverting emboli away from the second blood vessel.

Figure 14A:
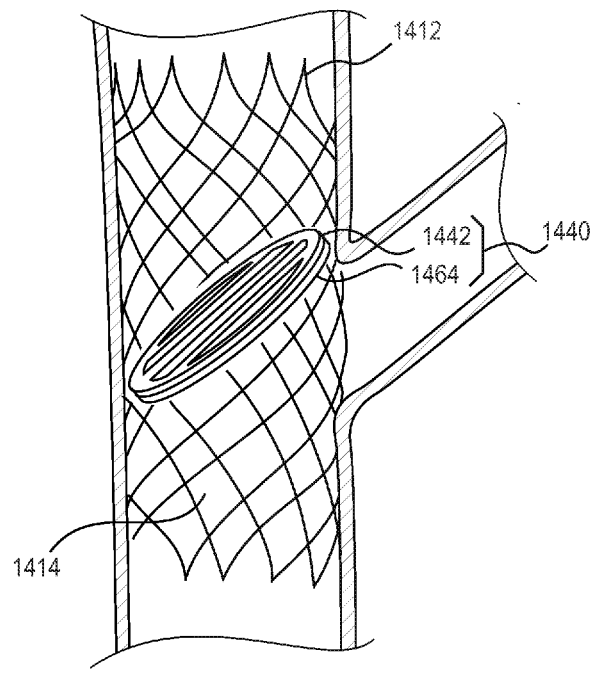
FIG. 14A is a side cross-sectional view of an embodiment of a frame, movable member, and fixed member in a non-divert state.

FIG. 14A is a perspective view of an embodiment of a frame 1412 and portions of an embolism diverter 1440 of an embodiment of an embolism deflecting device similar to the embodiment illustrated in FIGS. 13A and 13B, as well as the other embodiments described above. In the illustrated embodiment, the embolism diverter 1440 comprises at least one movable member 1442 and a fixed member 1464. The fixed member 1464 is similar to the fixed member 1364 described above, generally configured to extend across a lumen 1414 of the frame and secured thereto at an angle suitable for deflecting emboli into a third blood vessel. At least a portion of the movable member 1442 and at least a portion of the fixed member 1464 are stacked together, that is, adjacent to and overlapping, in both the non-divert and divert states. In the illustrated embodiment, the fixed member 1464 and movable member 1442 have similar shapes and sizes. Both generally flat in the illustrated embodiment, simplifying fabrication or deployment. In an embodiment, the fixed member 1464 and movable member 1442 are curved similarly to the embodiment illustrated in FIGS. 13A and 13B.

Figure 14B:
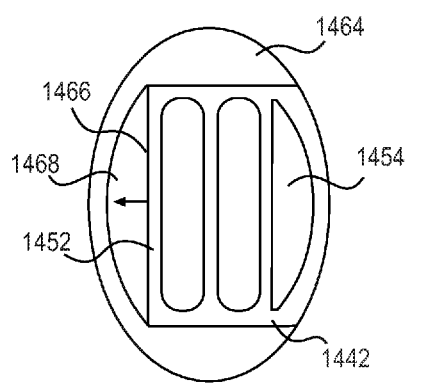
FIGS. 14B and 14C are top views of the movable member, and fixed member in a non-divert state and a divert state, respectively.

FIG. 14B is a top view of the movable member 1442 and fixed member 1464 in the non-divert state. The movable member 1442 is similar to the movable member 1342 described above, comprising a blocking member 1452 comprising a plurality of parallel bars and apertures 1454. In an embodiment, the fixed member 1464 also comprises a blocking member 1466 comprising a plurality of parallel bars and apertures 1468. In an embodiment, the apertures 1454 and 1468 are larger than a target size of the emboli-to-be-diverted. A spacing between the bars 1452 of the movable member is substantially the same as the bars 1466 of the fixed member, and in the non-divert state, the bars 1452 and 1466, and apertures 1454 and 1468 can be eclipsed, lining-up and overlapping as shown in FIG. 14B. Consequently, the aligned apertures 1454 and 1468 together are larger than the target size of emboli-to-be-detected. In an embodiment, the bars 1452 and 1466 do not precisely align and overlap in the non-divert state. Because the bars 1452 and 1466 are fully or partially eclipsed in the non-divert state, they present a reduced cross-section to blood flow, which reduces turbulence or thrombogenicity in an embodiment.

Figure 14C:
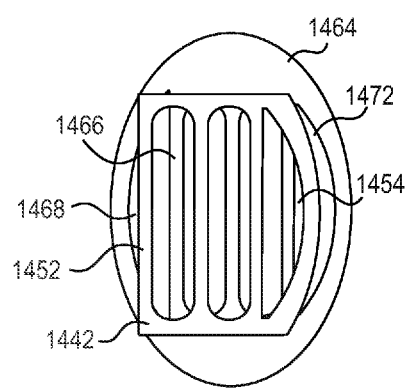

FIG. 14C is a top view of the movable member 1442 and fixed member 1464 in the divert state. In an embodiment, the movable member 1442 is translated relative to the fixed member 1464, substantially in-plane, along an axis at an angle to the bars 1452 and 1466, in the illustrated embodiment, substantially normal to or perpendicular to the bars 1452 and 1466, thereby staggering the bars 1452 and 1466. In the illustrated embodiment, the movable member has been translated a distance about half the spacing between adjacent bars, such that the bars 1452 are disposed at about half- or mid-way between the bars 1466 of the fixed member, thereby, the bars 1452 and 1466 together defining openings 1472 smaller than the size of the emboli-to-be-deflected. In an embodiment, the movable member is translated a different distance, for example, greater than or less than half of the spacing between adjacent bars.

In an embodiment, a device includes a plurality of movable members and a fixed member. For example, in an embodiment similar to the embodiment illustrated in FIGS. 14A-14C, a first movable member is translatable about one-third of the bar spacing and a second movable member is translated about one-third of the bar spacing in an opposite direction as the first movable member. In an embodiment, the second movable member is translatable about two-third of the bar spacing in the same direction as the first movable member. In the non-divert state, the bars of the first movable member, the second movable member, and the fixed member are eclipsed. In an embodiment, the fixed member is sandwiched between the first and second movable member. In an embodiment, the second movable member is disposed between the first movable member and the fixed member.

Figure 15A:
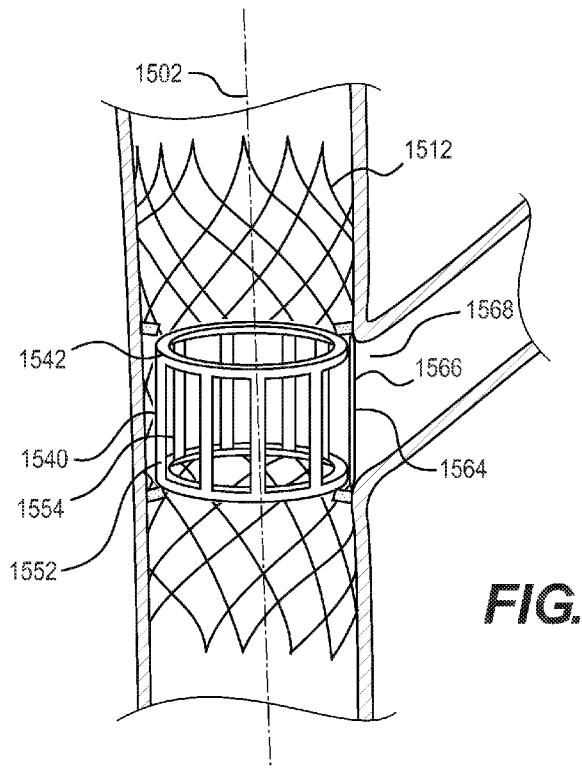
FIG. 15A is a side cross-sectional view of an embodiment of a frame, movable member, and fixed member in a non-divert state.

FIG. 15A is a cutaway view of a tubular frame 1512 and a portion of an embolism diverter 1540 that is similar to the embodiment illustrated in FIGS. 11A and 11B and described above. In the illustrated embodiment, the embolism diverter 1540 comprises a movable member 1542 and a fixed member 1564. In an embodiment, the fixed member 1564 is generally cylindrical, and in the illustrated embodiment, is integrated with the frame 1512. In an embodiment, the fixed member 1564 is not integrated with the frame 1512. In an embodiment, the fixed member 1564 comprises at least one blocking member 1566, which in the illustrated embodiment, comprises a plurality of generally evenly spaced bars generally parallel with a longitudinal axis 1502. In an embodiment, the at least one blocking member 1566 defines at least one aperture 1568, which is larger than a target embolism-to-be-blocked.

In an embodiment, the generally cylindrical movable member 1542 is dimensioned to rotatably fit inside of and concentric with the fixed member 1564, in the illustrated embodiment, with a small or substantially no gap therebetween. In an embodiment, the movable member 1542 comprises at least one blocking member 1552, which in the illustrated embodiment, comprises a plurality of generally even spaced bars generally parallel with the longitudinal axis 1502, which define at least one aperture 1554. In an embodiment, the blocking member 1552 of the movable member is similar in size, shape, and structure as the blocking member 1566 of the fixed member, with the same number of bars of similar widths. In an embodiment, the blocking member 1552 of the movable member is at least as tall or high as the blocking member 1566 of the fixed member.

Figure 15B:
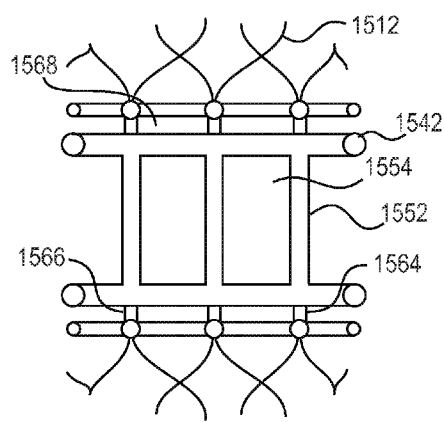
FIGS. 15B and 15C are detail views of the movable member, and fixed member in a non-divert state and a divert state, respectively.

As illustrated in FIG. 15B, which is a cross-sectional view of the movable member 1542 and the fixed member 1564 in the non-divert state, the movable member 1542 is concentric with the fixed member 1564, and generally longitudinally centered therewith. In an embodiment, the blocking member 1552 of the movable member mirrors the blocking member 1566 of the fixed member, and consequently, eclipses each other in the non-divert state with the apertures 1554 and 1568 aligned.

Figure 15C:
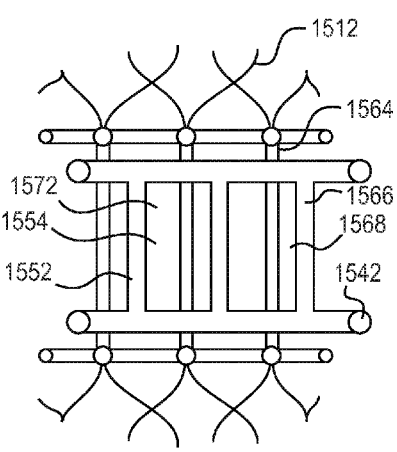

In the divert state illustrated in FIG. 15C, the movable member 1542 is rotated around the longitudinal axis 1502 relative to the fixed member 1564, staggering the blocking member 1552 of the movable member and the blocking member 1566 of the fixed member, thereby defining at least one opening 1572 smaller than the target size of the embolisms-to-be-blocked. In an embodiment, the particular angle that the movable member 1542 rotates in converting between the non-divert and divert states depends on the particular structure of the blocking members 1552 and 1566. For example, in the illustrated embodiment, the angle depends on the number of bars in the blocking member 1552 or 1566. In an embodiment, the movable member 1542 rotates in a first direction in converting from the non-divert state to the divert state, and in a second direction opposite the first direction in converting back to the non-divert state. The illustrated embodiment of the movable member 1542 and fixed member 1564 are generally rotationally symmetric, and consequently, is implantable at any rotational orientation in a branch or bifurcation in the vasculature so long as the embolism diverter 1540 is longitudinally aligned with the second blood vessel.

Figure 16A:
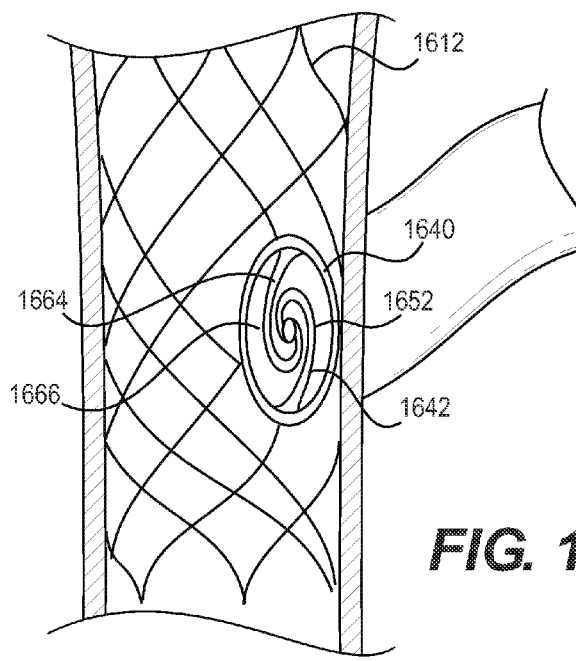
FIG. 16A is a side cross-sectional view of an embodiment of a frame, movable member, and fixed member in a divert state.

FIG. 16A is a perspective view of an embodiment of a tubular frame 1612 and a portion of an embolism diverter 1640. In the illustrated embodiment, the embolism diverter 1640 comprises a movable member 1642 adjacent to a fixed member 1664, each of which is generally configured to cover the opening to the blood vessel. As shown in FIG. 16A, the fixed member 1664 is disposed in the frame 1612 at a location of a branch of a second blood vessel from a first blood vessel and a third blood vessel. In an embodiment, the fixed member 1664 comprises at least one blocking member 1666, which in the illustrated embodiment includes a spiral element. In an embodiment, the movable member 1642 has the same general size and shape, and includes a blocking member 1652 that includes a spiral element with substantially the same dimensions, shape, and handedness as the blocking member 1666 of the fixed member. In the illustrated embodiment, the fixed member 1664 and movable member 1642 are substantially flat. In an embodiment, the fixed member 1664 and movable member 1642 are not flat, for example, conical.

Figure 16B:
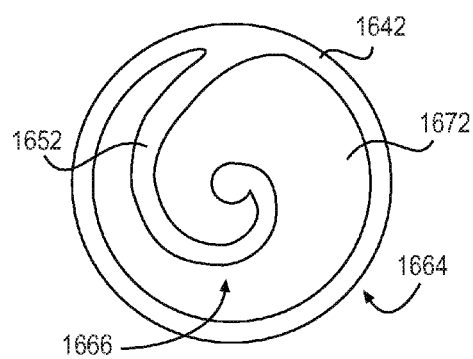
FIGS. 16B and 16C are top views of the movable member, and fixed member in a non-divert state and a divert state, respectively.
Figure 16C:
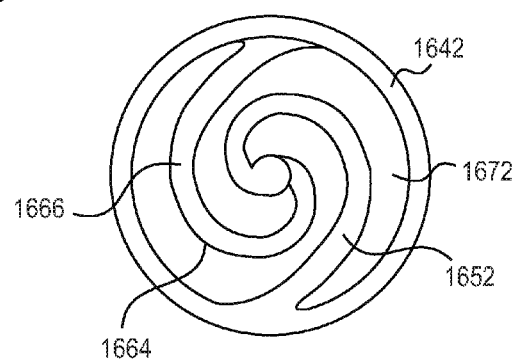

FIG. 16B is a front view of the movable member 1642 aligned with and completely covering the fixed member 1664 in the non-divert state. In an embodiment, the spiral elements 1652 and 1666 are eclipsed, defining an opening 1672 larger than a target size of emboli. In the divert state illustrated in FIG. 16C, the movable member 1642 is rotated relative to the fixed member 1664, by about 180° in the illustrated embodiment, thereby defining an opening 1672 smaller than the target size. In an embodiment, the spiral elements 1652 and 1666 are relatively rotated as described above, for example, using an actuator mechanically or magnetically coupling the movable member 1642 to the frame 1612, or by blood flow.

FIG. 17A is a cutaway view of an embodiment of a tubular frame 1712 and a portion of an embolism diverter 1740. In the illustrated embodiment, the embolism diverter 1740 comprises a fixed member 1764 and a tubular movable member 1742 disposed therein. In the illustrated embodiment, a blocking member 1766 of the fixed member is integrated with the frame 1712. In the illustrated embodiment, both the fixed member 1764 and the movable member 1742 are generally cylindrical. In an embodiment, the fixed member 1764 and the movable member 1742 have a different shape, for example, frustoconical, elliptic cylindrical, or another suitable shape.

In the illustrated embodiment, the blocking member 1766 of the fixed member includes a mesh. In an embodiment, the movable member 1742 comprises a blocking member 1752 also including a mesh with the mesh sized to align with the mesh of the blocking member 1766 of the fixed member in the non-divert state. In the non-divert state illustrated in FIG. 17B, which is front view of the movable member 1742 and the fixed member 1764, the mesh blocking member 1752 of the movable member eclipses the mesh blocking member 1766 of the fixed member. In the divert state illustrated in FIG. 17C, the movable member 1742 is translated longitudinally by about one-half of a vertical mesh spacing such the mesh blocking member 1752 of the movable member and the mesh blocking member 1766 of the fixed member are staggered or offset, defining at least one space 1772 dimensioned to block emboli of the target size. In the illustrated embodiment, a height of the blocking member 1752 of the movable member is larger than a height of the blocking member 1766 of the fixed member by about one-half of the vertical mesh spacing.

In an embodiment, the embolism deflecting device comprises a plurality of movable members, the movable members in the divert state overlapping each other and defining at least one opening dimensioned to block emboli of the target size. In an embodiment, each of the plurality of movable members does not separately define an opening dimensioned to block emboli of the target size, for example, in the non-divert state. In an embodiment, at least some of the movable members rotate or translate relative to a tubular frame in converting between the non-divert state and the divert state. In an embodiment, each of the movable members comprises at least one of a mesh, a screen, an obstructing member, a plurality of non-intersecting bars, or a spiral element.

Figure 18A:
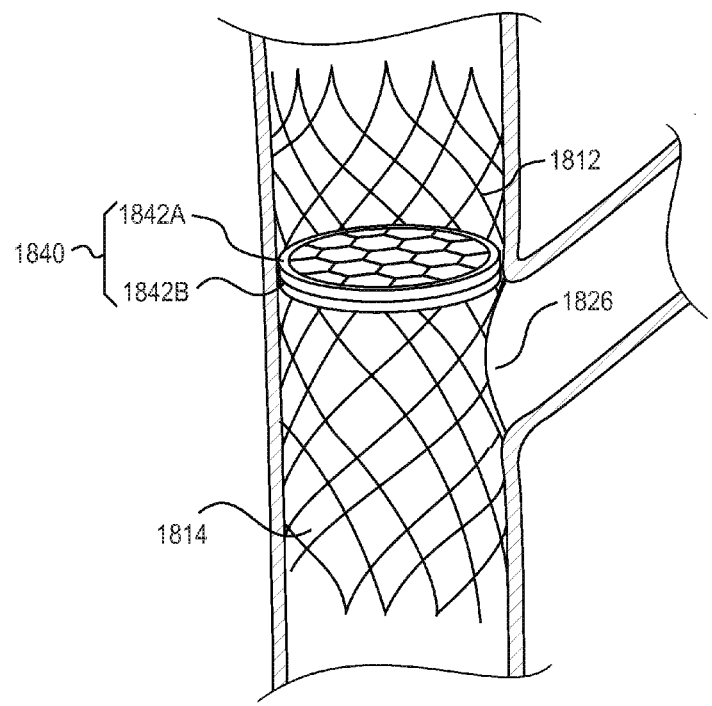
FIG. 18A is a side cross-sectional view of an embodiment of a frame, first movable member, and second movable member.

FIG. 18A is a cutaway view of embodiment of a tubular frame 1812 and a portion of an embolism diverter 1840 comprising a first movable member 1842a and a second movable member 1842b. In the illustrated embodiment, the first movable member 1842a and the second movable member 1842b are disposed in a lumen 1814 of the frame just downstream of an open area 1826 positionable at a branch point in the vasculature. In the illustrated embodiment, the first movable member 1842*a* and the second movable member 1842*b* are generally circular and stacked one on top of the other, each comprising a blocking member 1852*a* and 1852*b*. In the illustrated embodiment, each of the blocking members 1852*a* and 1852*b* comprises a substantially identical hexagonal mesh. Each blocking member 1852*a* and 1852*b* defines at least one aperture 1854*a* and 1854*b* larger than a target embolism size.

Figure 18B:
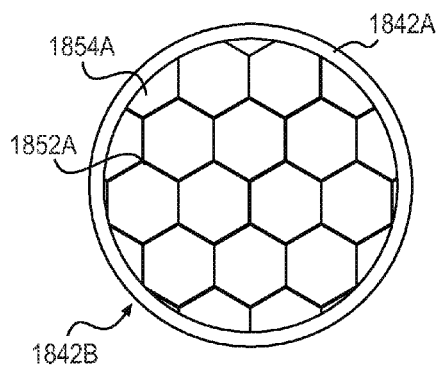
FIGS. 18B and 18C are top views of the first movable member, and second movable member in a non-divert state and a divert state, respectively.

FIG. 18B is a top view of the first movable member 1842*a* and the second movable member 1842*b* in the non-divert state. In an embodiment, the meshes of the first and second blocking members 1852*a* and 1852*b* are aligned, as are the apertures 1854*a* and 1854*b*. Consequently, the embolism diverter 1840 does not block emboli of the target size in the non-divert state.

Figure 18C:
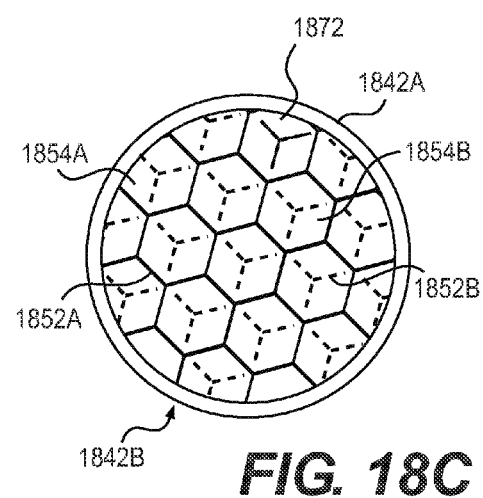

In FIG. 18C, which is a top view of the first movable member 1842*a* and the second movable member 1842*b* in the divert state, the first movable member 1842*a* is rotated about 15° clockwise and the second movable member 1842*b* is rotated about 15° counterclockwise, the first and second blocking members 1852*a* and 1852*b* thereby defining at least one opening 1872 smaller than the target embolism size.

In an embodiment of the embolism deflecting device comprise a movable member comprising a flow diverter that deflects or diverts emboli away from the second blood vessel upstream of the more critical location by modifying or modulating blood flow away from an entrance of the second blood vessel rather than by blocking the entrance to the second blood vessel.

Figure 19A:
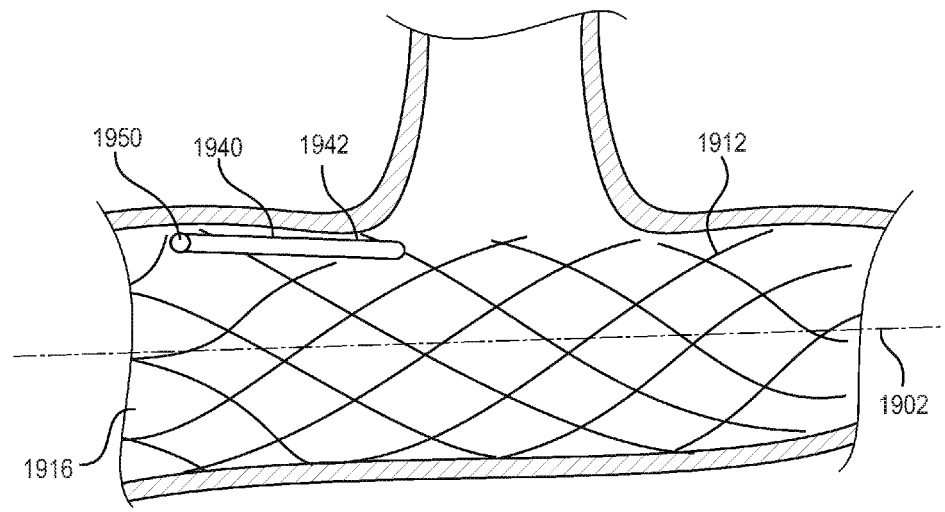
FIGS. 19A and 19B are side cross-sectional views of an embodiment of a frame and movable member in a non-divert state and a divert state, respectively.

FIG. 19A is a cross-sectional side view of an embodiment of a tubular frame 1912 and a portion of an embolism diverter 1940 in a non-divert state, the embolism diverter 1940 comprising a movable member 1942 that is a flow diverter. In an embodiment, the flow diverter 1942 has a first cross section in the non-divert state and a second cross section in the divert state. In an embodiment, the flow diverter 1942 comprises at least one of a deflector surface, a ramp, a fin, or a rotatable snout. In the illustrated embodiment, the flow diverter 1942 comprises a ramp disposable upstream of a branch point in the vasculature. A coupling member 1950 pivotably couples an end of the flow diverter 1942 proximal to an inlet end 1916 to the frame 1912. In the illustrated embodiment, the flow diverter 1942 is disposed along a wall of the frame 1912 in the non-divert state, presenting a smaller cross section, thereby reducing the effect on blood flow.

Figure 19B:
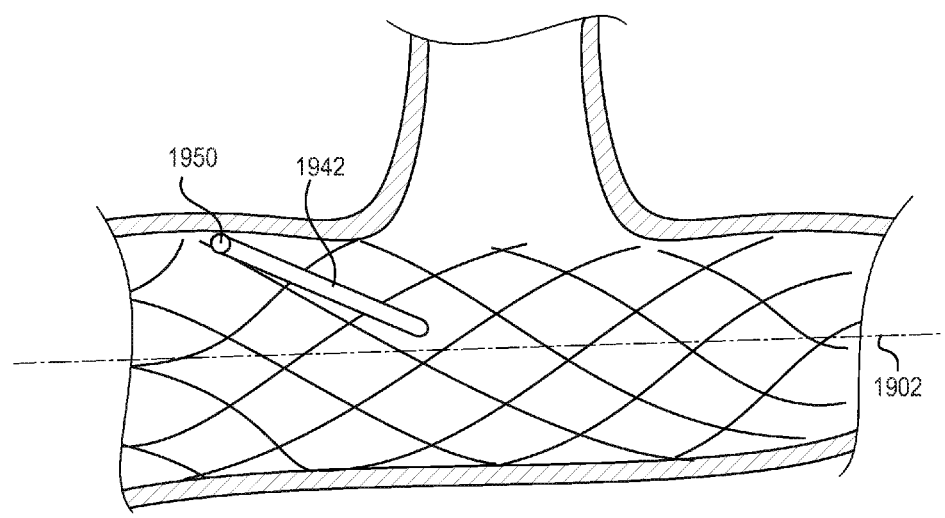

In FIG. 19B, the flow diverter 1942 is in the divert state. In an embodiment, the flow diverter 1942 pivots around the connecting member 1950 away from the wall of the frame 1912 with a downstream or outlet end of the flow diverter 1942 closer to a longitudinal axis 1902, presenting a larger cross section to the blood flow. In the divert state, the flow diverter 1942 channels or diverts blood flow away and emboli entrained therein from the entrance of the second blood vessel, thereby reducing the likelihood of a stroke in a more critical body location downstream thereof.

Figure 20A:
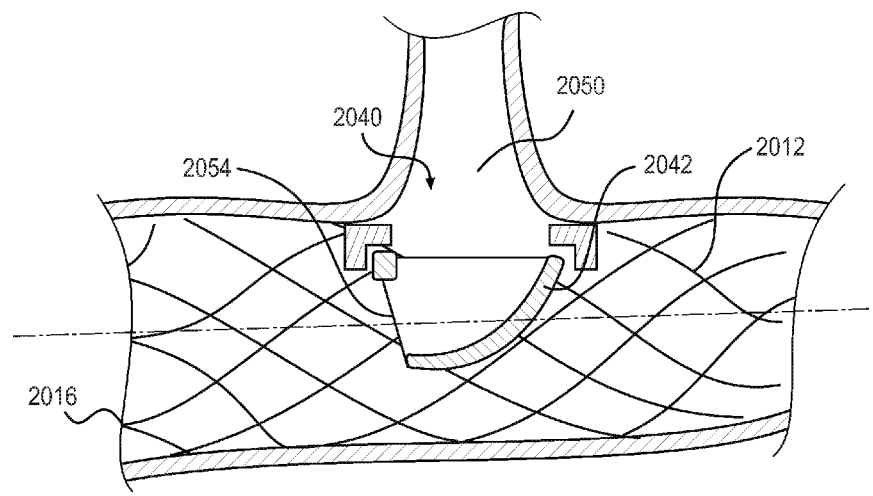
FIGS. 20A and 20B are side cross-sectional views of an embodiment of a frame and movable member in a non-divert state and a divert state, respectively.

FIG. 20A is a cross-sectional side view of another embodiment of a tubular frame 2012 and a portion of an embolism diverter 2040, where the embolism diverter 2041 comprises a flow-diverter movable member 2042. In FIG. 20A, the flow diverter 2042 is in the non-divert state. In the illustrated embodiment, the flow diverter 2042 comprises a tubular, rotatable snout with an outlet 2050 fluidly coupled to an inlet 2054, the outlet 2050 and inlet 2054 opening or pointing in different directions, in the illustrated embodiment, about 90° apart. In an embodiment, an angle between the outlet 2050 and the inlet 2054 is from about 45° to about 135°. In an embodiment, the rotatable snout 2042 extends inwardly from the frame 2012 with the outlet 2050 rotatably coupled thereto at a location alignable with an entrance to a second blood vessel, and the inlet 2054 opening into a lumen 2014 of the frame.

Figure 20B:
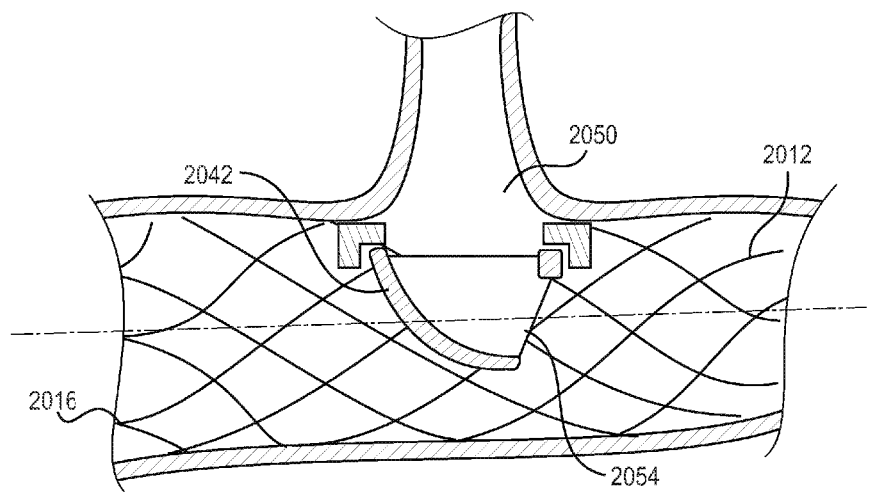

In the non-divert state illustrated in FIG. 20A, the inlet 2054 faces an inlet end 2016 of the frame, thereby presenting a first cross section of the rotatable snout 2042 to the blood flow in which blood freely enters the inlet 2054. In the divert state illustrated in FIG. 20B, the rotatable snout 2042 is rotated around the outlet 2050 such that the inlet 2054 faces an outlet end 2018 of the frame, about 180° from the orientation in the non-divert state in the illustrated embodiment. In the divert state, the rotatable snout 2042 presents a second cross section to the blood flow that encourages blood flow therearound, thereby reducing the likelihood that an embolism will enter the inlet 2054.

Figure 21:
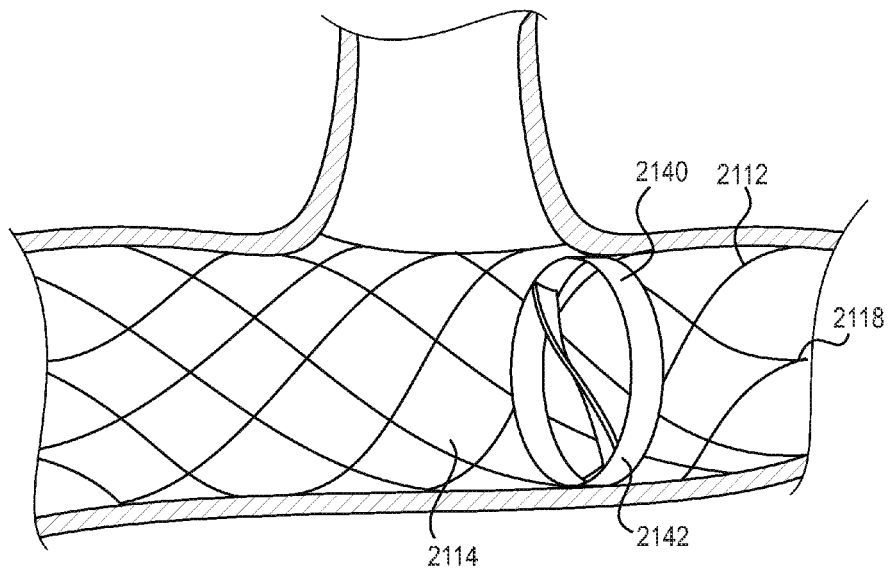
FIG. 21 is a side cross-sectional view of an embodiment of a frame and movable member.

FIG. 21 is a side view of another embodiment of a tubular frame 2112 and a portion of an embolism diverter 2140 in which the embolism diverter comprises a movable member 2142 that includes a rotating blade or flow jet. In the illustrated embodiment, the rotating blade or flow jet 2142 comprises a propeller. In an embodiment, the rotating blade or flow jet 2142 comprises, for example, a helix or screw. In the illustrated embodiment, the rotating blade 2142 is coupled to the frame 2112 in a lumen 2114 thereof, and towards an outlet end 2118 thereof, and downstream of a branch point of a second blood vessel. In the non-divert state, the rotating blade 2142 is activated at a first level that does not divert blood flow away from an entrance of the second blood vessel. In an embodiment, the rotating blade 2142 does not substantially alter blood flow in an unpowered state, and the first activation level is unpowered. In an embodiment, the first activation level is a powered level.

In the divert state, the rotating blade 2142 is activated at a second level that diverts blood flow and emboli therein away from the entrance of the second blood vessel. In the illustrated embodiment, increasing a rotational speed of the rotating blade 2142 increases blood flow into the third blood vessel, thereby reducing blood flow into the second blood vessel. Consequently, a likelihood of an embolism entering the second blood vessel is reduced in the divert state.

In an embodiment, a device includes a plurality of rotating blades or flow jets, for example, a first disposed upstream of the entrance to the second blood vessel and a second disposed downstream thereof. In an embodiment, the first and second rotating blades or flow jets have substantially identical properties. In an embodiment, the first and second rotating blades or flow jets have different properties. For example, in an embodiment, the second or downstream rotating blade or flow jet produces a higher flow rate than the first or upstream rotating blade or flow jet at a given activation level.

Figure 22:
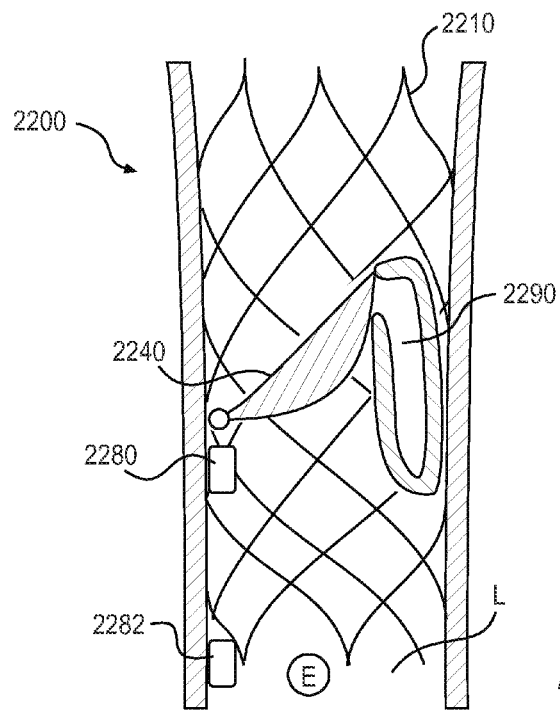
FIG. 22 is a side cross-sectional view of an embodiment of an embolism deflecting device in a divert state.

FIG. 22 illustrates another embodiment of an embolism deflecting device 2200, which is generally similar to the embodiment illustrated in FIGS. 2A and 2B. In an embodiment, the device 2200 include the embolism diverter of another embodiment described above. In an embodiment, the embolism deflecting device 2200 comprises a support stent 2210, an embolism diverter 2240, a diverter controller 2280, and an embolism detector 2282. In an embodiment, the embolism deflecting device 2200 further comprises an implantable container 2290 coupled to the support stent 2210. In the illustrated embodiment, the implantable container 2290 is disposed in the lumen L of the blood vessel. In an embodiment, at least a portion of the container 2290 is disposed outside of the blood vessel, for example, through a wall of a fabric graft.

In FIG. 22, the support stent 2210, embolism diverter 2240, diverter controller 2270, and embolism detector 2282 are implanted in a lumen L of a blood vessel. In an embodiment, the implantable container 2290 is configured to be in fluid communication with the lumen L of the blood vessel at least part of the time, and is the less critical location in the illustrated embodiment. In the divert state, the embolism diverter 2240 deflects a substantial fraction of emboli E into the implantable container 2290 where the emboli are removed from the bloodstream. In an embodiment, the implantable container 2290 comprises a one-way or tortuous internal structure that tends to retain emboli therein. Some embodiments of the container 2290 are configured to receive emboli only when the embolism diverter 2240 is in the divert state. In an embodiment, the implantable container 2290 comprises a mesh or screen that permits blood flow therethrough.

In an embodiment, the implantable container 2290 comprises a sensor or detector that indicates a fill level of the container 2290. In an embodiment, the fill-level sensor is operatively coupled to the diverter controller 2280, which includes instructions that depend on the fill level of the container 2290, for example reporting a full container 2290 to an external receiver. In an embodiment, the container 2290 is retrievable and replaceable, for example, when full. In an embodiment, the container 2290 is retrievable and replaceable independently of the remainder of the device 2200, for example, percutaneously or surgically, for example, by minimally invasive surgery, for example, through a trocar.

In an embodiment, the device 2200 is useful in portions of the vasculature that do not comprise branch blood vessels suitable for diverted emboli, for example, the venous portion of the circulatory system. In an embodiment, the device 2200 is implantable in the inferior vena cava where it captures emboli shed by deep venous thrombosis (DVTs) in the patient's legs.

In an embodiment, a kit comprising an embolism deflecting device of any suitable type describe above, and a percutaneous delivery system dimensioned for delivering the embolism diverting device to a desired location in the vasculature. In an embodiment, the percutaneous delivery system comprises an elongate guide catheter comprising a lumen, the guide catheter dimensioned for advancement through the patient's vasculature to the desired location, and an elongate device delivery catheter advanceable through the lumen of the guide catheter, the embolism deflecting device releasably mountable on a distal end of the device delivery catheter. In an embodiment, the device delivery catheter is a balloon catheter.

In an embodiment, a system comprising an embolism deflecting device as described above, and machine readable instructions that when executed on the diverter controller, convert the movable member of the embolism diverter from the non-divert state to the divert state based on a target input. In an embodiment, the machine readable instructions are stored on machine readable media. In an embodiment, the machine-readable instructions include at least one of cryptographic protocol information, regulatory compliance protocol information, regulatory use protocol information, authentication protocol information, authorization protocol information, activation protocol information, encryption protocol information, and decryption protocol information. In an embodiment, the machine readable instructions, when executed on the diverter controller, activate at least one of a Spectral Clustering protocol or a Spectral Learning protocol operable to compare one or more parameters associated with the output of the embolism detector with one or more information subsets associated with reference spectral signature data or information.

In an embodiment, the target input is an external command. For example, as discussed above, in an embodiment, a physician sends a command that converts the device into the divert state in response to a procedure that is likely to generate emboli. In an embodiment, the target input is an output of the embolism detector, as discussed above. In an embodiment comprising a power source, the target signal includes an energy level of the power source.

Figure 23:
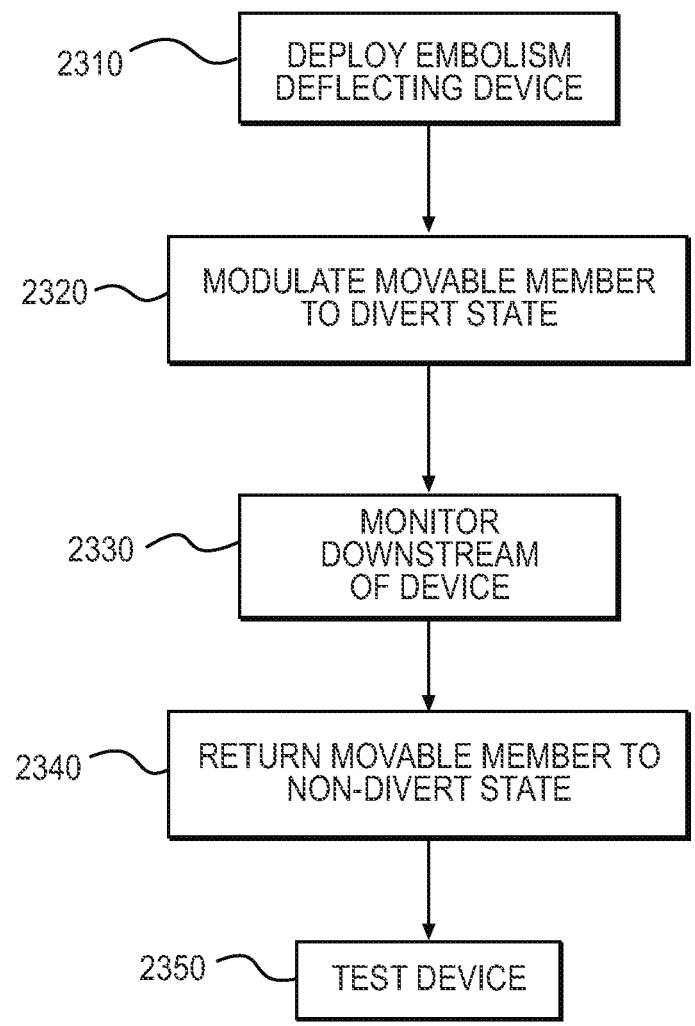
FIG. 23 is a flow chart illustrating an embodiment of a method for deflecting an embolism.

FIG. 23 is a flowchart illustrating an embodiment of a method 2300 for deflecting an embolism from a more critical location to a less critical location in a patient.

At 2310, at least a portion of the embolism deflecting device 200 is deployed in the lumen L of a blood vessel, for example, the first blood vessel F. As discussed above, in an embodiment, at least portions of the embolism deflecting device 200 is disposed in any combination of the first blood vessel F, the second blood vessel S, and the third blood vessel T.

As discussed above, in an embodiment, at least a portion of the embolism deflecting device 200 is deployed at a bifurcation B of the first blood vessel F into a second blood vessel S and a third blood vessel T, where the second blood vessel S is upstream of the more critical location and the third blood vessel T upstream of the less critical location. In an embodiment, the bifurcation of the first blood vessel into a second blood vessel and a third blood vessel includes a bifurcation of at least one of a first vein into a second vein and a third vein; a first artery into a second artery and a third artery; a carotid artery into an internal carotid artery and an external carotid artery; an ascending aorta into a brachiocephalic artery and an arch of the aorta; or an arch of the aorta into a left common carotid artery and a descending aorta. In an embodiment, the more critical location is at least one of a brain, a lung, or a heart of the patient.

As discussed above, in an embodiment, the embolism deflecting device comprises an implantable container, for example, the embodiment illustrated in FIG. 22. In an embodiment, the embolism deflecting device is implanted in a blood vessel upstream of a more critical location with the less critical location including the implantable container. In an embodiment, the method includes monitoring a fill level of the implantable container. In an embodiment, the method includes replacing the implantable container, for example, when filled to a target level. In an embodiment, the implantable container is replaced percutaneously or surgically.

In an embodiment, the support stent 210 of the device is radially compressed and secured to a percutaneous delivery system. In an embodiment, the embolism diverting device 200 is then introduced into the vasculature and advanced to a desired location in the lumen L of the blood vessel, whereupon it is unsecured or released from the percutaneous delivery system. In an embodiment, the support stent 210 of the embolism diverting device is expanded, thereby anchoring the device 200 at the desired position.

At 2320, the at least one movable member 242 is modulated or repositioned, thereby converting the embolism diverter 240 of an embolism deflecting device 200 from the non-divert state to the divert state. As discussed above, in the divert state, the embolism diverter 240 diverts a significant fraction of emboli towards a less critical body location and away from the more critical body location. In the non-divert state, the embolism diverter 240 does not divert a significant fraction of emboli towards a less critical body location and away from the more critical body location. For example, in an embodiment, the embolism diverter 240 does not appreciably affect blood flow in the non-divert state, or preserves the direction of blood flow to both the more critical and the less critical body location. Consequently, in an embodiment, a significant fraction of emboli are capable of flowing or traveling to the more critical location in the non-divert state. In an embodiment, the at least one movable member 242 is repositioned in response to a target input associated with a presence of an embolism upstream of the embolism deflecting device 200. In an embodiment, the target input is sent from the embolism detector 282 to the deflector controller 280, which in turn converts the embolism deflector 240 from the non-divert to the divert state. In an embodiment, emboli are detected in a detection field upstream of the embolism diverting device 200, for example, optically or ultrasonically.

At 2330, at least one detection field downstream of the embolism deflecting device 200 is optionally monitored to determine the success of the embolism deflection at 2320.

At 2340, the movable member 242 is optionally modulated or repositioned to convert the embolism diverter from the divert state to the non-divert state. In an embodiment, the diverter controller 280 repositions the movable member 242 after determining if the deflection was successful at 2330. In an embodiment, the diverter controller 280 repositions the movable member 242 after a selected time period. In an embodiment, the embolism deflection is monitored in real time using the embolism detector 282.

At 2350, operation of embolism deflecting device 200 is tested by activating the embolism detector 282 or activating the embolism diverter 240 in the absence of an embolism.

Figure 24:
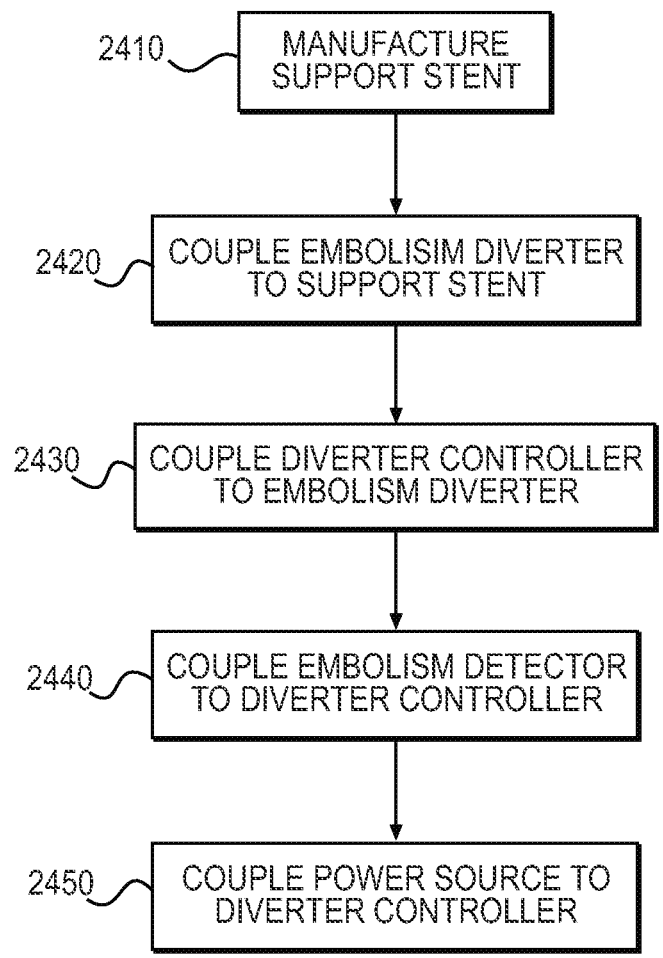
FIG. 24 is a flow chart illustrating an embodiment of a method for manufacturing an embolism deflector.

FIG. 24 is flowchart illustrating an embodiment of a method 2400 for manufacturing an embolism diverting device with reference to the device 200 illustrated in FIGS. 2A and 2B. The method is also applicable to manufacturing other embodiments of embolism deflecting devices, for example, other embodiments disclosed herein.

At 2410, the support stent 210 is manufactured by any suitable method, for example, for example, machining, water jet machining, laser machining, laser cutting, welding, laser welding, swaging, sewing, suturing, mechanical fastening, 3-D printing, gluing, and combinations thereof. In an embodiment, the frame 212 of the support stent is manufactured by laser cutting a hypotube.

At 2420, the embolism diverter 240 including the movable member 242 is coupled to the support stent 210. In an embodiment, the embolism diverter 240 is coupled prior to implantation in the patient. In an embodiment, at least a portion of embolism diverter 240 is coupled to the stent 210 after implantation thereof.

At 2430, the diverter controller 280 is operatively coupled to the embolism diverter 240. In an embodiment, the diverter controller 280 is manufactured from at least one of a processor, a microprocessor, a field programmable gate array, or an application-specific integrated circuits; a memory device; and a bus therebetween. An embodiment further comprises writing characteristic spectral signature data or information on the memory device. In an embodiment, at least one of a Spectral Clustering protocol or a Spectral Learning protocol is written on the memory device.

At 2440, the embolism detector 282 is operatively coupled to the diverter controller 280. Optionally, at 2450, the power source 284 is operatively coupled to the diverter controller 280.

Figure 25:
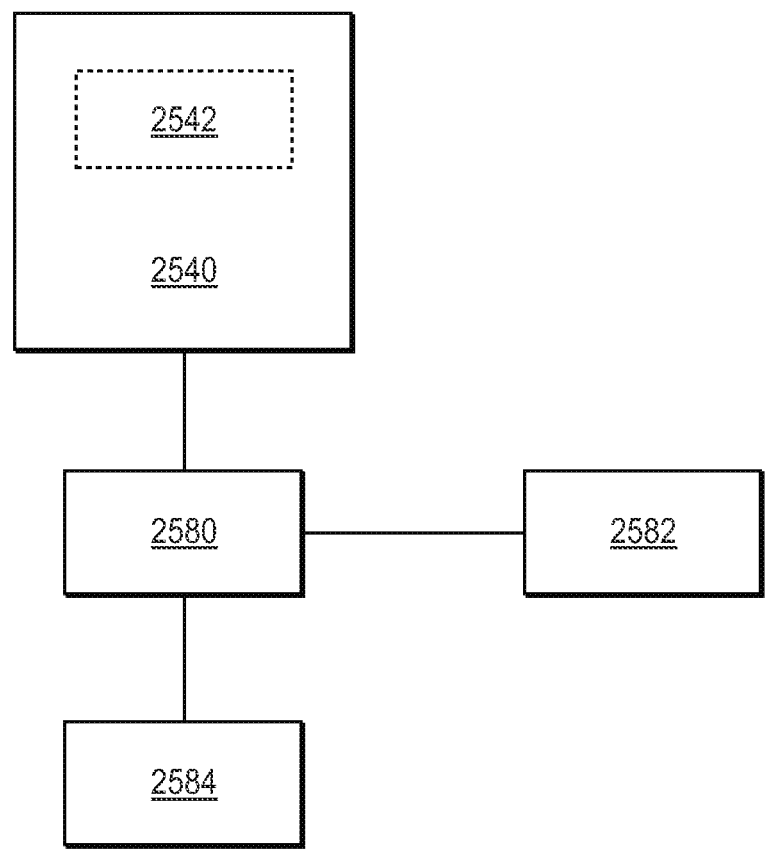
FIG. 25 is a schematic illustration of an embodiment of an embolism deflector.

FIG. 25 schematically illustrates another embodiment of an embolism deflecting device 2500 suitable for deflecting an embolism away from the more critical location of the patient to a less critical location. In an embodiment, the device 2500, in whole or in part, is securable to or disposable relative to the patient in position suitable for operating on a blood vessel or portion of the vasculature upstream of the more critical location and the less critical location, in an embodiment, proximate to the blood vessel or portion of the vasculature. The illustrated embodiment of the embolism deflecting device 2500 comprises an embolism diverter 2540, a diverter controller 2580, an embolism detector 2582, and a power source 2584. In an embodiment, the embolism diverter 2540, embolism detector 2482, and power source 2584 are each operatively coupled to the diverter controller 2580. As discussed above, in an embodiment, components or subcomponents of the embolism deflecting device 2500 are operatively coupled using wires or wirelessly.

In an embodiment, the embolism detector 2582 is disposable relative to the patient or securable to the patient with a detection field thereof including a detection area in a blood vessel or portion of the vasculature upstream of the more critical location and the less critical location. As discussed above, an embodiment further comprises a second embolism detector with a detection field downstream of the target area, which is useful for determining the success of a diversion or deflection event.

In an embodiment, the embolism detector 2582 includes at least one of an optical detector and an ultrasound detector. In an embodiment, in which at least a portion of the embolism detector 2582 is disposed in a lumen of the blood vessel, that portion of the embolism detector 2582 is coupled to a support stent or other support structure dimensioned for deployment in the lumen. As discussed above, at least a sensor and an emitter of optical embolism detectors are generally disposed in the lumen of a blood vessel.

In an embodiment, at least a sensor or an emitter of an ultrasonic detector are disposed in the lumen. In an embodiment, no portion of an ultrasonic detector is disposed in the lumen of the blood vessel. For example, in an embodiment, at least one ultrasonic emitter or at least one ultrasonic sensor is implanted proximate to, adjacent to, or in juxtaposition with the blood vessel. In an embodiment, at least one ultrasonic emitter or at least one ultrasonic sensor is implanted in another location, for example, subcutaneously. In an embodiment, at least one ultrasonic emitter or at least one ultrasonic sensor is disposed outside of the patient's body, for example, in contact with or coupled with an outer surface of a patient's skin. In an embodiment, the at least one ultrasonic emitter or at least one ultrasonic sensor is releasable from the skin, thereby permitting, for example, repositioning, replacement, or inspection of the site. In an embodiment, the at least one ultrasonic emitter or at least one ultrasonic sensor is semi-permanently secured or coupled to the patient's skin.

In the illustrated embodiment, the embolism diverter 2540 includes at least one ultrasound emitter 2542. In an embodiment, the at least one ultrasound emitter 2542 is disposable relative to or securable to the patient at a location suitable to expose a target area in the vasculature or blood vessel to sufficient ultrasound to at least a substantial fraction of emboli away from the more critical location and towards the less critical location. As discussed above, the embolism diverter 2540 is operable by the diverter controller 2480 in response to the detection of one or more emboli in the detection area. In an embodiment, the target area is within the detection field of the embolism detector 2582, which permits the diverter controller to monitor the diversion or deflection in real time. In an embodiment, the detection area at least partially overlaps the target area, or is upstream of the target area.

In an embodiment, the embolism diverter 2540 comprises a plurality of ultrasound emitters 2542. In an embodiment, the plurality of emitters 2542 permits operating at least one of the emitters 2542 at a lower power than a similar diverter 2540 using a single emitter 2542, thereby reducing potential side effects, for example, tissue damage or heating. In an embodiment, the plurality of emitters 2542 together uses less power than a single emitter 2542. In an embodiment, only some of the plurality of emitters 2542 is activated for at least a portion of the activation of the embolism diverter 2540. In an embodiment, the plurality of emitters 2542 is a phased array of emitters. In an embodiment, the output of the plurality of emitters 2542 is aimable by phase conjugation.

In an embodiment, the embolism diverter 2540 is at least partially integrated with the embolism detector 2582, where the detector 2582 includes an ultrasonic detector. For example, in an embodiment, the at least one emitter 2542 of the embolism diverter is an emitter for the embolism detector 2582.

In an embodiment, the embolism diverter 2540, the diverter controller 2580, and the embolism detector 2582 are packaged together in a single unit. In an embodiment, the package further comprises the power source 2584. In an embodiment, the package is implantable, for example, within the vasculature, outside the vasculature, adjacent to the target area, or subcutaneously. In other units, the package is secured to the skin of the patient. In an embodiment, a coupling agent is disposed between the package and the skin, for example, a gel, fluid, or other suitable substance.

As discussed above, in an embodiment, the embolism deflecting device 2500 is directed to a target area including a bifurcation of a first blood vessel into a second blood vessel upstream of the more critical location, and a third blood vessel upstream of the less critical location. In an embodiment, the embolism deflecting device 2500 is directed to a target area including a blood vessel upstream of the more critical location and an implantable container that includes the less critical location, as discussed above. In an embodiment, the implantable container is coupled to or supported by an intravascular stent.

In an embodiment, a system comprising the embolism deflecting device 2500, which is generally similar to the system described above in conjunction with the embolism deflecting device 200.

Figure 26:
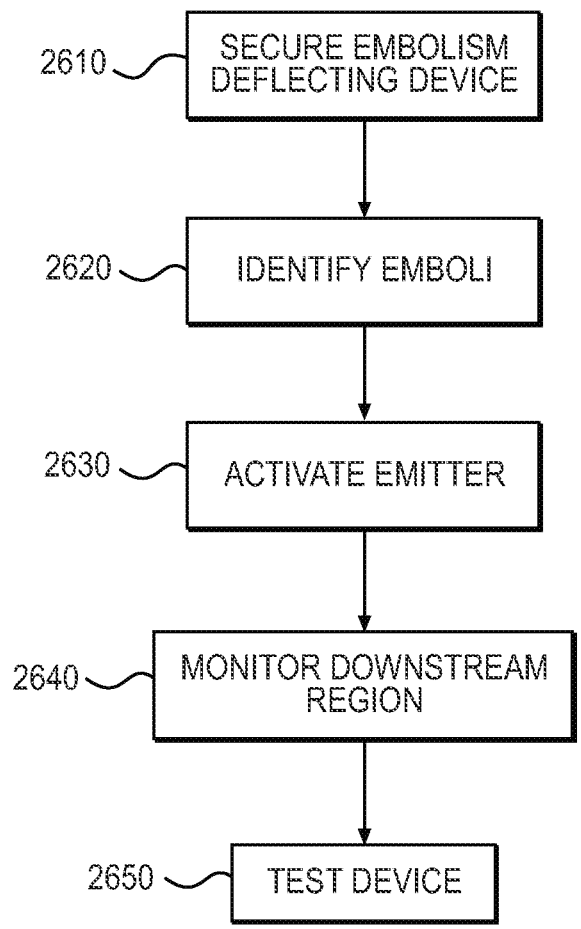
FIG. 26 is a flow chart illustrating an embodiment of a method for deflecting an embolism.

FIG. 26 schematically illustrates an embodiment of a method 2600 for deflecting or diverting one or more emboli from the more critical location to the less critical location, with reference to the embodiment of the device 2500. The method is also applicable to other embodiments of embolism deflecting devices. The method is generally similar to the method 2400 described above.

At 2610, at least a portion of the embolism deflecting device 2500 is secured to or disposed relative to a patient. In an embodiment, the embolism detector 2582 is disposed such that the detection field thereof includes the detection area in the vasculature or blood vessel upstream of the more critical location and the less critical location. In an embodiment, the at least one emitter is disposed such that ultrasound emitted therefrom effectively steers emboli in a target area away from the more critical location towards the less critical location. As discussed above, in an embodiment, the embolism device 2500 is at least one of deployed in the vasculature, in the blood vessel, implanted in the body outside of the vasculature, implanted proximate to the blood vessel, implanted subcutaneously, or secured to a patient in contact with the surface of the skin thereof. In an embodiment, at least a portion of the embolism detector 2582 and the at least one emitter 2542 is secured to the patient.

At 2620, the diverter controller 2580 identifies one or more emboli in the detection area based on the target input from the embolism detector.

At 2630, the diverter controller 2580 activates the at least one ultrasound emitter 2542 at a level sufficient to steer at least a significant fraction of emboli in the target area from the more critical location to the less critical location. In an embodiment, the ultrasound emitter 2542 is activated by the diverter controller 2580 in response to the identification of one or more emboli at 2620. In an embodiment, the target area is monitored by the embolism detector 2582 during the deflection event. In an embodiment, the diverter controller 2580 generates a control signal that causes the emitter 2542 to affect the trajectory of at least one embolism, for example, towards the more critical location or towards the less critical location.

At 2640, a region downstream of the target area is optionally monitored to evaluate the success or failure of the embolism deflection at 2630.

At 2650, operation of embolism deflecting device 2500 is tested by imaging the detection area using the embolism detector 2582 or activating the at least one emitter 2542 in the absence of an embolism.

Figure 27:
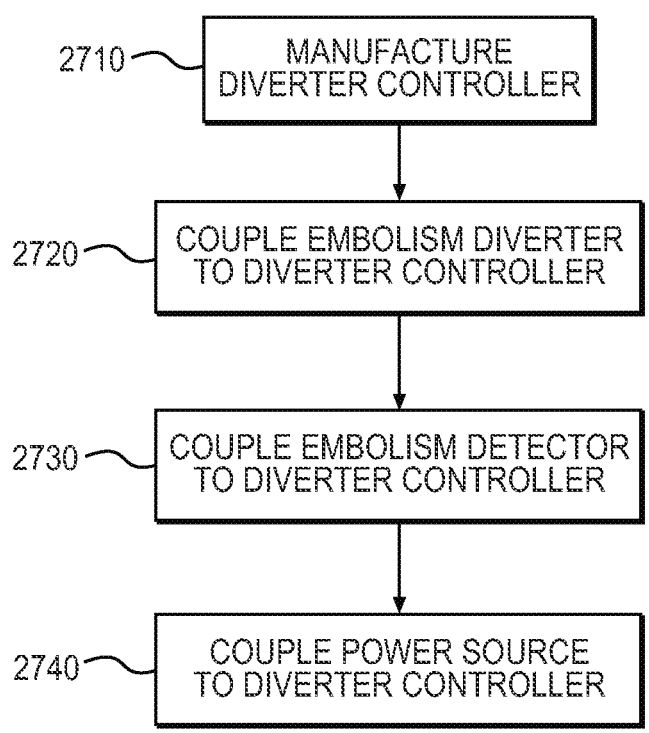
FIG. 27 is a flow chart illustrating an embodiment of a method for manufacturing an embolism deflector.

FIG. 27 is a flow chart schematically illustrating an embodiment of a method 2700 for manufacturing the embolism diverting device 2500, although the method is also applicable to manufacturing other embodiments, as well.

At 2710, the diverter controller is manufactured. In an embodiment, the diverter controller is manufactured by operatively coupling at least one of a processor, a microprocessor, a field programmable gate array, or an application-specific integrated circuits; a memory device; and a data bus therebetween. In an embodiment, a method includes writing characteristic spectral signature data or information on the memory device. In an embodiment, a method includes writing at least one of a Spectral Clustering protocol or a Spectral Learning protocol on the memory device.

At 2720, the embolism diverter 2540, which includes at least one ultrasonic emitter 2542, is operatively coupled to the diverter controller 2580.

At 2730, the embolism detector 2582 is operatively coupled to the diverter controller 2580.

At 2740, the power source 2584 is operatively coupled to the diverter controller 2580.

As discussed above, in an embodiment, some or all of the components of the embolism deflecting device 2500 are assembled in a single package.

The claims, description, and drawings of this application may describe one or more of the instant technologies in operational/functional language, for example as a set of operations to be performed by a computer. Such operational/functional description in most instances can be specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions are representative of static or sequenced specifications of various hardware elements. This is true because tools available to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits—)—are generators of static or sequenced specifications of various hardware configurations. This fact is sometimes obscured by the broad term "software," but, as shown by the following explanation, what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, http://en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, Natural language, http://en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct." (e.g., that "software"—a computer program or computer—programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In an embodiment, if a high-level programming language is the tool used to implement a technical disclosure in the form of functions/operations, it can be understood that, far from being abstract, imprecise, "fuzzy," or "mental" in any significant semantic sense, such a tool is instead a near incomprehensibly precise sequential specification of specific computational—machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory devices, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, http://en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, http://en.wikipedia.org/wiki/Instructions_per_second (as of Jun. 5, 2012, 21:04 GMT).

Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification which selects out hardware logic gates, specifies voltage levels, voltage transition timings, etc., such that the humanly useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. Accordingly, any such operational/functional technical descriptions may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object which has a stable, measurable, and changeable state may be used to construct a machine based on the above technical description. Charles Babbage, for example, constructed the first computer out of wood and powered by cranking a handle.

Thus, far from being understood as an abstract idea, it can be recognizes that a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language simply cannot be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

At least a portion of the devices or processes described herein is integrated into a data or information processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), or control systems including feedback loops and control motors (e.g., feedback for sensing position or velocity; control motors for moving or adjusting components or quantities). A data processing system may be implemented utilizing suitable commercially available components, such as those typically found in data computing/communication or network computing/communication systems.

The herein described subject matter sometimes illustrates different components contained within, or connected with, different other components. It is to be understood that such depicted architectures are merely exemplary, and that in fact, many other architectures may be implemented that achieve the same functionality. In a conceptual sense, any arrangement of components to achieve the same functionality is effectively "associated" such that the desired functionality is achieved. Hence, any two components herein combined to achieve a particular functionality is seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include, but are not limited to, physically mateable or physically interacting components, or wirelessly interactable, or wirelessly interacting components, or logically interacting, or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components or inactive-state components or standby-state components, unless context requires otherwise.

Although specific dependencies have been identified in the claims, it is to be noted that all possible combinations of the features of the claims are envisaged in the present application, and therefore the claims are to be interpreted to include all possible multiple dependencies.

The foregoing detailed description has set forth various embodiments of the devices or processes via the use of block diagrams, flowcharts, or examples. Insofar as such block diagrams, flowcharts, or examples contain one or more functions or operations, it will be understood by the reader that each function or operation within such block diagrams, flowcharts, or examples are implemented, individually or collectively, by a wide range of hardware, software, firmware, or virtually any combination thereof. Further, the use of "Start," "End" or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, or A, B, and C together, etc.). Typically a disjunctive word or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. An embolism deflecting device, comprising:
    a support stent including a substantially tubular frame at least partially defining a lumen, the substantially tubular frame having a first end in fluid communication with a second end through the lumen, the first end having an inlet to receive blood from a blood vessel, the second end having an outlet through which the blood exits the support stent, the substantially tubular frame of the support stent having an anchor for removably securing at least a portion of the support stent in the blood vessel;
    an embolism detector including an embolism sensor configured to detect an embolism in a detection field in the blood upstream of the blood vessel, the embolism detector including a transmitter operable for transmitting information associated with a presence of detected emboli in the detection field;
    an embolism diverter including one or more movable members movably secured to the substantially tubular support stent, the one or more movable members operable to direct a substantial portion of detected emboli of at least a target size in one of at least two directions;
    at least one diverter controller operatively coupled to the embolism detector and to the embolism diverter, the at least one diverter controller operable for receiving information from the embolism detector and responsively moving at least one of the one or more movable members to a divert state, which is configured to divert a substantial fraction of detected emboli of at least a target size in one or more of the at least two directions; and
    an implantable container disposed within the lumen defined by the support stent, the implantable container in fluid communication with the blood vessel at least part of the time, the embolism diverter deflecting the substantial fraction of emboli into the implantable container when the at least one of the one or more movable members is in the divert state.

2. The embolism deflecting device of claim 1, wherein the embolism diverter includes an elastically deformable flexible member, wherein a force applied to the flexible member causes the flexible member to undergo elastic deformation into the divert state, thereby diverting the substantial fraction of emboli in one or more of the at least two directions.

3. The embolism deflecting device of claim 1, wherein
    the embolism diverter further comprises at least one fixed member, the at least one fixed member including at least one of a mesh, a screen, an obstructing member, a plurality of non-intersecting bars, or a spiral element, and
    in the divert state, at least a portion of the movable member overlaps at least a portion of the fixed member, the at least one of the mesh, screen, obstructing member, plurality of non-intersecting bars, or spiral element of the fixed member and the at least one of the mesh, screen, obstructing member, plurality of non-intersecting bars, or spiral element of the movable member together controlling a size of at least one opening dimensioned to divert a substantial fraction of emboli away from the more critical location.

4. The embolism deflecting device of claim 1, wherein:
    the embolism diverter includes a plurality of movable members, each movable member including at least one of a mesh, a screen, an obstructing member, a plurality of non-intersecting bars, or a spiral element, and
    in the divert state, at least portions of the plurality of movable members overlap each other, the at least one of the mesh, screen, obstructing member, plurality of non-intersecting bars, or spiral element of the plurality of movable members together controlling a size of at least one opening dimensioned to direct a substantial fraction of emboli away from the more critical location.

5. The embolism deflecting device of claim 1, wherein the at least one movable member of the embolism diverter is substantially neutrally buoyant with respect to blood.

6. The embolism deflecting device of claim 1, wherein the diverter controller is operable to activate one or more actuators on receiving at least one parameter associated with the number of emboli, the embolism size, the embolism type, the embolism location, the embolism path, or the embolism arrival time, the one or more actuators disposed between the support stent and the one or more movable members, thereby converting the embolism diverter from a non-divert state to the divert state.

7. The embolism deflecting device of claim 1, wherein the diverter controller includes an external input for receiving external commands setting the state of the embolism diverter.

8. The embolism deflecting device of claim 1, wherein the embolism detector is operable to determine at least one parameter associated with a number of emboli, an embolism size, an embolism type, an embolism location, an embolism path, or an embolism arrival time.

9. The embolism deflecting device of claim 1, wherein a detection field of the embolism detector is at least one of upstream of the embolism diverter or downstream of the embolism diverter.

10. An embolism deflecting device comprising:
    an embolism detector; a diverter controller operable to determine a presence of at least one embolism in a detection field of the embolism detector based on a target input therefrom;

a support stent dimensioned for deployment in a blood vessel; and an embolism diverter coupled to the support stent, the embolism diverter including at least one movable member, the movable member operable by the diverter controller to modulate the movable member between a non-divert position and a divert position based on a determination of the presence of at least one embolism by the diverter controller; and an implantable container disposed within a lumen defined by the support stent, the implantable container in fluid communication with the blood vessel at least part of the time, the embolism diverter deflecting the substantial fraction of emboli into the implantable container when the movable member is in the divert state.

11. A system for deflecting emboli, comprising:

an implantable embolism deflecting device including an embolism detector with an embolism detection field thereof upstream of an embolism diverter, the embolism detector operable for transmitting information associated with a presence or absence of an embolism in the detection field;

a diverter controller operatively coupled to the embolism detector, the diverter controller operable for receiving the information associated with the presence of absence of an embolism in the detection field from the embolism detector, the diverter controller including a processor;

a support stent including a substantially tubular frame substantially defining a lumen, the substantially tubular frame having a first end in fluid communication with a second end through the lumen, the first end having an inlet through which blood enters the support stent, the second end having an outlet through which blood exits the support stent, the substantially tubular frame of the support stent having an anchor for removably securing at least a portion of the support stent in the blood vessel; and an embolism diverter including one or more movable members movably secured to the substantially tubular support stent;

the embolism diverter coupled to the support stent, the embolism diverter having at least one movable member movable from a non-divert state to a divert state, the at least one movable member operable to divert a substantial fraction of emboli of at least a target size in one of at least two directions, the embolism diverter operatively coupled to and controllable by the diverter controller to convert the movable member from the non-divert state to the divert state in response to a detection of an embolism in the detection field of the embolism detector;

an implantable container disposed within the lumen defined by the support stent, the implantable container in fluid communication with the blood vessel at least part of the time, the embolism diverter deflecting the substantial fraction of emboli into the implantable container when the at least one movable member is in the divert state; and a processor configured to receive and read machine readable instructions that when executed by the processor, convert the movable member of the embolism diverter from the non-divert state to the divert state based on a target input.

12. The system of claim 11, wherein the diverter controller is operable to set the state of the embolism diverter according to at least one of type, location, size, presence, absence, time of passage, or route of an embolism.

13. The system of claim 11, wherein the diverter controller includes one or more control embolism diverter parameters that are updatable based on data provided from a second embolism detector with a detection field downstream of the embolism diverter.

14. The system of claim 11, wherein the diverter controller is programmable.

15. The embolism deflecting device of claim 1, wherein the implantable container includes a fill level detector configured to indicate a fill level of the implantable container.

16. The embolism deflecting device of claim 10, wherein the implantable container includes a fill level detector configured to indicate a fill level of the implantable container.

17. The system of claim 11, wherein the implantable container includes a fill level detector configured to indicate a fill level of the implantable container.

* * * * *